(12) United States Patent
Biedermann et al.

(10) Patent No.: US 7,241,745 B2
(45) Date of Patent: Jul. 10, 2007

(54) PYRIDYL ALKENE AND PYRIDYL ALKINE ACID AMIDES AS CYTOSTATICS AND IMMUNOSUPRESSIVES

(75) Inventors: Elfi Biedermann, Vaterstetten (DE); Max Hasmann, Neuried (DE); Roland Löser, Feldafing (DE); Benno Rattel, Munich (DE); Friedemann Reiter, Putzbrunn (DE); Barbara Schein, Neufahrn (DE); Klaus Seibel, Gräfelfing (DE); Klaus Vogt, Munich (DE)

(73) Assignee: Astellas Pharma GmbH (DE)

( * ) Notice: Subject to any disclaimer, the term of this patent is extended or adjusted under 35 U.S.C. 154(b) by 364 days.

(21) Appl. No.: 10/213,952

(22) Filed: Aug. 5, 2002

(65) Prior Publication Data

US 2003/0162972 A1 Aug. 28, 2003

Related U.S. Application Data

(63) Continuation of application No. 09/242,540, filed as application No. PCT/EP97/03245 on Jun. 20, 1997, now abandoned.

(30) Foreign Application Priority Data

Jun. 20, 1996 (DE) ................ 196 24 659

(51) Int. Cl.
- *A61K 31/44* (2006.01)
- *A61P 37/06* (2006.01)
- *C07D 401/12* (2006.01)
- *C07D 405/14* (2006.01)
- *C07D 409/14* (2006.01)

(52) U.S. Cl. .............. 514/89; 514/211.15; 514/217.04; 514/217.07; 514/249; 514/258; 514/291; 514/301; 514/304; 514/314; 514/316; 514/318; 514/332; 514/343; 540/479; 540/544; 540/589; 540/597; 544/278; 544/355; 546/21; 546/89; 546/114; 546/125; 546/172; 546/187; 546/193; 546/194; 546/265; 546/276.4; 546/278.4; 546/279.1

(58) Field of Classification Search ............. 514/89, 514/211.15, 217.04, 217.07, 249, 258, 291, 514/301, 304, 314, 316, 318, 332, 343; 540/479, 540/544, 589, 597; 544/278, 355; 546/21, 546/89, 114, 125, 172, 187, 193, 194, 265, 546/276.4, 278.4, 279.1

See application file for complete search history.

(56) References Cited

U.S. PATENT DOCUMENTS

| | | | |
|---|---|---|---|
| 4,283,541 A | 8/1981 | Shroff et al. | 546/336 |
| 5,169,856 A * | 12/1992 | Goto et al. | 514/331 |
| 5,260,323 A | 11/1993 | Baader et al. | 514/356 |
| 5,326,772 A | 7/1994 | Klemm et al. | 514/318 |
| 6,444,823 B1 * | 9/2002 | Biedermann et al. | 546/208 |
| 6,451,816 B1 * | 9/2002 | Biedermann et al. | 514/318 |

FOREIGN PATENT DOCUMENTS

| | | |
|---|---|---|
| CA | 2085954 | 6/1993 |
| DE | 4020570 | 1/1992 |
| EP | 048045 | 3/1982 |
| EP | 0271023 | 12/1986 |
| EP | 0210782 | 2/1987 |
| EP | 0330026 | 8/1989 |
| EP | 0343307 | 11/1989 |
| EP | 0428434 | 11/1990 |
| EP | 0416581 | 3/1991 |
| EP | 0471236 | 2/1992 |
| EP | 0479601 | 4/1992 |
| EP | 0512902 | 11/1992 |
| EP | 0522606 | 1/1993 |
| EP | 0530444 | 3/1993 |
| EP | 0548883 | 6/1993 |
| GB | 2304714 | 11/1998 |
| JP | 63179869 | 7/1988 |
| WO | WO 89/07443 | 8/1989 |
| WO | WO 91/15484 | 10/1991 |
| WO | WO 91/15485 | 10/1991 |

(Continued)

OTHER PUBLICATIONS

Ross, "The Preparation of Some 4-Substituted Nicotinic Acids and Nicotinamides", *J.Chem.Soc.* (*C*), 1966, 1816-1821.

(Continued)

*Primary Examiner*—Brenda Coleman
(74) *Attorney, Agent, or Firm*—Fitch, Even, Tabin & Flannery

(57) ABSTRACT

The invention relates to a new pyridyl alkene and pyridyl alkine acid amides according to the general formula (I)

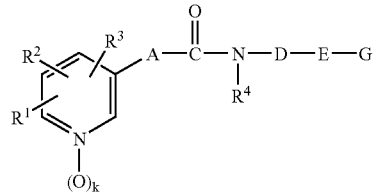

as well as methods for their production, medicaments containing these compounds as well as their medical use, especially in the treatment of tumors or for immunosuppression.

9 Claims, No Drawings

FOREIGN PATENT DOCUMENTS

| | | |
|---|---|---|
| WO | WO 93/13083 | 7/1993 |
| WO | WO 93/14070 | 7/1993 |
| WO | WO 93/14113 | 7/1993 |
| WO | WO 94/01402 | 1/1994 |
| WO | WO 95/10514 | 1/1995 |
| WO | WO 95/10515 | 4/1995 |
| WO | WO 95/10516 | 4/1995 |
| WO | WO 95/24894 | 9/1995 |
| WO | WO 96/31477 | 10/1996 |
| WO | WO 96/31478 | 10/1996 |
| WO | WO 97/48397 | 12/1997 |
| WO | WO 97/48695 | 12/1997 |

OTHER PUBLICATIONS

Ishihara et al., Central Cholinergic Agents. II. Synthesis and Acetylcholinesterase Inhibitory Activities of N-(w-[N-Alkyl-N-(pheynylmethyl)amino]alkyl]-3-arylpropenamides:, *Chem.Pharm. Bull.*, 37(12), 1991, pp. 3236-3243.

Nishikawa et al., "Acrylamide Derivatives as Antiallergic Agents. 2. Synthesis and Structure-Activity Relationships of N-[[4-[4[(Diphenylmethyl)-1-piperazinyl]butyl]-3-(3-pyridyl)acrylamides", *J. Med. Chem.*, 32, 1989, pp. 583-593.

Nishikawa et al., "Acrylamide Derivatives as Antiallergic Agents. I. Synthesis and Structure-Activity Relationships of N-[(4-Substituted 1-piperazinyl)alkyl]-3-(aryl and heteroaryl) acrylamides", *Chem. Pharm. Bull*, 37(1) 1989, pp. 100-105.

Fischer et al., "Allegemeine Immunologie und Immunpathologie", *Allgemeine Pathologie und Pathologische Anatomie*, 33$^{rd}$ edition, 1990, pp. 208-213.

"150041w", *Chemical Abstracts*, 115, 1991, p. 48.

"173015r", *Chemical Abstracts*, 124(13), 1996, p. 1004.

"86013", *Rote Liste*, 1997, p. 86.

\* cited by examiner

PYRIDYL ALKENE AND PYRIDYL ALKINE ACID AMIDES AS CYTOSTATICS AND IMMUNOSUPRESSIVES

This application is a continuation of U.S. application Ser. No. 09/242,540, filed Feb. 18, 1999, now abandoned, which is a national phase filing of international application PCT/EP97/03245, filed Jun. 20, 1997, designating the United States, which is hereby incorporated by reference herein in their entirety.

The invention relates to new pyridine compounds, methods for their production, medicaments containing these compounds as well as their use, especially in the treatment of tumor conditions and/or as cytostatic agents or as immunosuppressive agents.

A pressing need exists for cytostatic therapy to provide new pharmaceuticals and/or medicaments which not only possess a strong activity, but also exert diminished side effects in comparison to many classical cancerostatic agents, whereby treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator, etc.), with operative procedures, heat treatment, etc.

In this connection, a strong need also exists to enrich tumor therapy with new compounds for overcoming or preventing resistances for example.

This object was successfully solved in a completely surprising manner by making available the pyridyl alkane acid amide derivatives defined below.

It was known that various pyridine compounds substituted in a specific manner have pharmacologically useful properties which lie however in completely different indication areas.

Thus, ω-pyridyl alkane and/or alkene amides with anti-allergic activity are described in EP 0 210 782 which are referred to as having a 5-lipoxygenase-inhibiting and anti-histamine action, wherein the amide components of these compounds contain a piperizine or homopiperizine ring and the pyridine ring can be linked together in the 2-, 3- or 4-position. JP 63,179,869 describes further pyridyl amides, ω-pyridyl alkane and alkene amides as anti-allergic effective substances containing a substituted piperidine ring in the amine component. Such compounds with the same properties are mentioned in Chem. Pharm. Bull 37, 100–105 (1989) and in J. Med. Chem. 1989, 583–593.

Pyridyl ureas, pyridyl thioureas and pyridyl carbonamides, wherein the amide portion is bound over an aryl substituted alkyl chain with a piperidine ring or piprazine ring, are described for example in EP-A-0 428 434 or in EP-A-0 512 902 as antagonists of the neurokinin receptor and substance P. Furthermore, pyridyl(alkyl)carbonamides, pyridyl(alkyl)sulfonamides and analogous ureas, wherein the amide portion is bound over an alkyl chain with a piperidine ring are disclosed in EP-A-0 479 601 as active ingredients with anti-arrhythmic properties.

In WO 91/15 485, the production of pyridine-3,5-dicarboxylic acid esters and amides as well as their use for the treatment of tumor conditions is described. These compounds differ from the compounds according to the invention described below in very important structural features, for example by the dicarboxyl grouping on the pyridine ring or the absence of the hydrocarbon chain between the pyridine ring and the amide grouping. The compounds disclosed in WO 89/07 443 in the form of optically pure R(−)-Niguldipine and further analogous dihydropyridines with cytotoxic activity have larger structural differences. As compared to these known compounds, the compounds according to the invention unexpectedly possess a better activity and a wider spectrum of action despite the large structural differences.

Structurally closely related compounds are represented by the piperidine compounds described in EP-A-0 330 026. However, no 3-pyridyl derivatives were concretely described and no concrete examples were disclosed in this publication, aside from a single compound which is described below. These known compounds are distinguished by an anti-cholinesterase activity, an anti-amnesia activity as well as activities directed against hyperkinesia, senile dementia, mania and Alzheimer's disease.

In view of this art, the finding that the compounds according to the general formula (I) defined below have activities which make them particularly suitable in an excellent manner for the therapy of tumor illnesses was completely unexpected. The pharmacological finding that the compounds according to the invention also possess immunosuppressive properties besides cytostatic activity is to be considered as equally surprising.

Pharmacological test results from which this conclusion must be drawn, as well as the concrete tumor indications and combination possibilities are detailed and illustrated in the last part of the description.

Therefore, subject-matter of the invention relates to compounds of formula (I)

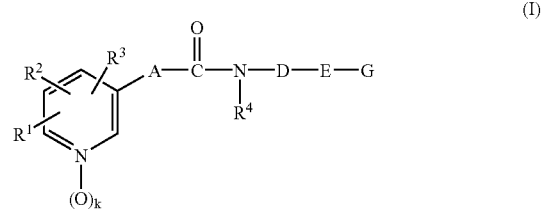

wherein
$R^1$ is hydrogen, halogen, cyano, trifluoromethyl, hydroxy, benzyloxy,
aminocarbonyl, carboxy, phenyl, phenoxy, phenylthio, pyridyloxy, pyridylthio,
alkyl, especially $C_1$–$C_6$-alkyl,
alkenyl, especially $C_3$–$C_6$-alkenyl,
alkinyl, especially $C_3$–$C_6$-alkinyl,
hydroxyalkyl, especially $C_1$–$C_6$-hydroxyalkyl,
alkoxy, especially $C_1$–$C_6$-alkoxy,
alkenyloxy, especially $C_3$–$C_6$-alkenyloxy,
alkinyloxy, especially $C_3$–$C_6$-alkinyloxy,
alkanoyloxy, especially $C_1$–$C_7$-alkanoyloxy,
alkoxycarbonyloxy, especially $C_2$–$C_7$-alkoxycarbonyloxy,
alkylthio, especially $C_1$–$C_6$-alkylthio,
alkenylthio, especially $C_3$–$C_6$-alkenylthio,
alkinylthio, especially $C_3$–$C_6$-alkinylthio,
cycloalkyl, especially $C_3$–$C_8$-cycloalkyl,
cycloalkyloxy, especially $C_3$–$C_8$-cycloalkyloxy,
cycloalkylthio, especially $C_3$–$C_8$-cycloalkylthio,
alkoxycarbonyl, especially $C_2$–$C_7$-alkoxycarbonyl,
alkylaminocarbonyl, especially $C_2$–$C_7$-alkylaminocarbonyl, dialkylaminocarbonyl, especially $C_3$–$C_{13}$-dialkylaminocarbonyl, or
$NR^5R^6$, wherein
$R^5$ and
$R^6$ are selected independently of each other from hydrogen,
  alkyl, especially $C_1$–$C_6$-alkyl,
  alkenyl, especially $C_3$–$C_6$-alkenyl and
  alkinyl, especially $C_3$–$C_6$-alkinyl,
$R^2$ is hydrogen, halogen, cyano, hydroxy, trifluoromethyl, benzyloxy,
  alkyl, especially $C_1$–$C_6$-alkyl,
  alkoxy, especially $C_1$–$C_6$-alkoxy or
  alkanoyloxy, especially $C_1$–$C_7$-alkanoyloxy,
  wherein $R^1$ and $R^2$, if they are adjacent, optionally form a bridge which is selected from
    —$(CH_2)_4$—, —$(CH{=}CH)_2$— and —$CH_2O$—$CR^7R^8$—O—, wherein
$R^7$ and
$R^8$ are, independently of each other, hydrogen or alkyl, especially $C_1$–$C_6$-alkyl,
$R^3$ is hydrogen, halogen, alkyl, especially $C_1$–$C_6$-alkyl, trifluoromethyl or hydroxyalkyl, especially $C_1$–$C_6$-hydroxyalkyl and
$R^4$ is hydrogen, hydroxy, benzyloxy,
  alkyl, especially $C_1$–$C_6$-alkyl,
  alkenyl, especially $C_3$–$C_6$-alkenyl,
  alkinyl, especially $C_3$–$C_6$-alkinyl,
  cycloalkyl, especially $C_3$–$C_6$-cycloalkyl or
  alkoxy, especially $C_1$–$C_6$-alkoxy,
k is 0 or 1,
A is alkenylene, especially $C_2$–$C_6$-alkenylene, which is optionally substituted once to three-fold by $C_1$–$C_3$-alkyl, hydroxy, $C_1$–$C_3$-alkoxy, fluorine, cyano or phenyl,
  alkadienylene with at least four C-atoms, especially $C_4$–$C_6$-alkadienylene, which is optionally substituted once or twice by $C_1$–$C_3$-alkyl, fluorine, cyano or phenyl,
  1,3,5-hexatrienylene, which is optionally substituted by $C_1$–$C_3$-alkyl, fluorine, cyano, or phenyl,
  ethinylene
D is selected from alkylene, especially $C_1$–$C_{10}$-alkylene, optionally substituted once or twice by alkyl, especially $C_1$–$C_6$-alkyl, hydroxy, or alkoxy, especially $C_1$–$C_6$-alkoxy,
  alkenylene with at least two C-atoms, especially $C_2$–$C_{10}$-alkenylene, which is optionally substituted once or twice by alkyl, especially $C_1$–$C_6$-alkyl, hydroxy, or alkoxy, especially $C_1$–$C_6$-alkoxy, wherein the double bond can also be to ring E,
  alkinylene with at least three C-atoms, especially $C_3$–$C_{10}$-alkinylene, optionally substituted once or twice by alkyl, especially $C_1$–$C_6$-alkyl, hydroxy or alkoxy, especially $C_1$–$C_6$-alkoxy, and
  alkylene, especially $C_1$–$C_{10}$-alkylene, alkenylene with at least two C-atoms, especially $C_2$–$C_{10}$-alkenylene or alkinylene with at least three C-atoms, especially $C_3$–$C_{10}$-alkinylene, whereby one to three methylene units are each isosterically replaced by O, S, $NR^9$, CO, SO or $SO_2$ wherein
$R^9$ is selected from hydrogen, alkyl especially $C_1$–$C_6$-alkyl, alkenyl, especially $C_3$–$C_6$-alkenyl, alkinyl, especially $C_3$–$C_6$-alkinyl, acyl, especially $C_1$–$C_6$-acyl or alkylsulfonyl, especially $C_1$–$C_6$-alkylsulfonyl, E is selected from

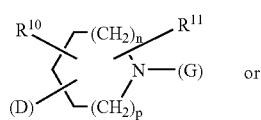  (E1)

or

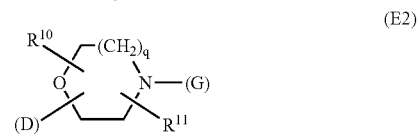  (E2)

wherein the heterocyclic ring can also optionally have a double bond and
n and
p can be, independently of one another, 0, 1, 2 or 3, with the proviso that $n+p \leq 4$ and
q is 2 or 3,
$R^{10}$ is hydrogen, alkyl, especially $C_1$–$C_6$-alkyl, hydroxy, hydroxymethyl, carboxy or alkoxycarbonyl with at least two C-atoms, especially $C_2$–$C_7$-alkoxycarbonyl and
$R^{11}$ is hydrogen, alkyl, especially $C_1$–$C_6$-alkyl or an oxo group adjacent to the nitrogen atom, wherein
$R^{10}$ and $R^{11}$ optionally together, form an alkylene bridge with 1, 2, 3, 4 or 5 C-atoms, especially a $C_1$–$C_3$-alkylene bridge under formation of a bicyclic ring system,
G is selected from hydrogen,
  G1, G2, G3, G4 and G5, wherein
  G1 represents the residue

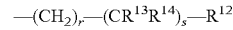  (G1)

wherein
r is an integer from 1 to 3 or 0 and
s is 0 or 1,
$R^{12}$ is selected from hydrogen, alkyl, especially $C_1$–$C_6$-alkyl, alkenyl with at least three C-atoms, especially $C_3$–$C_6$-alkenyl, alkinyl with at least three C-atoms, especially $C_3$–$C_6$-alkinyl, cycloalkyl with at least three C-atoms, especially $C_3$–$C_8$-cycloalkyl,
  saturated, five to seven membered heterocycles, which can contain one or two hetero-atoms from the group N and/or S and/or O,
  benzyl or phenyl,
  monocyclic aromatic five or six-membered heterocycles, which can contain one to three hetero-atoms from the group N and/or S and/or O and are either bound directly or over a methylene group,
  anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
  anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group,
$R^{13}$ has the same meaning as $R^{12}$, but is selected independently thereof,
$R^{14}$ is selected from hydrogen, hydroxy, methyl, benzyl, phenyl,
  monocyclic aromatic five- or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, G2 is the residue

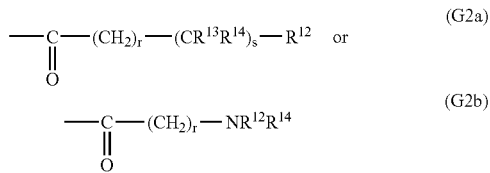

wherein the substituents $R^{12}$ and $R^{14}$ can have the above meaning or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from the group N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue

and

G4 is the residue

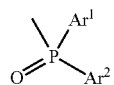

wherein $Ar^1$ and $Ar^2$ are selected independently from one another from phenyl, pyridyl or naphthyl and G5 is the residue

wherein $R^{15}$ is selected from trifluoromethyl, alkoxy, especially $C_1$–$C_6$-alkoxy, alkenyloxy, especially $C_3$–$C_6$-alkenyloxy, or benzyloxy, wherein any aryl residues and/or aromatic ring systems in the substituents $R^1$, $R^2$, $R^4$, $R^{12}$, $R^{13}$, $R^{14}$, $R^{15}$, $Ar^1$ and $Ar^2$ and/or in the ring system —$NR^{12}R^{14}$ can be substituted independently from each other by one to three of the same or different residues which are selected from halogen, cyano, alkyl, especially $C_1$–$C_6$-alkyl, trifluoromethyl, cycloalkyl, especially $C_3$–$C_8$-cycloalkyl, phenyl, benzyl, hydroxy, alkoxy, especially $C_1$–$C_6$-alkoxy, alkoxy, substituted entirely or partially by fluorine, substituted alkoxy especially $C_1$–$C_6$-alkoxy, benzyloxy, phenoxy, mercapto, alkylthio, especially $C_1$–$C_6$-alkylthio, carboxy, alkoxycarbonyl, especially $C_1$–$C_6$-alkoxycarbonyl, benzyloxycarbonyl, nitro, amino, monoalkylamino, especially mono-$C_1$–$C_6$-alkylamino, dialkylamino, especially di-($C_1$–$C_6$-alkyl)-amino and methylenedioxy for two adjacent groups on the aromatic ring or ring system, wherein each of the residues alkyl, alkenyl, alkinyl, hydroxyalkyl, alkoxy, alkenyloxy, alkinyloxy, alkanoyloxy, alkoxycarbonyl, alkoxycarbonyloxy, alkylthio, alkenylthio, alkinylthio, alkylene, acyl, alkylsulfonyl, alkenylene, alkinylene, cycloalkyl, cycloalkyloxy, alkoxycarbonyl, alkylaminocarbonyl or dialkylaminocarbonyl of the substituents $R^1$ to $R^{13}$ can have 1 to 2 or 4, 6, 8, 10 or 12 C-atoms and/or 2 or 3 to 5, 7, 9, 11 or 13 and/or 15 C-atoms or 4, 5, 6, 7, 8, 9, 10, 11, 12, 13, 14 or 15 C-atoms depending on the structure, as well as stereoisomers and/or mixtures thereof and pharmacologically acceptable acid addition salts thereof with the exception of (E)-3-(3-pyridyl)-N-[2-(1-benzylpiperidin-4-yl)ethyl]-2-propenamide hydrochloride.

A preferred embodiment according to the invention relates to compounds of formula (I)

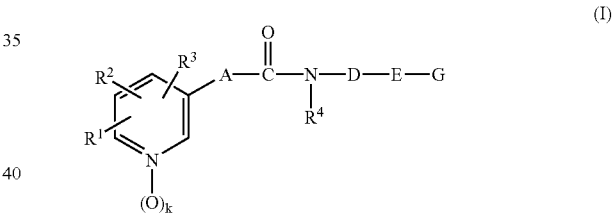

wherein $R^1$ is a hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, or $NR^5R^6$, wherein $R^5$ and $R^6$ are selected independently from each other from hydrogen, $C_1$–$C_6$-alkyl, $C_3$–$C_6$-alkenyl and $C_3$–$C_6$-alkinyl, $R^2$ is hydrogen, halogen, cyano, $C_1$–$C_6$-alkyl, trifluoromethyl, hydroxy, $C_1$–$C_6$-alkoxy, benzyloxy or $C_1$–$C_7$-alkanoyloxy, wherein $R^1$ and $R^2$, in case they are adjacent, optionally form a bridge which is selected from the bridge members

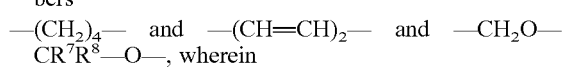, wherein $R^7$ and
$R^8$ are, independently from each other, hydrogen or $C_1$–$C_6$-alkyl,
$R^3$ is hydrogen, halogen, $C_1$–$C_6$-alkyl, trifluoromethyl or $C_1$–$C_6$-hydroxyalkyl and
$R^4$ is hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy or benzyloxy,
k is 0 or 1,
A is $C_2$–$C_6$-alkenylene, which is optionally substituted once to three-fold by $C_1$–$C_3$-alkyl, hydroxy, $C_1$–$C_3$-alkoxy, fluorine, cyano or phenyl,
$C_4$–$C_6$— alkadienylene, which is optionally substituted once or twice by $C_1$–$C_3$-alkyl, fluorine, cyano or phenyl
1,3,5-hexatrienylene, which is optionally substituted by $C_1$–$C_3$-alkyl, fluorine, cyano or phenyl as well as ethinylene,
D is selected from $C_1$–$C_{10}$-alkylene, optionally substituted once or twice by $C_1$–$C_6$-alkyl, hydroxy, or $C_1$–$C_6$-alkoxy,
$C_2$–$C_{10}$-alkenylene, which is optionally substituted once or twice by $C_1$–$C_6$-alkyl, hydroxy, or $C_1$–$C_6$-alkoxy, wherein the double bond can also be to ring E,
$C_3$–$C_{10}$-alkinylene, optionally substituted once or twice by $C_1$–$C_6$-alkyl, hydroxy, or $C_1$–$C_6$-alkoxy, and
$C_1$–$C_{10}$-alkylene, $C_2$–$C_{10}$-alkenylene or $C_3$–$C_{10}$-alkinylene, wherein one to three methylene units are each isosterically replaced by O, S, $NR^9$, CO, SO or $SO_2$, wherein
$R^9$ is selected from hydrogen, $C_1$–$C_6$-alkyl, $C_3$–$C_6$-alkenyl, $C_3$–$C_6$-alkinyl, $C_1$–$C_6$-acyl or $C_1$–$C_6$-alkylsulfonyl,
E is selected from

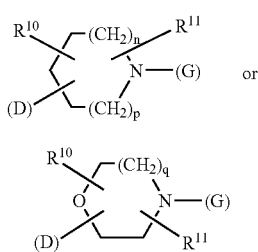

(E1)

(E2)

wherein the heterocyclic ring can optionally have a double bond and
n and
p can be, independently of each other, 0, 1, 2 or 3, with the proviso that n+p≦4 and
q is 2 or 3,
$R^{10}$ is hydrogen, $C_1$–$C_6$-alkyl, hydroxy, hydroxymethyl, carboxy or $C_2$–$C_7$-alkoxycarbonyl and
$R^{11}$ hydrogen, $C_1$–$C_6$-alkyl or an oxo group adjacent to the nitrogen atom, wherein
$R^{10}$ and $R^{11}$ optionally together form a $C_1$–$C_3$-alkylene bridge under formation of a bi-cyclic ring system,
G is selected from hydrogen,
G1, G2, G3, G4 and G5, wherein
G1 represents the residue —$(CH_2)_r$—$(CR^{13}R^{14})_s$—$R^{12}$ (G1)

wherein
r is an integer from 1 to 3 or 0 and
s is 0 or 1,
$R^{12}$ is selected from hydrogen, $C_1$–$C_6$-alkyl, $C_3$–$C_6$-alkenyl, $C_3$–$C_6$-alkinyl, $C_3$–$C_8$-cycloalkyl, saturated, five- to seven-membered heterocycles, which can contain one or two hetero-atoms from the group N and/or S and/or O.
benzyl or phenyl,
monocyclic aromatic five or six membered heterocycles, which can contain one to three hetero-atoms from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group,
$R^{13}$ has the same meaning as $R^{12}$, but is selected independently thereof,
$R^{14}$ is selected from hydrogen, hydroxy, methyl, benzyl, phenyl,
monocyclic aromatic five- or six-membered heterocycles, which can contain one to three hetero-atoms selected from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group,
G2 is the residue

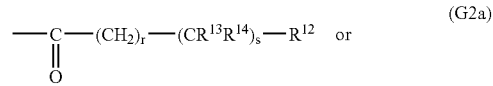

(G2a)

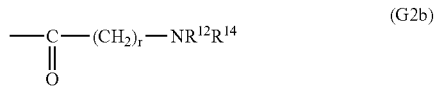

(G2b)

wherein the substituents $R^{12}$ and $R^{14}$ can have the above meaning or the grouping

can also be a nitrogen heterocycle bound over the nitrogen atom, selected from
saturated or unsaturated monocyclic, four- to eight-membered heterocycles, which, aside from the essential nitrogen atom, can optionally contain one or two further hetero-atoms selected from the group N and/or S and/or O, or
saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue

and
G4 is the residue

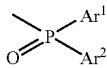

wherein
Ar$^1$ and Ar$^2$ are selected independently from one another from phenyl, pyridyl or naphthyl and
G5 is the residue

—COR$^{15}$ (G5)

wherein
R$^{15}$ is selected from trifluoromethyl, C$_1$–C$_6$-alkoxy, C$_3$–C$_6$-alkenyloxy, or benzyloxy, and wherein aromatic ring systems in the substituents R$^1$, R$^2$, R$^4$, R$^{12}$, R$^{13}$, R$^{14}$, R$^{15}$, Ar$^1$ and Ar$^2$ and/or in the ring system —NR$^{12}$R$^{14}$ can be substituted independently from each other by one to three of the same or different residues which are selected from halogen, cyano, C$_1$–C$_6$-alkyl, trifluoromethyl, C$_3$–C$_8$-Cycloalkyl, phenyl, benzyl, hydroxy, C$_1$–C$_6$-alkoxy, which can optionally be entirely or partially substituted by fluorine, benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino or di-(C$_1$–C$_6$-alkyl)-amino and methylenedioxy for two adjacent groups on the aromatic ring or ring system, stereoisomers thereof and/or mixtures thereof and pharmacologically acceptable acid addition salts with the exception of (E)-3-(3-pyridyl)-N-[2-(1-benzylpiperidin-4-yl)ethyl]-2-propenamide hydrochloride.

A further preferred embodiment of the invention constitutes compounds of the invention, which are distinguished in that substituents R$^1$, R$^2$, R$^3$, R$^4$, R$^5$, R$^6$, R$^7$, R$^8$, R$^9$, R$^{12}$, R$^{13}$, R$^{14}$ and R$^{15}$ as well as A and D labelled therein have the following meaning in connection with the given substitutions according to this formula

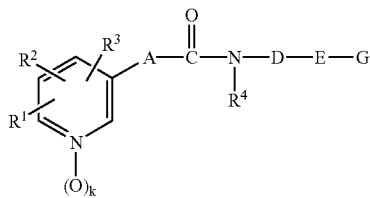

wherein
halogen is fluorine, chlorine, bromine or iodine,

C$_1$–C$_6$-alkyl can be straight chain or branched and is preferably a methyl-, ethyl-, propyl-, isopropyl-, butyl-, isobutyl-, sec-butyl-, tert-butyl-, cyclopropylmethyl-, pentyl-, isopentyl-, tert-pentyl-, neopentyl-, cyclopropylethyl-, cyclobutylmethyl- or a hexyl group, alkylene is for example methylene, ethylene, propylene, tetramethylene, pentamethylene, hexamethylene, heptamethylene, octamethylene, nonamethylene or decamethylene, C$_3$–C$_6$-alkenyl can be straight chain or branched and is preferably an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl group, alkenylene is for example ethenylene, propenylene, butenylene, pentenylene, hexenylene, hexathenylene, heptenylene, octenylene, nonenylene or decenylene, C$_3$–C$_6$-alkinyl can be straight chain or branched and is preferably a propargyl-, 2-butinyl-, 3-butinyl-, 4-pentinyl-, 5-hexinyl- or 4-methyl-2-pentinyl group, alkinylene is for example propinylene, butinylene, pentinylene, hexinylene, heptinylene, octinylene, noninylene or decinylene, C$_3$–C$_8$-cycloalkyl is preferably cyclopropyl, cyclobutyl, cyclopentyl, cyclohexyl, cycloheptyl or cyclooctyl, C$_1$–C$_6$-hydroxyalkyl contains a hydroxyl group in one of the above-named C$_1$–C$_6$-alkyl residues, especially in the form of the hydroxymethyl- and hydroxyethyl group, wherein C$_1$–C$_6$-alkoxy, C$_3$–C$_6$-alkenyloxy, C$_3$–C$_6$-alkenyloxy each contain, aside from the oxygen atom, one of the C$_1$–C$_6$-alkyl-, C$_3$–C$_6$-alkenyl- and/or C$_3$–C$_6$-alkinyl groups named above and the methoxy-, ethoxy-, isopropoxy-, tert-butoxy-, allyloxy- and propargyloxy group are preferred and is to be understood as among C$_1$–C$_6$-alkoxy entirely or partially substituted with fluorine, for example difluormethoxy, trifluormethoxy or 2,2,2-trifluorethoxy, —

C$_1$–C$_6$-alkylthio, C$_3$–C$_6$-alkenylthio, C$_3$–C$_6$-alkinylthio each contain, aside from the sulfur atom, one of the C$_1$–C$_6$-alkyl-, C$_3$–C$_6$-alkenyl- or C$_3$–C$_6$-alkinyl group named above, especially the methylthio-, ethylthio-, isopropylthio- and tert-butylthio groups, C$_3$–C$_8$-cycloalkyloxy and C$_3$–C$_8$-cycloalkylthio are preferred as cyclopentyloxy- and cyclopentylthio- and/or cylohexyloxy- and cyclohexylthio groups, C$_1$–C$_7$-alkanoyloxy groups contain, aside from the oxygen atom, an aliphatic acyl residue with 1 to 7 carbon atoms, especially the acetoxy-, propionyloxy- and pivaloyloxy group, C$_2$–C$_7$-alkoxycarbonyl groups contain, aside from the carbonyl group, one of the C$_1$–C$_6$-alkoxy groups mentioned above, especially the methoxycarbonyl-, ethoxycarbonyl-, isopropoxycarbonyl-, isobutoxycarbonyl- and tert-butoxycarbonyl group, C$_2$–C$_7$-alkoxycarbonyloxy groups contain, aside from the oxygen atom, one of the C$_2$–C$_7$-alkoxycarbonyl residues mentioned above, especially the methoxycarbonyloxy-, ethoxycarbonyloxy-, isopropoxycarbonyloxy-, isobutoxycarbonyloxy- and tert-butoxycarbonyl group as well as the allyloxycarbonyloxy group, C$_2$–C$_7$-alkylaminocarbonyl and C$_3$–C$_{13}$-dialkylaminocarbonyl groups contain, beside the carbonyl group, an alkylamino- and/or dialkylamino residue, whose C$_1$–C$_6$-alkyl groups have the above meanings, wherein the dimethylaminocarbonyl-, diethylaminocarbonyl- and the diisopropylaminocarbonyl groups are preferred, and aside from the unsubstituted amino group, one of the following C$_1$–C$_6$- alkylamino groups and/or di-($C_1$–$C_6$-alkyl)amino groups are to be understood under the amino groups of the formula $NR^5R^6$, $C_1$–$C_6$-alkylamino contains one of the $C_1$–$C_6$-alkyl groups mentioned above, especially in form of the methylamino-, ethylamino-, propylamino-, isopropylamino-, butylamino- and the tert-butylamino group, di-($C_1$–$C_6$-alkyl)amino carries two of the same or different of the above named $C_1$–$C_6$-alkyl groups on the nitrogen atom, especially in form of the dimethylamino-, diethylamino-, dipropylamino-, diisopropylamino-, isopropylmethylamino-, dibutylamino- or tert-butylmethylamino group, $C_1$–$C_6$-acyl is the residue of an aliphatic saturated or unsaturated, straight chain, branched or cyclic carboxylic acid, especially in form of the formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and the dimethylacryloyl group, $C_1$–$C_6$-alkansulfonyl is preferably the methanesulfonyl-, ethanesulfonyl-, propanesulfonyl-, butanesulfonyl-, pentanesulfonyl- and the hexanesulfonyl group, saturated five- to seven-membered heterocycles with one or two hetero-atoms are especially tetrahydrofuryl, tetrahydrothienyl, pyrrolidinyl, tetrahydropyranyl, piperidinyl, hexahydroazepinyl, piperazinyl, hexahydrodiazepinyl or morpholinyl, monocyclic aromatic five- or six-membered heterocycles with one to three hetero-atoms are especially furyl, thienyl, pyrrolyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, pyrimidinyl or triazinyl, anellated bi- and tricyclic aromatic or partially hydrated carbocycle ring systems with 8 to 16 ring atoms and at least one aromatic ring are preferably benzocyclobutyl, indanyl, indenyl, naphthyl, dihydronaphthyl, tetahydronaphthyl, biphenylenyl, fluorenyl, anthryl, dihydroanthryl, phenanthryl, dihydrophenanthryl, dibenzocycloheptenyl, dihydrodibenzocycloheptenyl, dihydrodibenzocyclooctenyl or tetrahydrodibenzocyclooctenyl, wherein mono- or dioxoderivates, wherein the residues of indanone, tetralone, anthrone, anthraquinone, fluorenone, phenanthrone, dibenzocycloheptenone, dihydrodibenzocycloheptenone or tetrahydrodibenzocyclooctenone are for example also to be understood as partially hydrated carbocyclic ring systems, anellated bi- and tricyclische aromatic or partially hydrated heterocyclic ring systems with 8 to 16 ring atoms and at least one aromatic ring are, for example, imidazothiazolyl, benzofuryl, dihydrobenzofuryl, benzothienyl, dihydrobenzothienyl, indolyl, indolinyl, benzimidazolyl, indazolyl, benzoxazolyl, benzisoxazolyl, benzo-thiazolyl, benzisothiazolyl, benzofurazanyl, benzothiadiazolyl, benzotriazolyl, oxazolopyridyl, thiazolopyridyl, isothiazolopyridyl, imidazopyridyl, pyrazolopyridyl, thienopyrimidinyl, chromanyl, benzopyranyl, quinolyl, isoquinolyl, dihydroquinolyl, tetrahydroquinolyl, benzodioxanyl, quinoxalinyl, quinazolinyl, naphthyridinyl, carbazolyl, tetrahydrocarbazolyl, pyridoindolyl, acridinyl, phenothiazinyl, dihydrodibenzoxepinyl, benzocycloheptathienyl, dihydrothienobenzothiepinyl, dihydrodibenzothiepinyl, octahydrodibenzothiepinyl, dihydrodibenzazepinyl, octahydrodibenzazepinyl, benzocycloheptapyridinyl, dihydropyridobenzodiazepinyl, dihydrobenzoxazepinyl, dihydropyridobenzoxepinyl, dihydropyridobenzoxazepinyl, dihydrodibenzothiazepinyl or dihydropyridobenzothiazepinyl, wherein their mono- or dioxo-derivates and/or optionally their possible tautomeres are also to be understood as partially hydrated heterocyclic ring systems, for example, the residues of indolinone, isatin, benzoxazolone and/or its tautomeres hydroxybenzoxazol, of benzisoxazolone, benzothiazolone, benzoisothiazolone and benzimidazolone and/or their tautomeres, hydroxybenzisoxazol, hydroxybenzothiazol, hydroxybenzoisothiazol and hydroxybenzimidazol, of indazolinone, of oxazolopyridinone, thiazolopyridinones, pyrazolopyridinones and imidazopyridinones and/or their tautomeres hydroxyoxazolopyridine, hydroxythiazolopyridines, hydroxypyrazolopyridines and hydroxyimidazopyridines, the residues of chromanone, chromone, quinolinone, dihydroquinolinone, tetrahydrocarbazolone, acridone, of dihydrodibenzoxepinones, benzocycloheptathiophenones, dihydrothienobenzothiepinones, dihydrodibenzothiepinones, dihydrodibenzoazepinones, benzocycloheptapyridinones, dihydropyridobenzoxazepinones, dihydrodibenzothiazepinones and of dihydropyridobenzothiazepinones, saturated and unsaturated monocyclic, four- to eight-membered heterocycles represent —$NR^{12}R^{14}$ as a grouping which, aside from the essential nitrogen atom, can optionally contain one or two further hetero-atoms selected from N and/or S and/or O, for example azetidine, pyrrolidine, piperidine, (1H)tetrahydropyridine, hexahydroazepine, (1H)tetrahydroazepine, octahydroazocine, pyrazolidine, piperazine, hexahydrodiazepine, morpholine, hexahydrooxazepine, thiomorpholine or thiomorpholine-1,1-dioxide, saturated or unsaturated bi- or tricyclic, anellated or bridged heterocycles with 8 to 16 ring atoms, represent —$NR^{12}R^{14}$ as a grouping which, aside from the essential nitrogen atom optionally contain one or two further hetero-atoms, selected from N and/or S and/or O, for example 5-aza-bicyclo[2.1.1]hexane, 2-aza-bicyclo[2.2.1]heptane, 7-aza-bicyclo[2.2.1]heptane, 2,5-diaza-bicyclo[2.2.1]heptane, 2-aza-bicyclo[2.2.2]octane, 8-aza-bicyclo[3.2.1]octane, 2,5-diaza-bicyclo[2.2.2]octane, 9-aza-bicyclo[3.3.1]nonane, indoline, isoindoline, (1H)-dihydroquinoline, (1H)-tetrahydroquinoline, (2H)-tetrahydroisoquinoline, (1H)tetrahydroquinoxaline, (4H)-dihydrobenzoxazine, (4H)-dihydrobenothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indol, (10H)-dihydroacridine, 1,2,3,4-tetrahydroacridanone, (10H)-phenoxazin, (10H)-phenothiazine, (5H)-dibenzazepine, (5H)-dihydrodibenzazepine, (5H)-octahydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine or (5H) -tetrahydrodibenezaocine, as well as typical tautomeres in the case of substitution of the heterocycle as such or in an anellated ring system by free hydroxy-, mercapto- and/or amino groups, and stereoisomers such as, if applicable, cis/trans-isomers, endo/exo-isomers, optic isomers such as enantiomers, diastereomers as pure isomers or mixtures and/or racemic mixtures as well as the pharmacologically acceptable acid addition salts with inorganic or organic acids, wherein the hydrochlorides, hydrobromides, hydroiodides, sulfates and phosphates, are preferred as addition salts with suitable inorganic acids and acetates, benzoates, citrates, fumarates, gluconates, malates, maleates, methanesulfonates, lactates, oxalates, succinates, tartrates and tosylates are preferred as addition salts of organic acids.

Compounds in which the substitutents labelled in formula (I)

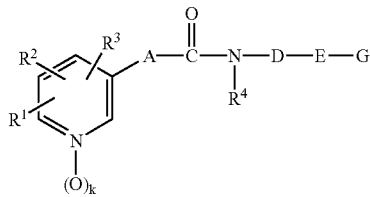

have the following meanings, are especially preferred:

$R^1$ is hydrogen, halogen, cyano, $C_1$–$C_6$-alkyl, trifluoromethyl, $C_3$–$C_8$-cycloalkyl, $C_1$–$C_4$-hydroxyalkyl, hydroxy, $C_1$–$C_4$-alkoxy, benzyloxy, $C_1$–$C_4$-alkanoyloxy, $C_1$–$C_4$-alkylthio, $C_2$–$C_5$-alkoxycarbonyl, aminocarbonyl, $C_3$–$C_9$-dialkylaminocarbonyl, carboxy, phenyl, phenoxy, pyridyloxy or $NR^5R^6$, wherein $R^5$ and $R^6$ are selected independently from each other form hydrogen and $C_1$–$C_6$-alkyl, $R^2$ is hydrogen, halogen, $C_1$–$C_6$-alkyl, trifluoromethyl or hydroxy, wherein $R^1$ and $R^2$, in the case they are adjacent, optionally form a bridge which are selected from the group of bridge members —(CH$_2$)$_4$— and —(CH═CH)$_2$— and —CH$_2$O—CR$^7$R$^8$—O—, wherein $R^7$ and $R^8$ can be, independently from each other, hydrogen and $C_1$–$C_6$-alkyl, $R^3$ is selected from hydrogen, halogen and $C_1$–$C_6$-alkyl and $R^4$ is selected from hydrogen, $C_1$–$C_6$-alkyl, $C_3$–$C_6$-alkenyl, hydroxy, $C_1$–$C_6$-alkoxy and benzyloxy, k is 0 or 1, A is $C_2$–$C_6$-alkenylene, which is optionally substituted one to three-fold by $C_1$–$C_3$-alkyl, hydroxy, fluorine, cyano, or phenyl, $C_4$–$C_6$-alkadienylene, which is optionally substituted once or twice by $C_1$–$C_3$-alkyl, fluorine, cyano, or phenyl, 1,3,5-hexatrienylene, which is optionally substituted by $C_1$–$C_3$-alkyl, fluorine, or cyano, as well as ethinylene D is selected from $C_{1-10}$-alkylene, which is optionally substituted once or twice by $C_1$–$C_3$-alkyl or hydroxy, $C_2$–$C_{10}$-alkenylene, optionally substituted once or twice by $C_1$–$C_3$-alkyl or hydroxy, wherein the double bond can also be to ring E or $C_3$–$C_{10}$-alkinylene, which is optionally substituted once or twice by $C_1$–$C_3$-alkyl or hydroxy, and can be selected as well from $C_1$–$C_{10}$-alkylene, $C_2$–$C_{10}$-alkenylene or $C_3$–$C_{10}$-alkinylene, in which one to three methylene units are isosterically replaced by O, S, NR$^9$, CO, SO or SO$_2$, wherein $R^9$ is hydrogen, $C_1$–$C_3$-alkyl, $C_1$–$C_6$-acyl or methanesulfonyl, E is

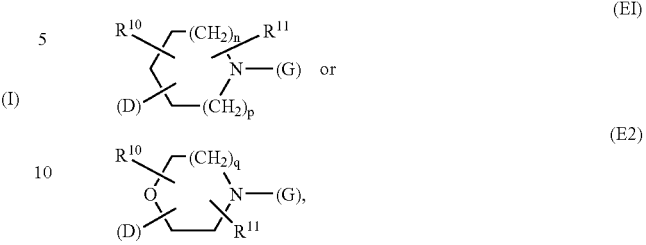

wherein the heterocyclic ring can optionally have a double bond and n and p can be, independent of each other, 0, 1, 2 or 3, with the proviso that $n+p \leq 4$, q is 2 or 3, $R^{10}$ is selected from hydrogen, $C_1$–$C_3$-alkyl, hydroxy, hydroxymethyl, carboxy or $C_2$–$C_7$-alkoxycarbonyl and $R^{11}$ is selected from hydrogen or an oxo group adjacent to the nitrogen atom, G is selected from hydrogen, G1, G2, G3, G4 and G5, wherein G1 represents the residue $$-(CH_2)_r-(CR^{13}R^{14})_s-R^{12} \qquad (G1)$$

wherein r is 0, 1 or 2 and s is 0 or 1, $R^{12}$ is selected from hydrogen, $C_1$–$C_6$-alkyl, $C_3$–$C_6$-alkenyl, $C_3$–$C_6$-alkinyl, $C_3$–$C_8$-cycloalkyl, benzyl, phenyl, monocyclic aromatic five- or six-membered heterocycles, which contain one to three hetero-atoms from the group N and/or S and/or O and are either bound directly or over a methylene group, anellated bi- and tricyclic aromatic or partially hydrated carbocyclic ring systems with 8 to 16 ring atoms and at least one aromatic ring, whereby the bond can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from the groups N and/or S and/or O and the bond can occur either over an aromatic or a hydrated ring and either directly or over a methylene group, $R^{13}$ has the same meaning as $R^{12}$, but is selected independently thereof, $R^{14}$ is selected from hydrogen, hydroxy, methyl, benzyl or phenyl, monocyclic aromatic five- or six-membered heterocycles, which can contain one to three hetero-atoms selected from the group N and/or S and/or O and are bound either directly or over a methylene group, anellated bi- and tricyclic aromatic or partially hydrated carbocyclic ring systems with 8 to 16 ring atoms and at least einem aromatic ring, wherein the bond can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from the group N and/or S and/or O and the bond can occur either over an aromatic or a hydrated ring and either directly or over a methylene group, G2 is selected from the residues

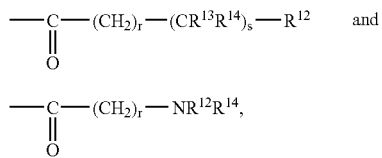

wherein the substituents $R^{12}$ and $R^{14}$ the can have the above meaning, or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from N and/or S and/or O, G3 is the residue

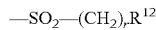

G4 is the residue

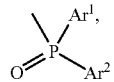

wherein $Ar^1$ and $Ar^2$ are selected independently of each other from phenyl, pyridyl or naphthyl, G5 is the residue

wherein $R^{15}$ is trifluoromethyl, $C_1$–$C_6$-alkoxy, $C_3$–$C_6$-alkenyloxy or benzyloxy and aromatic ring systems in which the substituents $R^1$, $R^2$, $R^4$, $R^{12}$, $R^{13}$, $R^{14}$, $R^{15}$, $Ar^1$ and $Ar^2$ and/or in the ring system —$NR^{12}R^{14}$ can carry independently of each other one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, which can be optionally entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino, di-($C_1$–$C_6$-alkyl)-amino, wherein two adjacent groups on the aromatic ring or ring system can form an additional ring over a methylenedioxy bridge.

Compounds in which the substituents labelled in formula (I)

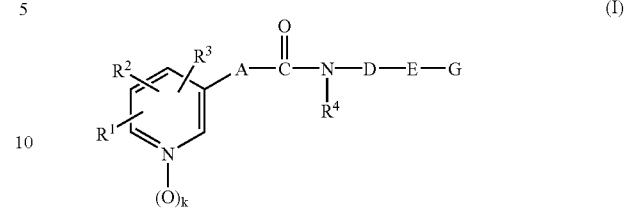

have the following meanings are particularly preferred:

$R^1$ is hydrogen, halogen, cyano, methyl, trifluoromethyl, hydroxy, $C_1$–$C_4$-alkoxy, ethylthio, methoxycarbonyl, tert-butoxycarbonyl, aminocarbonyl, carboxy, and phenoxy, $R^2$ is hydrogen, halogen, trifluoromethyl or hydroxy, $R^3$ is hydrogen or halogen, $R^4$ is selected from hydrogen, $C_1$–$C_3$-alkyl, hydroxy and $C_1$–$C_3$-alkoxy, k is 0 or 1, A is $C_2$–$C_6$-alkenylene, which is optionally substituted once or twice by $C_1$–$C_3$-alkyl, hydroxy or fluorine, or $C_4$–$C_6$-alkadienylene, which is optionally substituted by is $C_1$–$C_3$-alkyl or by 1 or 2 fluorine atoms, or 1,3,5-hexatrienylene, which is optionally substituted by fluorine, as well as D is $C_1$–$C_8$-alkylene, which is optionally substituted once twice by methyl or hydroxy, $C_2$–$C_8$-alkenylene, which is optionally substituted once or twice by methyl or hydroxy, wherein the double bond can also be to ring E, $C_3$–$C_8$-alkinylene, which is optionally substituted once or twice by methyl or hydroxy, as well as $C_1$–$C_8$-alkylene, $C_2$–$C_8$-alkenylene or $C_3$–$C_8$-alkinylene, in which one to three methylene units can be isosterically replaced by O, S, NH, N(CH$_3$), N(COCH$_3$), N(SO$_2$CH$_3$), CO, SO or SO$_2$, E is

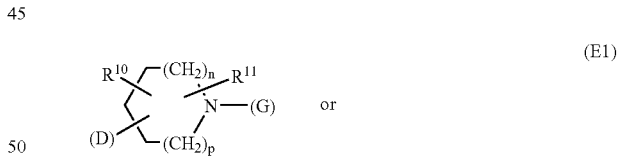

wherein the heterocyclic ring can optionally have a double bond and n and p can be independent of each other 0, 1, 2 or 3, with the proviso that n+p≦3, q is 2 or 3, $R^{10}$ is selected from hydrogen, $C_1$–$C_3$-alkyl, hydroxy, hydroxymethyl and $R^{11}$ is selected from hydrogen or an oxo group which is adjacent to the nitrogen atom, G is hydrogen or
G1, G2, G3, G4 and G5, wherein
G1 represents the residue

  (G1)

wherein
r is 0, 1 or 2 and
s is 0 or 1,
$R^{12}$ is selected from hydrogen, $C_1$–$C_6$-alkyl, $C_3$–$C_8$-cycloalkyl, benzyl or phenyl,
benzocyclobutyl, indanyl, indenyl, oxoindanyl, naphthyl, dihydronaphthyl, tetrahydronaphthyl, oxotetrahydronaphthyl, biphenylenyl, fluorenyl, oxofluorenyl, anthryl, dihydroanthryl, oxodihydroanthryl, dioxodihydroanthryl, phenanthryl, dihydrophenanthryl, oxodihydrophenanthryl, dibenzocycloheptenyl, oxodibenzocycloheptenyl, dihydrodibenzocycloheptenyl, oxodihydrodibenzocycloheptenyl, dihydrodibenzocyclooctenyl, tetrahydrodibenzocyclooctenyl and oxotetrahydrodibenzocyclooctenyl, bound directly or over a methylene group,
furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, imidazothiazolyl benzofuryl, dihydrobenzofuryl, benzothienyl, dihydrobenzothienyl, indolyl, indolinyl, oxoindolinyl, dioxoindolinyl, benzoxazolyl, oxobenzoxazolinyl, benzisoxazolyl, oxobenzisoxazolinyl, benzothiazolyl oxobenzthiazolinyl, benzoisothiazolyl, oxobenzoisothiazolinyl, benzimidazolyl, oxobenzimidazolinyl, indazolyl, oxoindazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromonyl, quinolyl, isoquinolyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenothiazinyl, dihydrodibenzoxepinyl, oxodihydrodibenzoxepinyl, benzocycloheptathienyl, oxobenzocycloheptathienyl, dihydrothienobenzothiepinyl, oxodihydrothienobenzothiepinyl dihydrodibenzothiepinyl, oxodihydrodibenzothiepinyl, octahydrodibenzothiepinyl, dihydrodibenzazepinyl, oxodihydrodibenzazepinyl, octahydrodibenzazepinyl, benzocycloheptapyridyl, oxobenzocycloheptapyridyl, dihydropyridobenzodiazepinyl, dihydrodibenzoxazepinyl, dihydropyridobenzoxepinyl, dihydropyridobenzoxazepinyl, oxodihydropyridobenzoxazepinyl, dihydrodibenzothiazepinyl, oxodihydrodibenzothiazepinyl, dihydropyridobenzothiazepinyl, oxodihydropyridobenzothiazepinyl, bound directly or over a methylene group,
$R^{13}$ has the same meaning as $R^{12}$, but is selected independently therefrom,
$R^{14}$ is selected from hydrogen, hydroxy, methyl, benzyl or phenyl,
indanyl, indenyl, naphthyl, dihydronaphthyl, tetrahydronaphthyl, furyl, thienyl, pyrrolyl, oxazolyl, isoxazolyl, thiazolyl, isothiazolyl, pyrazolyl, imidazolyl, oxadiazolyl thiadiazolyl, triazolyl, pyridyl, pyrazinyl, pyridazinyl, pyrimidinyl, triazinyl, benzofuryl, benzothienyl, indolyl, indolinyl, benzoxazolyl, benzothiazolyl, benzimidazolyl, chromanyl, quinolyl or tetrahydroquinolyl bound directly or over a methylene group, G2 is selected from the residues

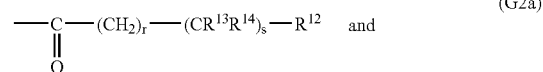  (G2a)

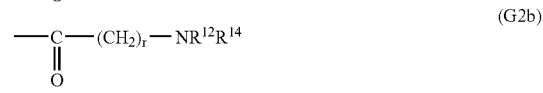  (G2b)

wherein the substituents $R^{12}$ and $R^{14}$ can have the above meanings, or represents the grouping

over the nitrogen-bound ring atom of azetidine, pyrrolidine, piperidine, (1H)tetrahydropyridine, hexahydroazepine, (1H)tetrahydroazepine, octahydroazocine, pyrazolidine, piperazine, hexyhydrodiazepine, morpholine, hexahydrooxazepine, thiomorpholine, thiomorpholine-1,1-dioxide, 5-aza-bicyclo[2.1.1]hexane, 2-aza-bicyclo[2.2.1]heptane, 7-aza-bicyclo[2.2.1]heptane, 2,5-diaza-bicyclo[2.2.1]heptane, 2-aza-bicyclo[2.2.2]octane, 8- bicyclo[3.2.1]octane, 2,5-diazabicyclo[2.2.2]octane, 9-azabicyclo[3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4b]indole, (10H)-dihydroacridine, 1,2,3,4-tetrahydroacridanone, (10H)-phenoxazine, (10H)-phenothiazine, (5H)-dibenzazepine, (5H)-dihydrodibenzazepine, (5H)-Octahydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine or (5H)-tetrahydrodibenzazocine, G3 is the residue $$—SO_2—(CH_2)_r R^{12}$$  (G3), G4 is the residue

  (G4)

wherein
$Ar^1$ and
$Ar^2$ are selected independently of each other from phenyl, pyridyl or naphthyl, G5 is the residue

  (G5)

wherein
$R^{15}$ is trifluoromethyl, $C_1$–$C_6$-alkoxy, $C_3$–$C_6$-alkenyloxy or benzyloxy and aromatic ring systems in which the substituents can be substituted independently of each other by one to three of the same or different substituents from the series halogen, cyano, $C_1$–$C_6$-alkyl, trifluoromethyl, $C_3$–$C_8$-Cycloalkyl, phenyl, benzyl, hydroxy, $C_1$–$C_6$-alkoxy, $C_1$–$C_6$-alkoxy, which can be entirely or partially substituted by fluorine, can carry benzyloxy, phenoxy, mercapto, $C_1$–$C_6$-allylthio, carboxy, $C_1$–$C_6$-alkoxycarbonyl, benzyloxycarbonyl, nitro, amino, mono-$C_1$–$C_6$-alkylamino, di-($C_1$–$C_6$-alkyl)-amino, wherein two adjacent groups can form an additional ring with a methylenedioxy bridge.

A further preferred embodiment of the invention is in compounds which are distinguished in that the labelled substituents in formula (I)

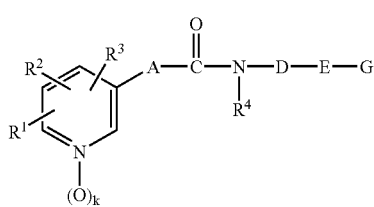
(I)

have the following meaning:

$R^1$ is hydrogen, halogen, cyano, methyl, trifluoromethyl, hydroxy, methoxy or methoxycarbonyl, $R^2$ is hydrogen or halogen, $R^3$ is hydrogen, $R^4$ is selected from hydrogen, $C_1$–$C_3$-alkyl or hydroxy, k is 0 or 1, A is selected from $C_2$–$C_6$-alkylene, which is optionally substituted once or twice by hydroxy or fluorine, or
$C_2$–$C_6$-alkenylene, which is optionally substituted once or twice by hydroxy or fluorine,
$C_4$–$C_6$-alkadienylene, which is optionally substituted by 1 or 2 fluorine atoms, or
1,3,5-hexatrienylene, D is $C_2$–$C_8$-alkylene, which is optionally substituted by methyl or hydroxy,
$C_2$–$C_8$-alkenylene, which is optionally substituted by methyl or hydroxy, wherein the double bond can also be to ring E, or
$C_2$–$C_8$-alkylene, $C_2$–$C_8$-alkenylene, wherein one to three methylene units can be isosterically replaced by O, NH, N(CH$_3$), N(COCH$_3$), N(SO$_2$CH$_3$) or CO, E is selected from the residues

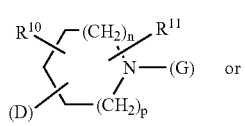
(E1)

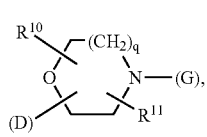
(E2)

wherein the heterocyclic ring can optionally have a double bond and n and p can be, independent of each other, 0, 1, 2 or 3, with the proviso that n+p≦3 and q is 2

$R^{10}$ is hydrogen, methyl or hydroxyl and $R^{11}$ is hydrogen or an oxo group adjacent to the nitrogen atom, G is selected from hydrogen, $C_3$–$C_8$-cycloalkyl, methoxycarbonyl, tert-butoxycarbonyl, benzyloxycarbonyl, trifluoroacetyl, diphenylphosphinoyl or the residues

—(CH$_2$)$_r$—(CR$^{13}$R$^{14}$)$_s$—R$^{12}$ (G1)

and

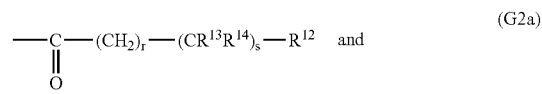
(G2a)

(G2b)

and

—SO$_2$—(CH$_2$)$_r$R$^{12}$ (G3)

wherein r is 0, 1 or 2 and s is 0 or 1, $R^{12}$ is hydrogen, methyl, benzyl or phenyl,
indanyl indenyl, oxoindanyl, naphthyl, dihydronaphthyl, tetrahydronaphthyl, oxotetrahydronaphthyl, fluorenyl, oxofluorenyl, anthryl, dihydroanthryl, oxodihydroanthryl, dioxodihydroanthryl, dibenzocycloheptenyl, oxodibenzocycloheptenyl, dihydrodibenzocycloheptenyl, oxodihydrodibenzocycloheptenyl bound directly or over a methylene group,
furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, imidazothiazolyl, benzofuryl, dihydrobenzofuryl, benzothienyl, dihydrobenzothienyl, indolyl, indolinyl, oxoindolinyl, dioxoindolinyl, benzoxazolyl, oxobenzoxazolinyl, benzisoxazolyl, oxobenzisoxazolinyl, benzothiazolyl, oxobenzthiazolinyl, benzoisothiazolyl, oxobenzoisothiazolinyl, benzimidazolyl, oxobenzimidazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, thienopyrimidinyl, chromanyl, chromanonyl, benzopyranyl, chromonyl, quinolyl, isoquinolyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenothiazinyl, dihydrodibenzoxepinyl, benzocycloheptathienyl, oxobenzocycloheptathienyl, dihydrothienobenzothiepinyl, oxodihydrothienobenzothiepinyl dihydrodibenzothiepinyl, oxodihydrodibenzothiepinyl, dihydrodibenzazepinyl, oxodihydrodibenzazepinyl, octahydrodibenzazepinyl, benzocycloheptapyridyl, oxobenzocycloheptapyridyl, dihydropyridobenzoxepinyl, dihydrodibenzothiazepinyl, oxodihydrodibenzothiazepinyl bound directly or over a methylene group, $R^{13}$ is hydrogen, methyl, benzyl or phenyl, $R^{14}$ is selected from hydrogen, hydroxy, methyl, benzyl, phenyl,
naphthyl, furyl, thienyl, oxazolyl, thiazolyl, pyrazolyl, imidazolyl, oxadiazolyl, thiadiazolyl, pyridyl, benzofuryl, benzothienyl, indolyl, indolinyl, benzoxazolyl, benzothiazolyl, benzimidazolyl, chromanyl, quinolyl or tetrahydroquinolyl, bound directly or over a methylene group, wherein in formula (I)

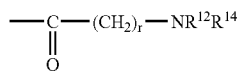
(G2b)

—$NR^{12}R^{14}$ can also be selected from pyrrolidine, piperidine, (1H)tetrahydropyridine, hexahydroazepine, Octahydroazocine, piperazine, hexahydrodiazepine, morpholine, hexahydrooxazepine, 2-azabicyclo[2.2.1]heptane, 7-azabicyclo[2.2.1]heptane, 2,5-diazabicyclo[2.2.1]heptane, 8-azabicyclo[3.2.1]octane, 2,5-diazabicyclo[2.2.2]octane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenzothiazine, (1H)tetrahydrobenzo[b]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indol, (10H)-dihydroacridine, 1,2,3,4-tetrahydroacridanone, (5H)-dihydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxaze-pine or (5H)-tetrahydrodibenzazocine.

Compounds in which the labelled substituents in formula (I)

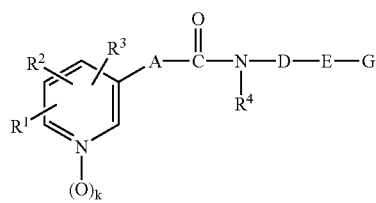
(I)

have the following meanings are very particularly preferred:
$R^1$ is hydrogen, fluorine, chlorine, bromine, methyl, trifluoromethyl or hydroxy,
$R^2$ and
$R^3$ are hydrogen,
$R^4$ is hydrogen or hydroxy,
k is 0 or 1,
A is selected from $C_2$–$C_4$-alkylene, which is optionally substituted by fluorine,
D is selected from $C_2$–$C_6$-alkylene, $C_2$–$C_6$-alkenylene, wherein the double bond can also be to ring E, and $C_2$–$C_6$-alkylene and $C_2$–$C_6$-alkenylene, wherein a methylene unit can be isosterically replaced by O, NH, N($CH_3$) or CO or an ethylene group can be isosterically replaced by NH—CO and/or CO—NH or a propylene group can be isosterically replaced by NH—CO—O and/or O—CO—NH,
E is selected from pyrrolidine, piperidine, 1,2,5,6-tetrahydropyridine, hexahydroazepine, morpholine and hexahydro-1,4-oxazepine, wherein the heterocyclic ring optionally adjacent to the nitrogen atom, can be substituted by an oxo group,
G is selected from hydrogen, tert-butoxycarbonyl, diphenylphosphinoyl, or one of the residues

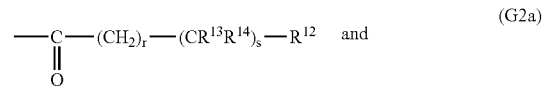
(G1)
and

(G2a)

—$C$—$(CH_2)_r$—$NR^{12}R^{14}$ (G2b)
‖
O and

—$SO_2$—$(CH_2)_r R^{12}$ (G3)

wherein
r is 0 or 1 and
s is 0 or 1,
$R^{12}$ is hydrogen, methyl, benzyl or phenyl,
indenyl, oxoindanyl, naphthyl, tetrahydronaphthyl, fluorenyl, oxofluorenyl, anthryl, dihydroanthryl, oxodihydroanthryl, dioxodihydroanthryl, dibenzocycloheptenyl, dihydrodibenzocycloheptenyl bound directly or over a methylene group,
furyl, thienyl, oxazolyl, thiazolyl, imidazolyl, oxadiazolyl, thiadiazolyl, pyridyl, pyrazinyl, pyrimidinyl, imidazothiazolyl, benzofuryl, benzothienyl, indolyl, oxoindolinyl, dioxoindolinyl, benzoxazolyl, oxobenzoxazolinyl, benzothiazolyl, oxobenzthiazolinyl, benzimidazolyl, oxobenzimidazolinyl, benzofurazanyl, benzotriazolyl, oxazolopyridyl, oxodihydrooxazolopyridyl, thiazolopyridyl, oxodihydrothiazolopyridyl, chromanyl, chromanonyl, benzopyranyl, chromonyl, quinolyl, isoquinolyl, oxodihydroquinolinyl, tetrahydroquinolyl, oxotetrahydroquinolinyl, benzodioxanyl, quinazolinyl, acridinyl, oxodihydroacridinyl, phenothiazinyl, dihydrodibenzoxepinyl, benzocycloheptathienyl, dihydrothienobenzothiepinyl, dihydrodibenzothiepinyl, oxodihydrodibenzothiepinyl, dihydrodibenzazepinyl oxodihydrodibenzazepinyl, octahydrodibenzazepinyl, benzocycloheptapyridyl, oxobenzocycloheptapyridyl, dihydrodibenzothiazepinyl bound directly or over a methylene group,
$R^{13}$ is hydrogen, methyl, benzyl or phenyl,
$R^{14}$ is hydrogen, hydroxy, methyl, benzyl or phenyl,
naphthyl, furyl, thienyl, pyridyl, benzofuryl, benzothienyl, indolyl, benzoxazolyl, benzothiazolyl, benzimidazolyl, chromanyl, quinolyl or tetrahydroquinolyl bound directly or over a methylene group, wherein in the formula

(G2b)

—$NR^{12}R^{14}$ can be selected from pyrrolidine, piperidine, hexahydroazepine, morpholine, 2,5-diazabicyclo[2.2.1]heptane, indoline, isoindoline, (1H)-dihydroquinoline, (1H)-tetrahydroquinoline, (2H)-tetrahydroisoquinoline, (1H)-tetrahydrobenzo[b]azepine, (1H)tetrahydrobenzo[d]azepine, (5H)-tetrahydrobenzo[b]oxazepine, (5H)-tetrahydrobenzo[b]thiazepine, 1,2,3,4-tetrahydroacridanone, (5H)-dihydrodibenzazepine, (11H)-dihydrodibenzo[b,e]-oxazepine or (11H)-dihydrodibenzo[b,e]thiazepine and wherein aromatic ring systems in the substituents can be substituted, independently of each other, by one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, $C_1$–$C_6$-alkoxy, which can be entirely or partially substituted by fluorine, can carry benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino, whereby two adjacent groups on the aromatic ring or ring system can form an additional ring over a methylenedioxy bridge.

Compounds are especially preferred which distinguish themselves in that the labelled substituents in formula (I)

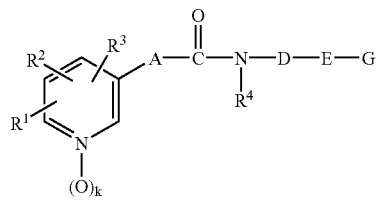

(I)

have the following meanings:
$R^1$ is hydrogen, fluorine, methyl, trifluoromethyl or hydroxy,
$R^2$ and
$R^3$ are hydrogen,
$R^4$ is hydrogen or hydroxy,
k is 0,
A is ethenylene (vinylene) or 1,3-butadienylene,
D is selected from $C_2$–$C_6$-alkylene or $C_2$–$C_6$-alkenylene, wherein the double bond can also be to ring E, E is selected from pyrrolidine, piperidine, hexahydroazepine or morpholine, G is selected from benzyl, phenethyl, fluorenylmethyl, anthrylmethyl, diphenylmethyl, fluorenyl or dihydrodibenzocycloheptenyl, furylmethyl, thienylmethyl, thiazolylmethyl, pyridylmethyl, benzothienylmethyl, quinolylmethyl, phenylthienylmethyl, phenyl-pyridylmethyl, dihydrodibenzoxepinyl, dihydrodibenzothiepinyl, acetyl, pivaloyl, phenylacetyl, diphenylacetyl, diphenylpropionyl, naphthylacetyl, benzoyl, naphthoyl, anthrylcarbonyl, oxofluorenylcarbonyl, oxodihydroanthrylcarbonyl or dioxodihydroanthrylcarbonyl, furoyl, pyridylcarbonyl, chromonylcarbonyl, quinolylcarbonyl, naphthylaminocarbonyl, dibenzylaminocarbonyl, benzylphenylaminocarbonyl, diphenylaminocarbonyl, indolinyl-1-carbonyl, dihydrodibenzazepin-N-carbonyl, tetrahydroquinolinyl-N-carbonyl, tetrahydrobenzo[b]azepinyl-N-carbonyl, methanesulfonyl, phenylsulfonyl, p-toluenesulfonyl, naphthylsulfonyl, quinolinsulfonyl and diphenylphosphinoyl, wherein aromatic ring systems can be substituted independently of each other by one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, $C_1$–$C_6$-alkoxy, which can be entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino, wherein two adjacent groups in the ring or ring system can form an additional ring over a methylendioxy bridge.

A series of exemplary compounds with the respective substituent definitions are listed in the following Table I for illustration of the invention without restricting the scope of the compounds according to the invention.

TABLE 1

Exemplifying compounds of formula (I) according to the invention

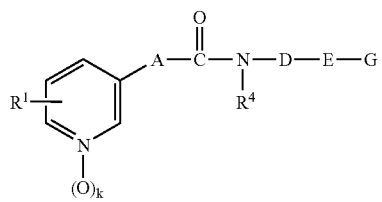

| Nr | $R^1$ | k | A | $R^4$ | D-E-G |
|---|---|---|---|---|---|
| 1 | H | 0 | CH=CH | H | 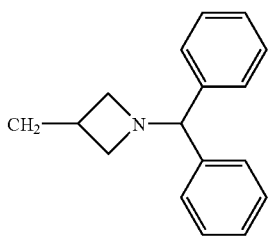 |

TABLE 1-continued
Exemplifying compounds of formula (I) according to the invention
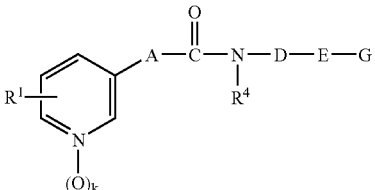
| Nr | R¹ | k | A | R⁴ | D-E-G |
|----|----|----|---|----|-------|
| 2 | H | 0 | CH=CH—CH=CH | H | 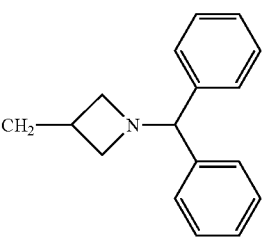 |
| 3 | H | 0 | CH=CH | H | 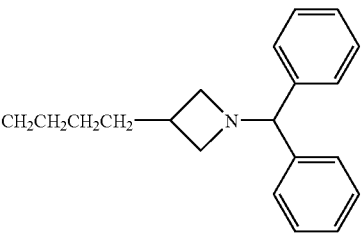 |
| 4 | H | 0 | CH=CH | H | 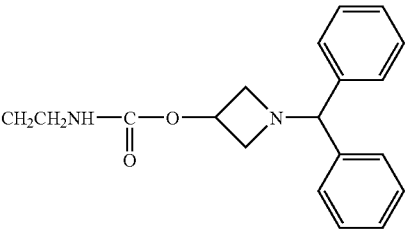 |
| 5 | H | 0 | CH=CH | H | 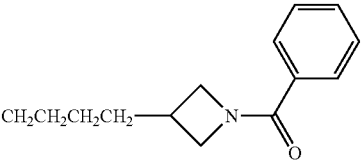 |
| 6 | H | 0 | CH=CH | H | 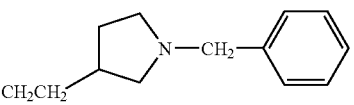 |
| 7 | H | 0 | CH=CH—CH=CH | H | 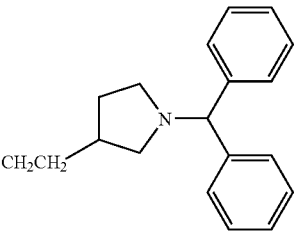 |

TABLE 1-continued
Exemplifying compounds of formula (I) according to the invention
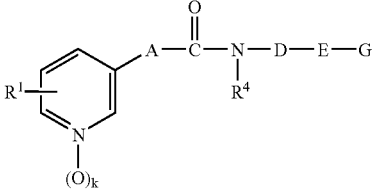
| Nr | R¹ | k | A | R⁴ | D-E-G |
|---|---|---|---|---|---|
| 8 | H | 0 | CH=CH(CH$_2$)$_2$ | H | 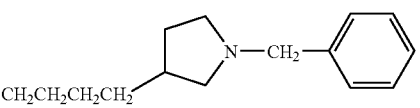 |
| 9 | H | 0 | CH=CH | H | 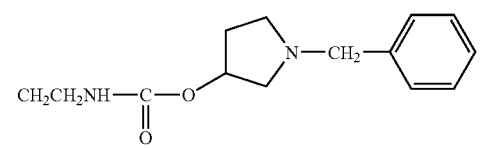 |
| 10 | H | 0 | CH=CH | H | 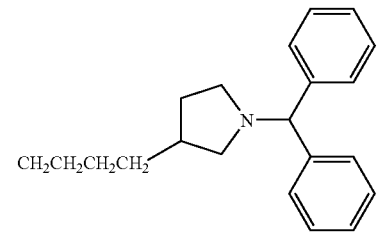 |
| 11 | H | 0 | CH=CH | H | 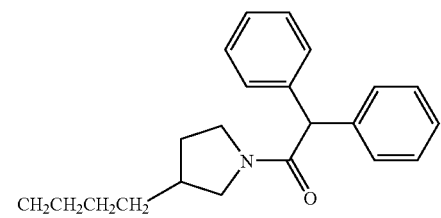 |
| 12 | H | 0 | CH=CH | H | 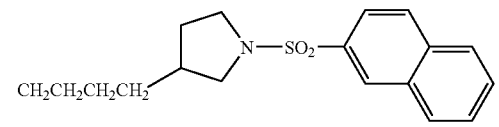 |
| 13 | H | 0 | CH=CH | H | 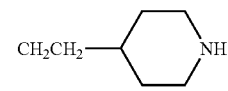 |
| 14 | H | 0 | CH=CH | H | 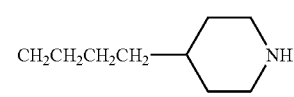 |
| 15 | H | 0 | CH=CH—CH=CH | H | 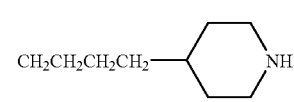 |
| 16 | H | 0 | CH=CH | H | 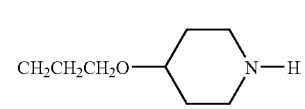 |

TABLE 1-continued

Exemplifying compounds of formula (I) according to the invention

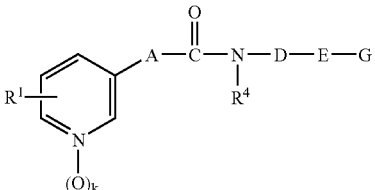

| Nr | R¹ | k | A | R⁴ | D-E-G |
|----|----|----|----|----|-------|
| 17 | H | 0 | CH=CH | H | CH₂CH₂CH₂CH₂CH₂CH₂-[piperidine]-NH |
| 18 | H | 0 | CH=CH—CH=CH | H | CH₂CH₂-[piperidine]-N—CH₃ |
| 19 | H | 0 | CH=CH—CH=CH | H | CH₂CH₂CH₂CH₂-[piperidine]-N(CH₃)₂ (isopropyl) |
| 20 | H | 0 | CH=CH(CH₂)₂ | H | CH₂CH₂CH₂CH₂-[piperidine]-N-cyclopropyl |
| 21 | H | 0 | CH=CH | H | CH₂CH₂NH—C(=O)—O-[piperidine]-N-cyclohexyl |
| 22 | H | 0 | CH=C(CN) | H | CH₂CH₂-[piperidine]-N—CH₂-cyclopropyl |
| 23 | H | 0 | CH=CH | H | (CH₂)₈-[piperidine]-N—CH₂-cyclopropyl |
| 24 | H | 0 | CH=CH | H | CH₂CH₂CH₂O-[piperidine]-N—CH₂-cyclohexyl |
| 25 | H | 0 | CH=CH | H | CH₂CH₂CH₂CH₂-[piperidine]-N—CH₂-[piperidine]-NH |
| 26 | H | 0 | CH=CH | H | CH₂CH₂CH₂CH₂-[piperidine]-N—CH₂CH₂-[piperidine]-NH |

TABLE 1-continued
Exemplifying compounds of formula (I) according to the invention
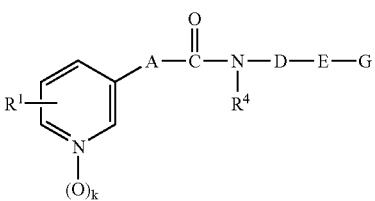
| Nr | R¹ | k | A | R⁴ | D-E-G |
|----|----|----|-----|-----|-------|
| 27 | H | 0 | CH=CH | H | 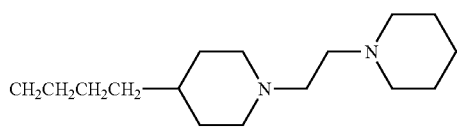 |
| 28 | H | 0 | CH=CH | h | 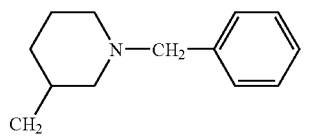 |
| 29 | H | 0 | CH=CH | H | 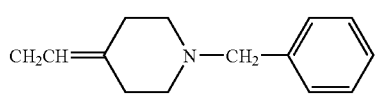 |
| 30 | H | 0 | CH=CH—CH=CH | H | 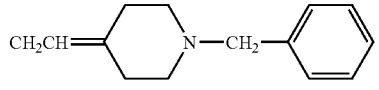 |
| 31 | H | 1 | CH=CH | H |  |
| 32 | H | 0 | CH=CH | OH | 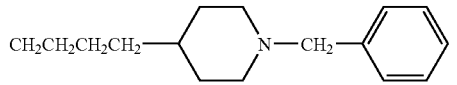 |
| 33 | H | 0 | CH=C(CN) | H |  |
| 34 | H | 0 | C≡C | H | 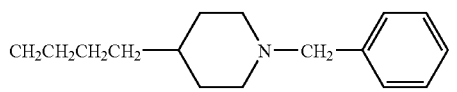 |
| 35 | H | 0 | CH=CH(CH₂)₂ | H | 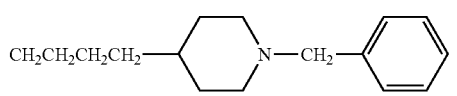 |
| 36 | H | 0 | CH=CH—CH=CH | H | 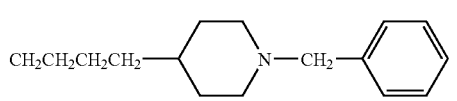 |
| 37 | 2-F | 0 | CH=CH—CH=CH | H | 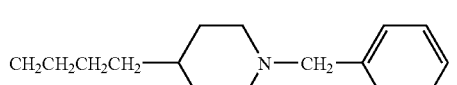 |
| 38 | H | 0 | (CH=CH)₂ | H | 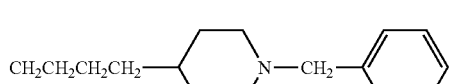 |

TABLE 1-continued
Exemplifying compounds of formula (I) according to the invention
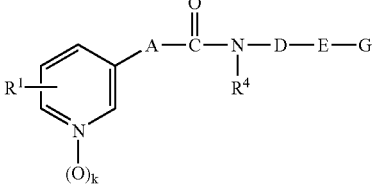
| Nr | R¹ | k | A | R⁴ | D-E-G |
|---|---|---|---|---|---|
| 39 | H | 0 | CH=CH | H | 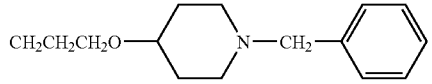 |
| 40 | H | 0 | CH=CH | H | 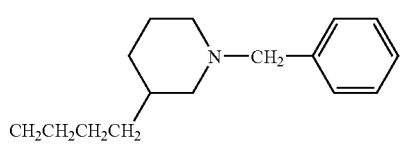 |
| 41 | H | 0 | CH=CH | H | 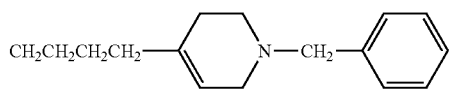 |
| 42 | H | 0 | CH=CH | H | 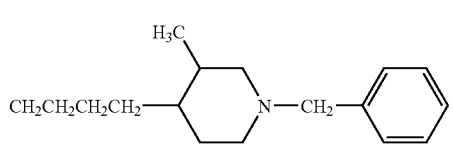 |
| 43 | H | 0 | CH=CH | H | 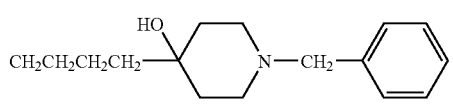 |
| 44 | H | 0 | CH=CH | H | 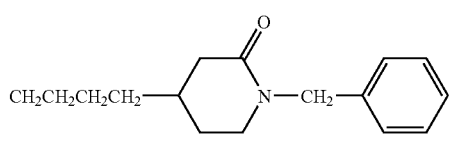 |
| 45 | H | 0 | CH=CH | H | 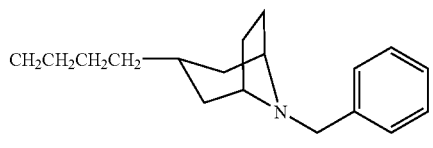 |
| 46 | H | 0 | CH=CH—CH=CH | H | 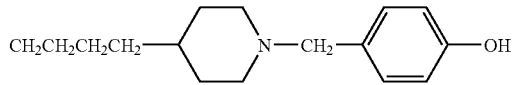 |
| 47 | H | 0 | CH=CH—CH=CH | H | 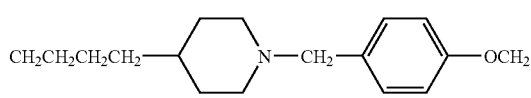 |
| 48 | H | 0 | CH=CH—CH=CH | H | 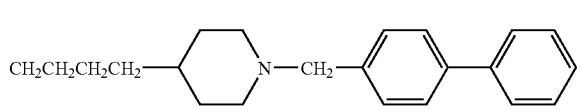 |

TABLE 1-continued
Exemplifying compounds of formula (I) according to the invention
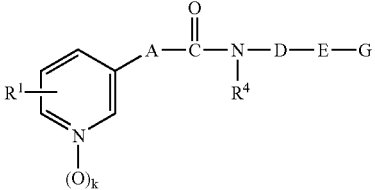
| Nr | R¹ | k | A | R⁴ | D-E-G |
|----|----|----|----|----|----|
| 49 | H | 0 | CH=CH—CH=CH | H | 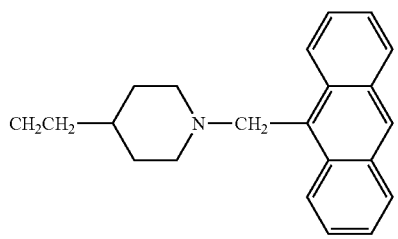 |
| 50 | H | 0 | C≡C | H | 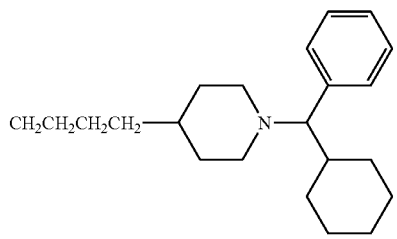 |
| 51 | H | 0 | CH=CH | H | 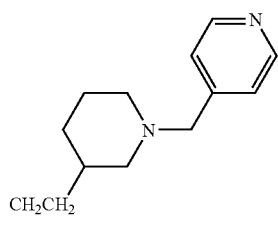 |
| 52 | H | 0 | CH=CH—CH=CH | H | 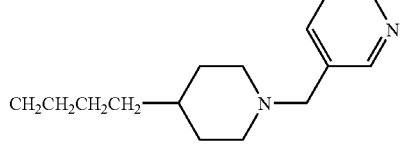 |
| 53 | H | 0 | CH=CH | H | 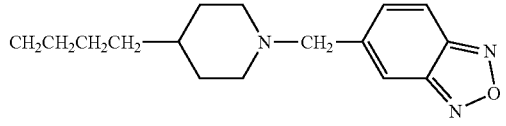 |
| 54 | H | 0 | CH=CH | H | CH₂—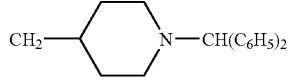—CH(C₆H₅)₂ |
| 55 | H | 0 | CH=CH—CH=CH | H | CH₂—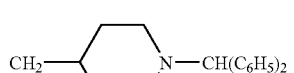—CH(C₆H₅)₂ |
| 56 | H | 1 | CH=CH | H | CH₂CH₂—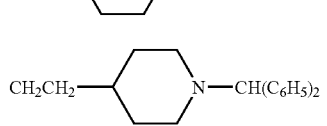—CH(C₆H₅)₂ |

TABLE 1-continued

Exemplifying compounds of formula (I) according to the invention

| Nr | R¹ | k | A | R⁴ | D-E-G |
|---|---|---|---|---|---|
| 57 | H | 0 | CH=CH(CH$_2$)$_2$ | H | CH$_2$CH$_2$-[piperidine]-N-CH(C$_6$H$_5$)$_2$ |
| 58 | H | 0 | CH=CHCH$_2$CHF | H | CH$_2$CH$_2$-[piperidine]-N-CH(C$_6$H$_5$)$_2$ |
| 59 | H | 0 | CH=CH | H | NH-C(=O)-[piperidine]-N-CH(C$_6$H$_5$)$_2$ |
| 60 | H | 0 | CH=CH | H | [piperidine with 3-CH$_2$CH$_2$]-N-CH(C$_6$H$_5$)$_2$ |
| 61 | H | 0 | CH=CH—CH=CH | H | CH$_2$CH$_2$CH$_2$-[piperidine]-N-CH(C$_6$H$_5$)$_2$ |
| 62 | H | 0 | CH=CH | H | CH$_2$CH$_2$NH-[piperidine]-N-CH(C$_6$H$_5$)$_2$ |
| 63 | H | 1 | CH=CH | H | CH$_2$CH$_2$CH$_2$CH$_2$-[piperidine]-N-CH(C$_6$H$_5$)$_2$ |
| 64 | H | 0 | CH=CH | OH | CH$_2$CH$_2$CH$_2$CH$_2$-[piperidine]-N-CH(C$_6$H$_5$)$_2$ |
| 65 | H | 0 | CH=C(CN) | H | CH$_2$CH$_2$CH$_2$CH$_2$-[piperidine]-N-CH(C$_6$H$_5$)$_2$ |
| 66 | H | 0 | C≡C | H | CH$_2$CH$_2$CH$_2$CH$_2$-[piperidine]-N-CH(C$_6$H$_5$)$_2$ |
| 67 | H | 0 | CH=CH(CH$_2$)$_2$ | H | CH$_2$CH$_2$CH$_2$CH$_2$-[piperidine]-N-CH(C$_6$H$_5$)$_2$ |
| 68 | H | 0 | CH=CHCH(OH)CF$_2$ | H | CH$_2$CH$_2$CH$_2$CH$_2$-[piperidine]-N-CH(C$_6$H$_5$)$_2$ |

TABLE 1-continued

Exemplifying compounds of formula (I) according to the invention

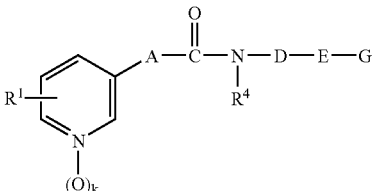

| Nr | R¹ | k | A | R⁴ | D-E-G |
|----|----|----|---|-----|-------|
| 69 | H | 0 | (CH$_2$)$_2$CH=CH | H | CH$_2$CH$_2$CH$_2$CH$_2$—[piperidine]N—CH(C$_6$H$_5$)$_2$ |
| 70 | H | 0 | CH=CH—CH=CH | H | CH$_2$CH$_2$CH$_2$CH$_2$—[piperidine]N—CH(C$_6$H$_5$)$_2$ |
| 71 | H | 0 | CH=CH—CH=CH | CH$_3$ | CH$_2$CH$_2$CH$_2$CH$_2$—[piperidine]N—CH(C$_6$H$_5$)$_2$ |
| 72 | 2-F | 0 | CH=CH—CH=CH | H | CH$_2$CH$_2$CH$_2$CH$_2$—[piperidine]N—CH(C$_6$H$_5$)$_2$ |
| 73 | 2-F | 0 | CH=CH—CH=CH | OH | CH$_2$CH$_2$CH$_2$CH$_2$—[piperidine]N—CH(C$_6$H$_5$)$_2$ |
| 74 | 4-F | 0 | CH=CH—CH=CH | H | CH$_2$CH$_2$CH$_2$CH$_2$—[piperidine]N—CH(C$_6$H$_5$)$_2$ |
| 75 | 5-F | 0 | CH=CH—CH=CH | H | CH$_2$CH$_2$CH$_2$CH$_2$—[piperidine]N—CH(C$_6$H$_5$)$_2$ |
| 76 | 6-F | 0 | CH=CH—CH=CH | H | CH$_2$CH$_2$CH$_2$CH$_2$—[piperidine]N—CH(C$_6$H$_5$)$_2$ |
| 77 | 2-Cl | 0 | CH=CH—CH=CH | H | CH$_2$CH$_2$CH$_2$CH$_2$—[piperidine]N—CH(C$_6$H$_5$)$_2$ |
| 78 | 6-CH$_3$ | 0 | CH=CH—CH=CH | H | CH$_2$CH$_2$CH$_2$CH$_2$—[piperidine]N—CH(C$_6$H$_5$)$_2$ |
| 79 | 2-OH | 0 | CH=CH—CH=CH | H | CH$_2$CH$_2$CH$_2$CH$_2$—[piperidine]N—CH(C$_6$H$_5$)$_2$ |
| 80 | H | 0 | (CH=CH)$_3$ | H | CH$_2$CH$_2$CH$_2$CH$_2$—[piperidine]N—CH(C$_6$H$_5$)$_2$ |
| 81 | H | 0 | CH=CH | H | [3-substituted piperidine] N—CH(C$_6$H$_5$)$_2$, with CH$_2$CH$_2$CH$_2$CH$_2$ |

TABLE 1-continued
Exemplifying compounds of formula (I) according to the invention
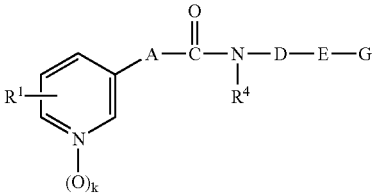
| Nr | R¹ | k | A | R⁴ | D-E-G |
|----|------|---|------------|----|-------|
| 82 | 2-F | 0 | CH=CH | H | 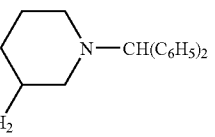 |
| 83 | 5-F | 0 | CH=CH | H | 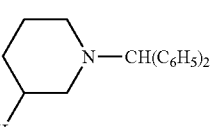 |
| 84 | 6-CH₃O | 0 | CH=CH | H | 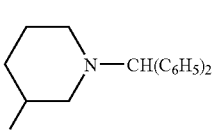 |
| 85 | H | 0 | CH=CH—CH=CH | H | 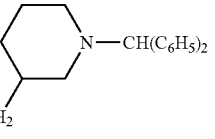 |
| 86 | H | 0 | CH=CH | H | 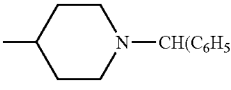 |
| 87 | H | 0 | CH=CH—CH=CH | H | 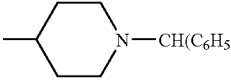 |
| 88 | H | 0 | CH=CH | H | 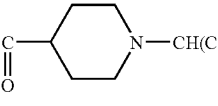 |
| 89 | H | 0 | CH=CH | H | 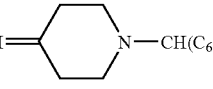 |
| 90 | H | 0 | CH=CH | H | 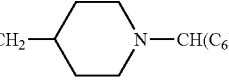 |
| 91 | H | 0 | CH=CH | H | 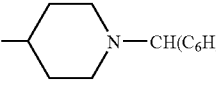 |
| 92 | H | 0 | CH=CH | H | 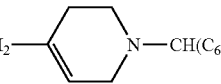 |

TABLE 1-continued

Exemplifying compounds of formula (I) according to the invention

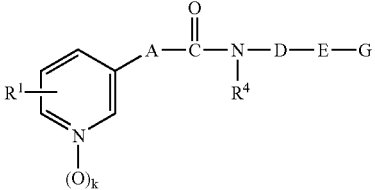

| Nr | R¹ | k | A | R⁴ | D-E-G |
|---|---|---|---|---|---|
| 93 | H | 0 | CH=CH—CH=CH | H | CH₂CH₂CH₂CH₂CH₂—[piperidine]—N—CH(C₆H₅)₂ |
| 94 | H | 0 | CH=CH | H | CH₂CH₂CH₂OCH₂—[piperidine]—N—CH(C₆H₅)₂ |
| 95 | H | 0 | CH=CH—CH=CH | H | CH₂CH₂CH₂OCH₂—[piperidine]—N—CH(C₆H₅)₂ |
| 96 | H | 0 | CH=CH | H | OCH₂CH₂CH₂—[piperidine]—N—CH(C₆H₅)₂ |
| 97 | H | 0 | CH=CH | H | CH₂CH₂NH—C(=O)—O—[piperidine]—N—CH(C₆H₅)₂ |
| 98 | H | 0 | CH=CH—CH=CH | H | CH₂CH₂CH₂CH₂CH₂CH₂—[piperidine]—N—CH(C₆H₅)₂ |
| 99 | H | 0 | CH=CH | H | CH₂CH₂CH₂OCH₂CH₂—[piperidine]—N—CH(C₆H₅)₂ |
| 100 | H | 0 | CH=CH | H | CH₂CH₂CH₂CH₂NH—C(=O)—[piperidine]—N—CH(C₆H₅)₂ |
| 101 | H | 0 | CH=CH | H | (CH₂)₇—[piperidine]—N—CH(C₆H₅)₂ |
| 102 | H | 0 | CH=CH | H | (CH₂)₈—[piperidine]—N—CH(C₆H₅)₂ |
| 103 | H | 0 | CH=CH | H | (CH₂)₆NH—C(=O)—[piperidine]—N—CH(C₆H₅)₂ |

TABLE 1-continued
Exemplifying compounds of formula (I) according to the invention
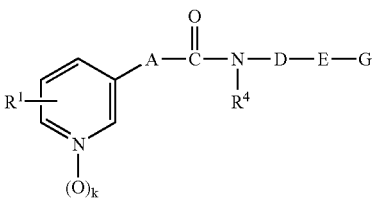
| Nr | R¹ | k | A | R⁴ | D-E-G |
|----|----|----|-----|-----|-------|
| 104 | H | 0 | CH=CH | H | 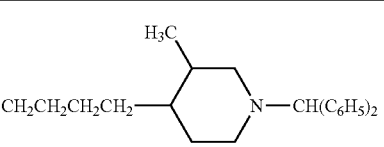 |
| 105 | H | 0 | CH=CH | H | 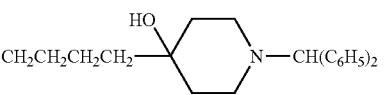 |
| 106 | H | 0 | CH=CH | H | 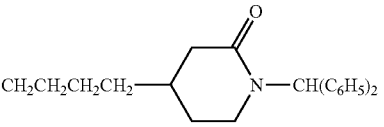 |
| 107 | H | 0 | CH=CH | H | 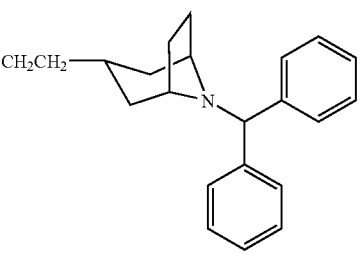 |
| 108 | H | 0 | CH=CH | H | 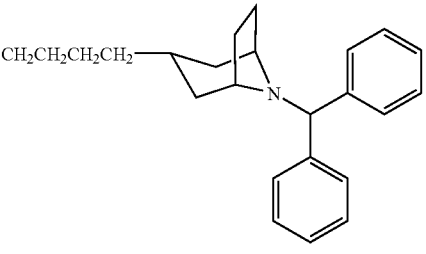 |
| 109 | H | 0 | CH=CH—CH=CH | H | 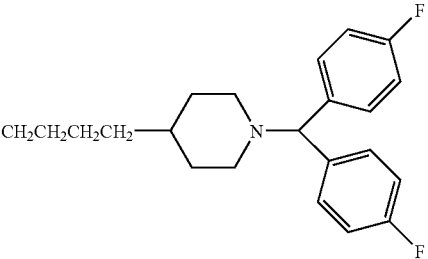 |

TABLE 1-continued
Exemplifying compounds of formula (I) according to the invention
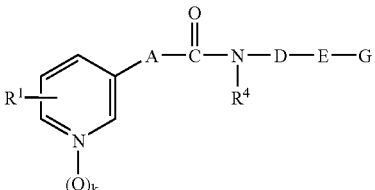
| Nr | R¹ | k | A | R⁴ | D-E-G |
|---|---|---|---|---|---|
| 110 | H | 0 | C≡C | H | 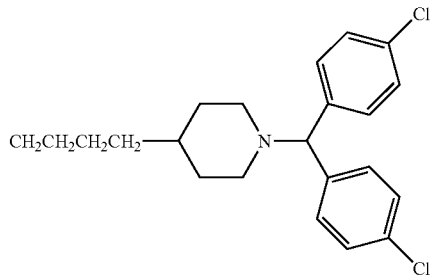 |
| 111 | H | 0 | CH=CH—CH=CH | H | 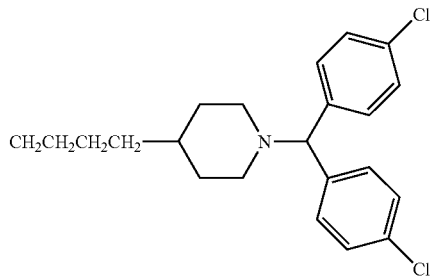 |
| 112 | H | 0 | C≡C | H | 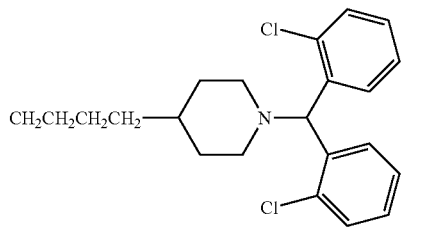 |
| 113 | H | 0 | (CH$_2$)$_2$CH=CH | H | 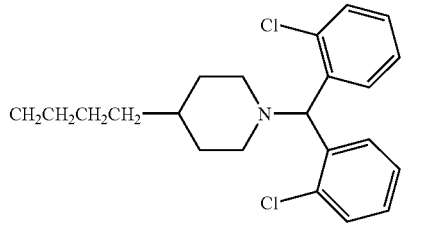 |
| 114 | H | 0 | CH=CH—CH=CH | H | 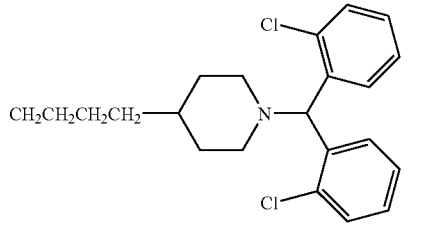 |

TABLE 1-continued
Exemplifying compounds of formula (I) according to the invention
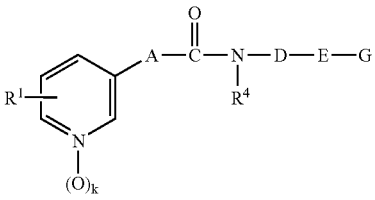
| Nr | R¹ | k | A | R⁴ | D-E-G |
|----|----|----|----|----|----|
| 115 | H | 0 | CH=CH—CH=CH | H | 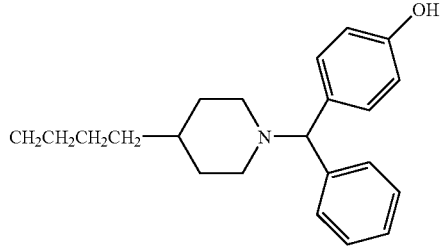 |
| 116 | H | 0 | CH=CH—CH=CH | H | 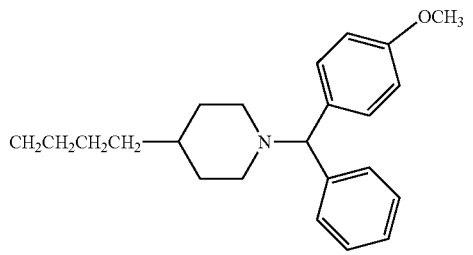 |
| 117 | H | 0 | CH=CH—CH=CH | H | 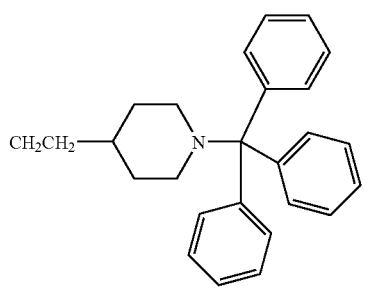 |
| 118 | H | 0 | CH=CH—CH=CH | H | 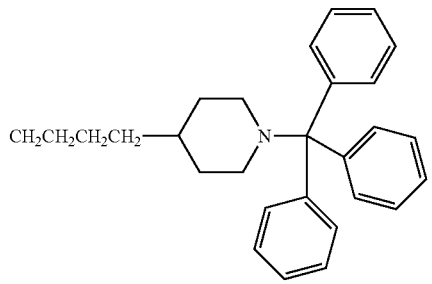 |

TABLE 1-continued
Exemplifying compounds of formula (I) according to the invention
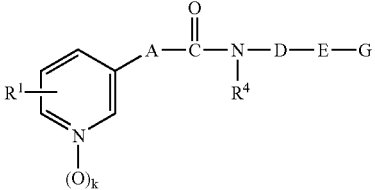
| Nr | R¹ | k | A | R⁴ | D-E-G |
|----|----|----|----|----|----|
| 119 | H | 0 | CH=CH | H | 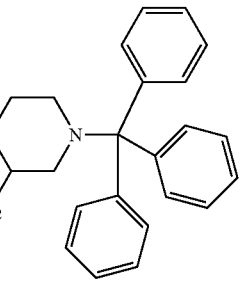 |
| 120 | H | 0 | CH=CH—CH=CH | H | 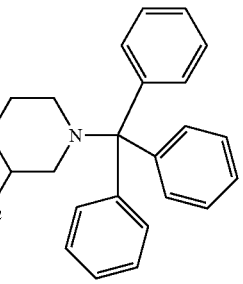 |
| 121 | H | 0 | CH=CH | H | 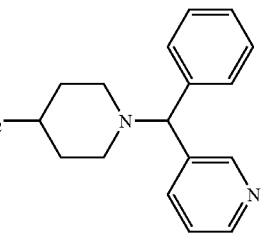 |
| 122 | H | 0 | CH=CH—CH=CH | H | 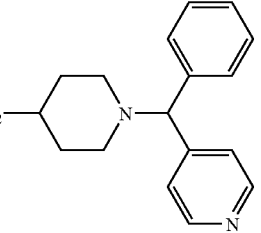 |
| 123 | H | 0 | CH=CH | H | 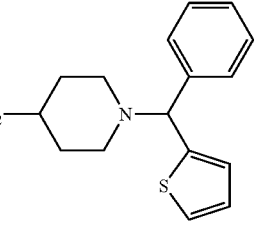 |

TABLE 1-continued

Exemplifying compounds of formula (I) according to the invention

| Nr | R¹ | k | A | R⁴ | D-E-G |
|---|---|---|---|---|---|
| 124 | H | 0 | CH=CH—CH=CH | H | CH₂CH₂—[4-piperidinyl]-N-(9H-fluoren-9-yl) |
| 125 | H | 0 | CH=C(CN) | H | CH₂CH₂CH₂CH₂—[4-piperidinyl]-N-(9H-fluoren-9-yl) |
| 126 | H | 0 | CH=CH—CH=CH | H | CH₂CH₂CH₂CH₂—[4-piperidinyl]-N-(9H-fluoren-9-yl) |
| 127 | H | 0 | CH=CHCH₂CHF | H | CH₂CH₂CH₂CH₂—[4-piperidinyl]-N-(10,11-dihydro-5H-dibenzo[a,d]cyclohepten-5-yl) |
| 128 | H | 0 | CH=CH—CH=CH | H | CH₂CH₂CH₂CH₂—[4-piperidinyl]-N-(10,11-dihydro-5H-dibenzo[a,d]cyclohepten-5-yl) |

TABLE 1-continued
Exemplifying compounds of formula (I) according to the invention
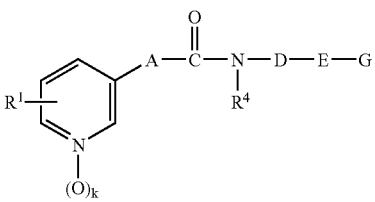
| Nr | R¹ | k | A | R⁴ | D-E-G |
|----|----|----|---|----|-------|
| 129 | H | 0 | C≡C | H | 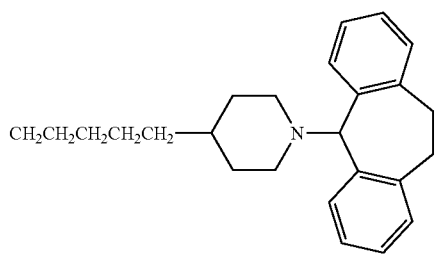 |
| 130 | H | 0 | CH=CH | H | 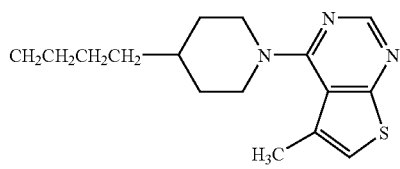 |
| 131 | H | 0 | CH=CH—CH=CH | H | 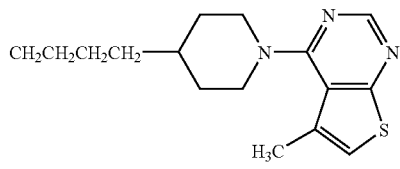 |
| 132 | H | 0 | CH=CH | H | 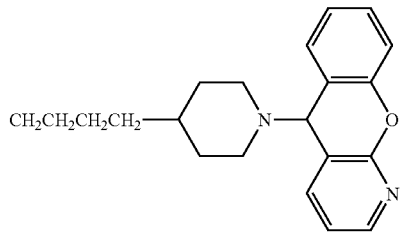 |
| 133 | H | 0 | CH=CH | H | 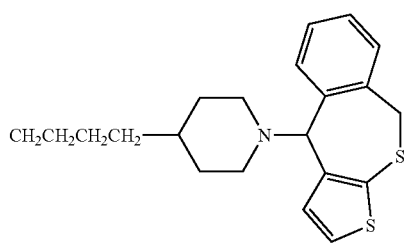 |

TABLE 1-continued

Exemplifying compounds of formula (I) according to the invention

| Nr | R¹ | k | A | R⁴ | D-E-G |
|---|---|---|---|---|---|
| 134 | H | 0 | CH=CH | H | CH₂CH₂CH₂-piperidine-N-(6,11-dihydrodibenz[b,e]oxepin-11-yl) |
| 135 | H | 0 | CH=CH—CH=CH | H | CH₂CH₂CH₂-piperidine-N-(6,11-dihydrodibenz[b,e]oxepin-11-yl) |
| 136 | H | 0 | CH=CH | H | CH₂CH₂CH₂-piperidine-N-(6,11-dihydrodibenzo[b,e]thiepin-11-yl) |
| 137 | H | 0 | CH=CH—CH=CH | H | CH₂CH₂CH₂-piperidine-N-(6,11-dihydrodibenzo[b,e]thiepin-11-yl) |
| 138 | H | 0 | CH=CH | H | CH₂CH₂-(1-acetylpiperidin-4-yl) |
| 139 | H | 0 | CH=CH—CH=CH | H | CH₂CH₂-(1-acetylpiperidin-4-yl) |

TABLE 1-continued

Exemplifying compounds of formula (I) according to the invention

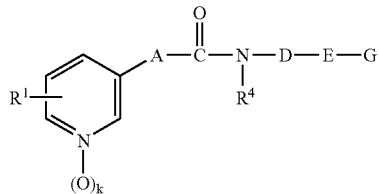

| Nr | R¹ | k | A | R⁴ | D-E-G |
|---|---|---|---|---|---|
| 140 | H | 0 | CH=CH | H | CH₂CH₂CH₂CH₂-piperidine-N-C(O)CH₃ |
| 141 | H | 0 | CH=CH—CH=CH | H | CH₂CH₂CH₂CH₂-piperidine-N-C(O)CH₃ |
| 142 | H | 0 | CH=CH | H | CH₂CH₂CH₂CH₂CH₂-*piperidine-N-C(O)CH₃ |
| 143 | H | 0 | CH=CH | H | CH₂CH₂CH₂CH₂-piperidine-N-C(O)C(CH₃)₃ |
| 144 | H | 0 | CH=CH | H | CH₂CH₂CH₂CH₂-piperidine-N-C(O)-cyclopropyl |
| 145 | H | 0 | CH=CH—CH=CH | H | CH₂CH₂CH₂CH₂-piperidine-N-C(O)-cyclopropyl |
| 146 | H | 0 | CH=CH | H | CH₂CH₂-piperidine-N-C(O)CH₂-phenyl |
| 147 | H | 0 | CH=CH | H | CH₂CH₂CH₂CH₂-piperidine-N-C(O)CH₂-phenyl |
| 148 | H | 0 | CH=CH—CH=CH | H | CH₂CH₂CH₂CH₂-piperidine-N-C(O)CH₂-phenyl |

TABLE 1-continued
Exemplifying compounds of formula (I) according to the invention
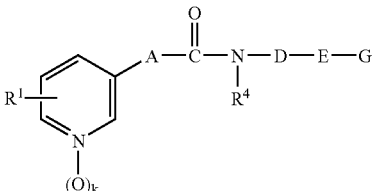
| Nr | R¹ | k | A | R⁴ | D-E-G |
|---|---|---|---|---|---|
| 149 | H | 0 | CH=CH(CH$_2$)$_2$ | H | 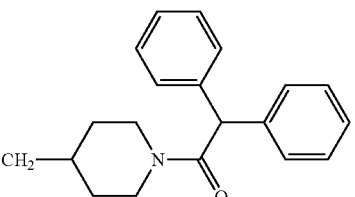 |
| 150 | H | 0 | CH=CH | H | 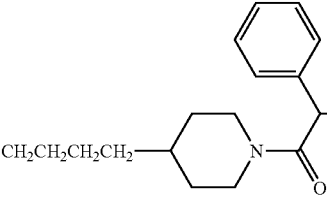 |
| 151 | H | 0 | CH=CH—CH=CH | H | 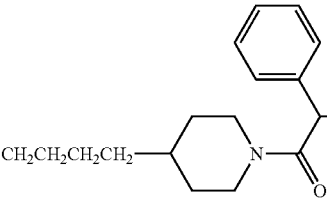 |
| 152 | H | 0 | CH=CH | H | 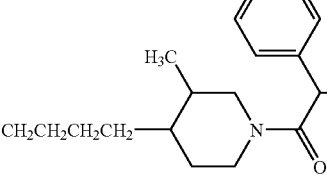 |
| 153 | H | 0 | CH=CH | H | 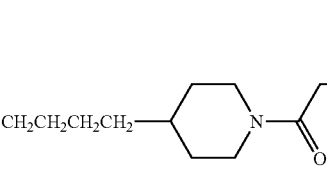 |
| 154 | H | 0 | CH=CH—CH=CH | H | 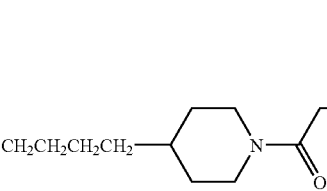 |

TABLE 1-continued
Exemplifying compounds of formula (I) according to the invention
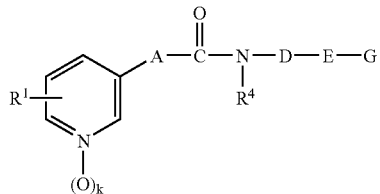
| Nr | R¹ | k | A | R⁴ | D-E-G |
|----|----|----|------|----|-------|
| 155 | H | 0 | CH=CH | H | |
| 156 | H | 0 | CH=CH | H | |
| 157 | H | 0 | CH=CH—CH=CH | H | |
| 158 | H | 0 | CH=CH | H | |
| 159 | H | 0 | CH=CH | H | |
| 160 | H | 0 | CH=C(CH₃) | H | |

TABLE 1-continued
Exemplifying compounds of formula (I) according to the invention
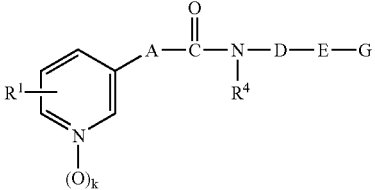
| Nr | R¹ | k | A | R⁴ | D-E-G |
|---|---|---|---|---|---|
| 161 | H | 0 | CH=CHCHCHF<br>          \|<br>          OH | H | 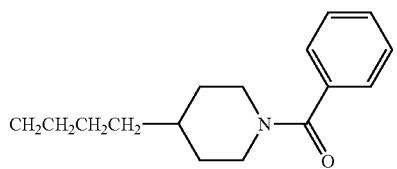 |
| 162 | H | 0 | CH=CH—CH=CH | H | 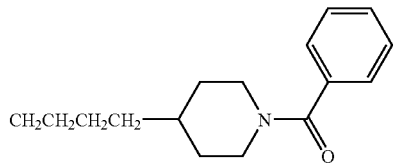 |
| 163 | H | 0 | CH=CH | H | 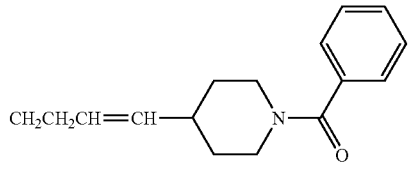 |
| 164 | H | 0 | CH=CH | CH₃ | 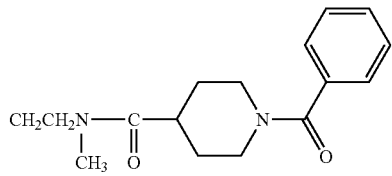 |
| 165 | H | 0 | CH=CH | H | 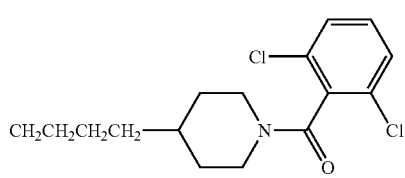 |
| 166 | H | 0 | CH=CH | H | 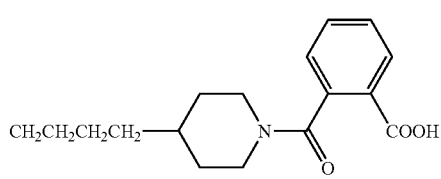 |
| 167 | H | 0 | CH=CH | H | 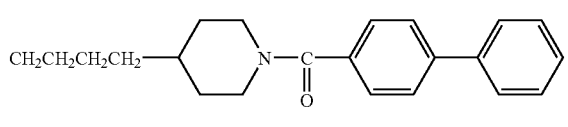 |
| 168 | H | 0 | CH=CH—CH=CH | H | 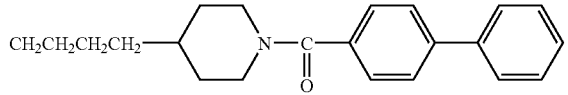 |

TABLE 1-continued
Exemplifying compounds of formula (I) according to the invention
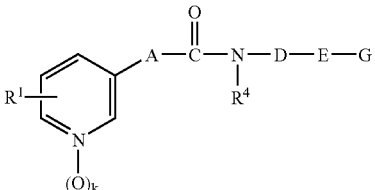
| Nr | R¹ | k | A | R⁴ | D-E-G |
|---|---|---|---|---|---|
| 169 | H | 0 | CH=CH | H | 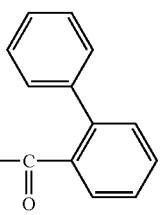 |
| 170 | H | 0 | (CH₂)₂CH=CH | H | 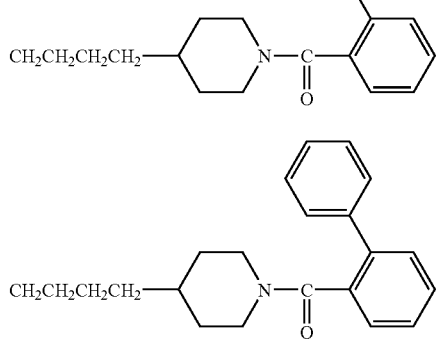 |
| 171 | H | 0 | CH=CH | H | 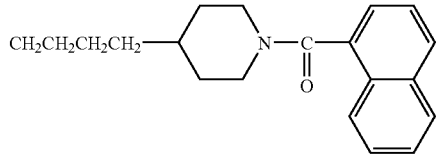 |
| 172 | 2-F | 0 | CH=CH | H | 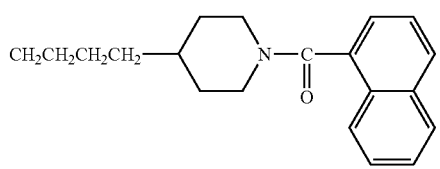 |
| 173 | H | 0 | CH=CH—CH=CH | H | 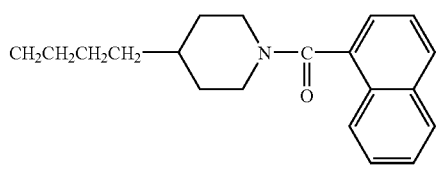 |
| 174 | H | 0 | CH=CH | H | 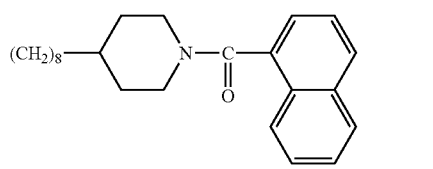 |
| 175 | H | 0 | CH=CH | H | 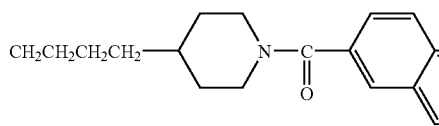 |

TABLE 1-continued

Exemplifying compounds of formula (I) according to the invention

| Nr | R¹ | k | A | R⁴ | D-E-G |
|---|---|---|---|---|---|
| 176 | H | 0 | CH=CH—CH=CH | H | CH₂CH₂CH₂-piperidine-N-C(O)-2-naphthyl |
| 177 | H | 0 | CH=CH | H | CH₂CH₂-piperidine-N-C(O)-(9-oxofluoren-4-yl) |
| 178 | H | 0 | CH=CH | H | CH₂CH₂CH₂-piperidine-N-C(O)-(9-oxofluoren-4-yl) |
| 179 | H | 0 | CH=CH—CH=CH | H | CH₂CH₂CH₂CH₂-piperidine-N-C(O)-(9-oxofluoren-4-yl) |
| 180 | H | 0 | CH=CH | H | (CH₂)₆-piperidine-N-C(O)-(9-oxofluoren-4-yl) |
| 181 | H | 0 | CH=CH | H | CH₂CH₂CH₂CH₂-piperidine-N-C(O)-(9,10-dioxoanthracen-2-yl) |
| 182 | 4-F | 0 | CH=CH | H | CH₂CH₂CH₂CH₂-piperidine-N-C(O)-(9,10-dioxoanthracen-2-yl) |

TABLE 1-continued
Exemplifying compounds of formula (I) according to the invention
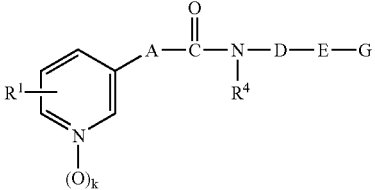
| Nr | R¹ | k | A | R⁴ | D-E-G |
|---|---|---|---|---|---|
| 183 | H | 0 | CH=CH—CH=CH | H | |
| 184 | H | 0 | CH=CH | H | |
| 185 | H | 0 | CH=CH | H | |
| 186 | H | 0 | (CH=CH)$_3$ | H | |
| 187 | H | 0 | CH=CH | H | |
| 188 | H | 0 | CH=CH—CH=CH | H | |
| 189 | H | 0 | CH=CH | H | |
| 190 | H | 0 | C≡C | H | |

TABLE 1-continued
Exemplifying compounds of formula (I) according to the invention
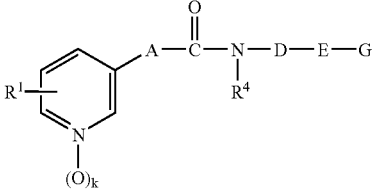
| Nr | R¹ | k | A | R⁴ | D-E-G |
|---|---|---|---|---|---|
| 191 | H | 0 | CH=CH | H | 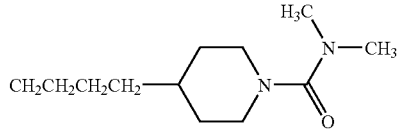 |
| 192 | H | 0 | CH=CH | H | 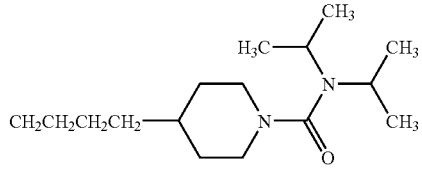 |
| 193 | H | 0 | CH=CH | H | 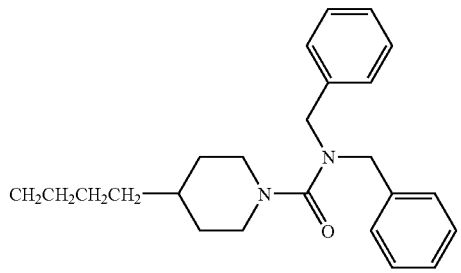 |
| 194 | H | 0 | CH=CH—CH=CH | H | 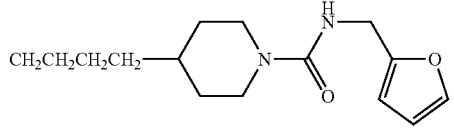 |
| 195 | H | 0 | CH=CH | H | 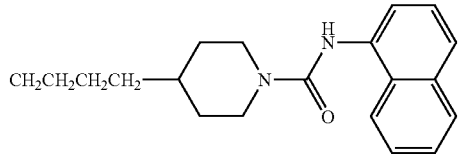 |
| 196 | 2-Cl | 0 | CH=CH | H | 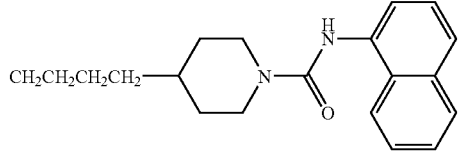 |
| 197 | H | 0 | CH=CH | H | 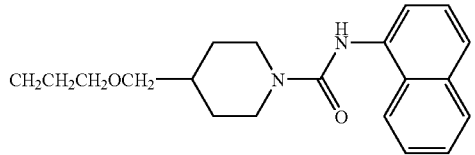 |

TABLE 1-continued
Exemplifying compounds of formula (I) according to the invention
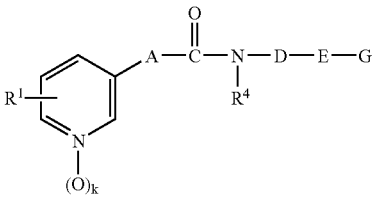
| Nr | R¹ | k | A | R⁴ | D-E-G |
|---|---|---|---|---|---|
| 198 | H | 0 | CH=CH | H | 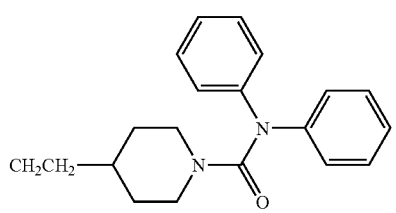 |
| 199 | H | 0 | CH=CH | H | 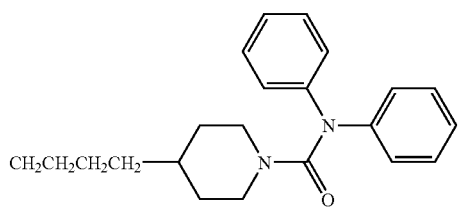 |
| 200 | H | 0 | CH=CH—CH=CH | H | 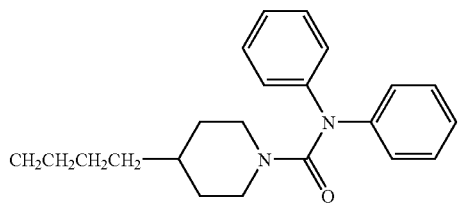 |
| 201 | H | 0 | CH=CH | H | 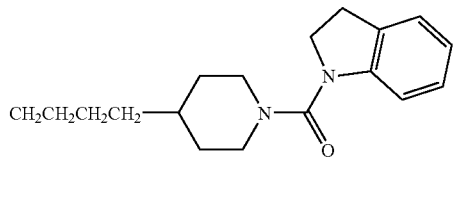 |
| 202 | H | 0 | CH=CH—CH=CH | H | 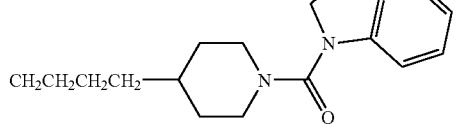 |
| 203 | H | 0 | CH=CH | H | 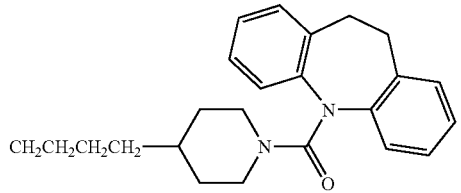 |

TABLE 1-continued
Exemplifying compounds of formula (I) according to the invention
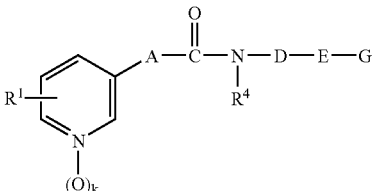
| Nr | R¹ | k | A | R⁴ | D-E-G |
|---|---|---|---|---|---|
| 204 | H | 0 | CH=CH—CH=CH | H | 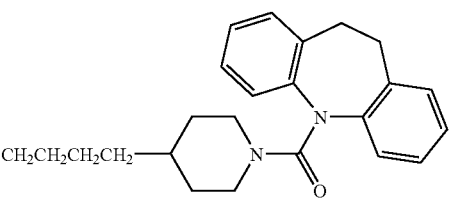 |
| 205 | H | 0 | CH=CH | H | 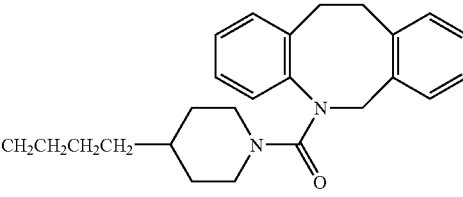 |
| 206 | H | 0 | CH=CH—CH=CH | H | 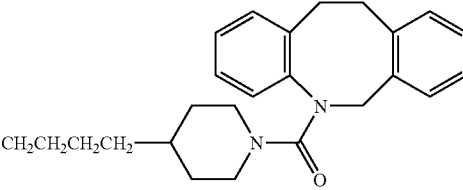 |
| 207 | H | 0 | CH=CH | H | 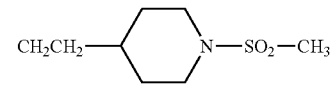 |
| 208 | H | 0 | CH=CH | H | 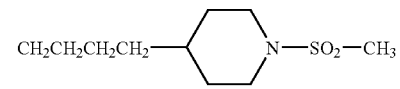 |
| 209 | H | 0 | CH=CH—CH=CH | H | 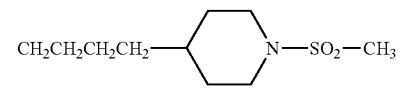 |
| 210 | H | 0 | CH=CH | H | 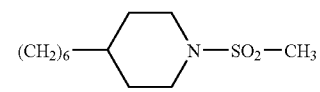 |
| 211 | H | 0 | CH=CH | H | 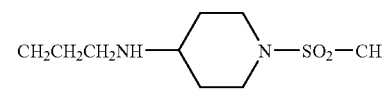 |
| 212 | H | 0 | CH=CH | H | 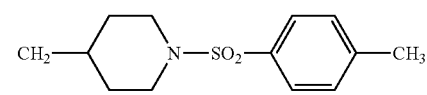 |
| 213 | H | 0 | CH=CH | H | 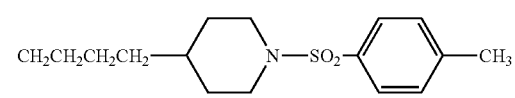 |

TABLE 1-continued
Exemplifying compounds of formula (I) according to the invention
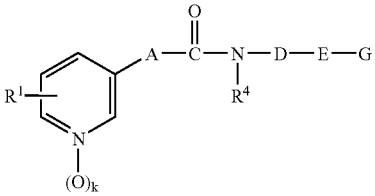
| Nr | R¹ | k | A | R⁴ | D-E-G |
|----|----|----|-----|----|-------|
| 214 | H | 0 | CH=CH—CH=CH | H | 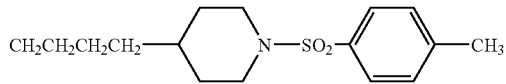 |
| 215 | H | 0 | CH=CH | H | 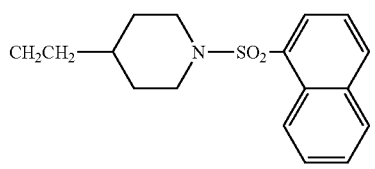 |
| 216 | H | 0 | CH=CH | H | 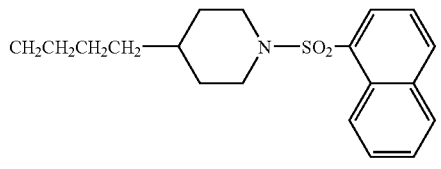 |
| 217 | H | 0 | CH=CH | H | 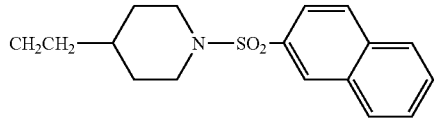 |
| 218 | H | 0 | CH=CH—CH=CH | H | 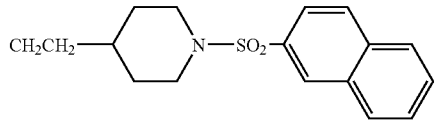 |
| 219 | H | 0 | CH=CH | H | 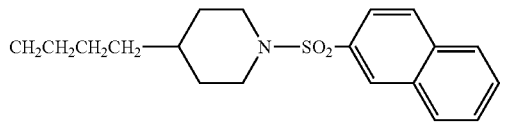 |
| 220 | H | 0 | C≡C | H | 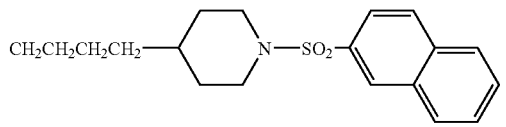 |
| 221 | H | 0 | (CH₂)₂CH=CH | H | 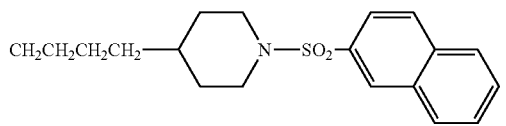 |
| 222 | H | 0 | CH=CH—CH=CH | H | 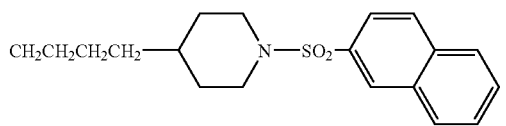 |

TABLE 1-continued

Exemplifying compounds of formula (I) according to the invention

| Nr | R¹ | k | A | R⁴ | D-E-G |
|----|----|----|----|----|----|
| 223 | H | 0 | CH=CH | H | -(CH₂)₅-piperidine-N-SO₂-naphthyl |
| 224 | H | 0 | CH=CH | H | -(CH₂)₈-piperidine-N-SO₂-thiophene |
| 225 | H | 0 | CH=CH | H | -CH₂CH₂CH₂CH₂-piperidine-N-SO₂-(6-chloroimidazo[2,1-b]thiazol-5-yl) |
| 226 | H | 0 | CH=CH—CH=CH | H | -CH₂CH₂CH₂CH₂-piperidine-N-SO₂-(6-chloroimidazo[2,1-b]thiazol-5-yl) |
| 227 | H | 0 | CH=CH | H | -CH₂CH₂CH₂CH₂-piperidine-N-SO₂-(benzo[1,2,5]oxadiazol-4-yl) |
| 228 | H | 0 | CH=CH | H | -CH₂CH₂-piperidine-N-SO₂-(5-chloro-3-methylbenzothiophen-2-yl) |
| 229 | H | 0 | CH=CH | H | -CH₂CH₂CH₂CH₂-piperidine-N-SO₂-(5-chloro-3-methylbenzothiophen-2-yl) |
| 230 | H | 0 | CH=CH—CH=CH | H | -CH₂CH₂CH₂CH₂-piperidine-N-SO₂-(5-chloro-3-methylbenzothiophen-2-yl) |

TABLE 1-continued

Exemplifying compounds of formula (I) according to the invention

| Nr | R¹ | k | A | R⁴ | D-E-G |
|---|---|---|---|---|---|
| 231 | H | 0 | CH=CH | H | CH₂CH₂CH₂CH₂-piperidine-N-SO₂-(8-quinolinyl) |
| 232 | H | 0 | CH=CH | H | CH₂CH₂CH₂CH₂-piperidine-N-P(=O)(phenyl)₂ |
| 233 | H | 0 | CH=CH—CH=CH | H | CH₂CH₂CH₂CH₂-piperidine-N-P(=O)(phenyl)₂ |
| 234 | H | 0 | CH=CH | H | (CH₂)₆-piperidine-N-P(=O)(phenyl)₂ |
| 235 | H | 0 | CH=CH | H | CH₂CH₂CH₂CH₂-piperidine-N-C(=O)CF₃ |
| 236 | H | 0 | CH=CH—CH=CH | H | CH₂CH₂CH₂CH₂-piperidine-N-C(=O)CF₃ |
| 237 | H | 0 | CH=CH | H | CH₂CH₂CH₂CH₂-piperidine-N-C(=O)OCH₃ |
| 238 | H | 0 | CH=CH—CH=CH | H | CH₂CH₂CH₂CH₂-piperidine-N-C(=O)OCH₃ |

TABLE 1-continued

Exemplifying compounds of formula (I) according to the invention

| Nr | R¹ | k | A | R⁴ | D-E-G |
|---|---|---|---|---|---|
| 239 | H | 0 | CH=CH | H | CH₂CH₂CH₂CH₂—piperidine—C(=O)—O—CH₂CH=CH₂ |
| 240 | H | 0 | CH=CH | H | CH₂CH₂—piperidine—C(=O)—O—C(CH₃)₃ |
| 241 | H | 0 | CH=CH—CH=CH | H | CH₂CH₂—piperidine—C(=O)—O—C(CH₃)₃ |
| 242 | H | 0 | CH=CH | H | CH₂CH₂CH₂CH₂—piperidine—C(=O)—O—C(CH₃)₃ |
| 243 | H | 0 | CH=CH—CH=CH | H | CH₂CH₂CH₂CH₂—piperidine—C(=O)—O—C(CH₃)₃ |
| 244 | H | 0 | C≡C | H | CH₂CH₂CH₂CH₂—piperidine—C(=O)—O—C(CH₃)₃ |
| 245 | H | 0 | (CH=CH)₃ | H | CH₂CH₂CH₂CH₂—piperidine—C(=O)—O—C(CH₃)₃ |
| 246 | H | 0 | CH=CH | H | CH₂CH₂CH₂CH—piperidine—C(=O)—O—C(CH₃)₃ |
| 247 | H | 0 | CH=CH | H | CH₂CH=CHCH₂—piperidine—C(=O)—O—C(CH₃)₃ |

TABLE 1-continued
Exemplifying compounds of formula (I) according to the invention
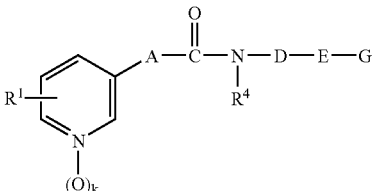
| Nr | R¹ | k | A | R⁴ | D-E-G |
|----|----|----|----|----|-------|
| 248 | H | 0 | CH=CH | H | 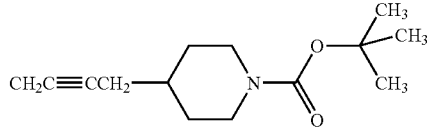 |
| 249 | H | 0 | CH=CH | H | 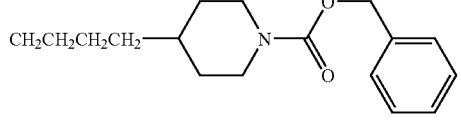 |
| 250 | H | 0 | CH=CH | H | 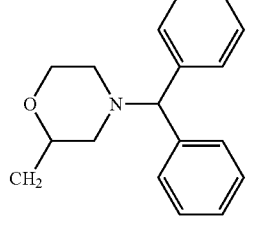 |
| 251 | H | 0 | CH=CH—CH=CH | H | 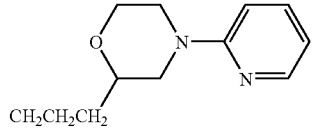 |
| 252 | H | 0 | CH=CH | H | 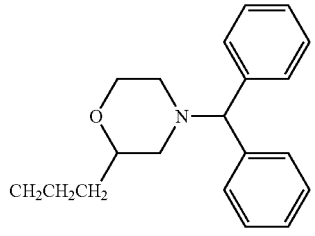 |
| 253 | H | 0 | CH=CH | H | 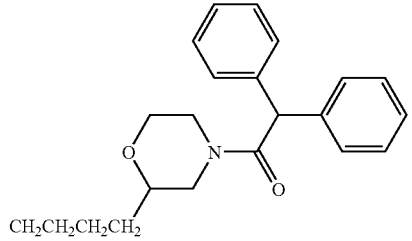 |
| 254 | H | 0 | CH=CH | H | 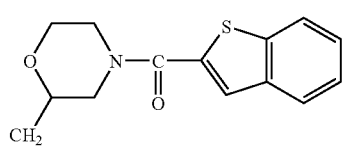 |

TABLE 1-continued
Exemplifying compounds of formula (I) according to the invention
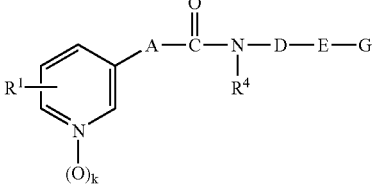
| Nr | R¹ | k | A | R⁴ | D-E-G |
|----|----|---|---|----|-------|
| 255 | H | 0 | CH=CH—CH=CH | H | 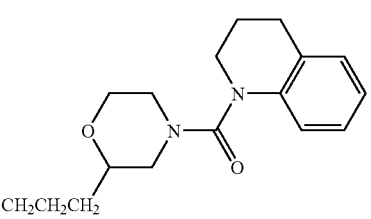 |
| 256 | H | 0 | CH=CH | H | 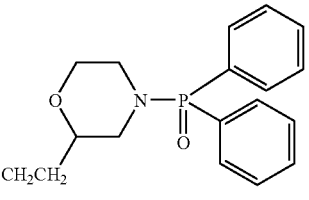 |
| 257 | H | 0 | CH=CH—CH=CH | H | 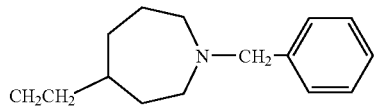 |
| 258 | H | 0 | CH=CH | H | 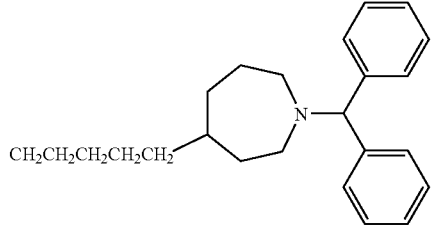 |
| 259 | H | 0 | CH=CH | H | 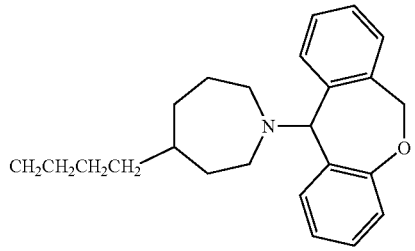 |
| 260 | H | 0 | CH=CH | H | 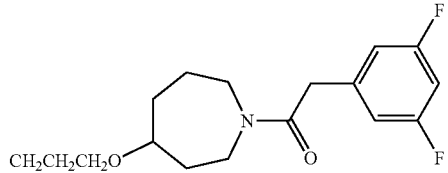 |

TABLE 1-continued
Exemplifying compounds of formula (I) according to the invention
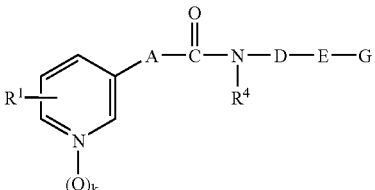
| Nr | R¹ | k | A | R⁴ | D-E-G |
|---|---|---|---|---|---|
| 261 | H | 0 | CH=CH—CH=CH | H | 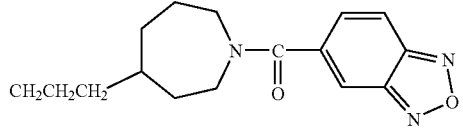 |
| 262 | H | 0 | C≡C | H | 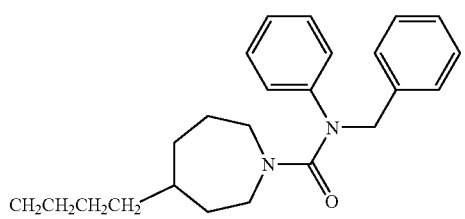 |
| 263 | H | 0 | CH=CH | H | 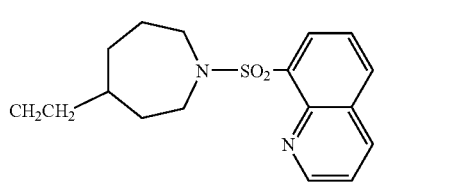 |
| 264 | H | 0 | CH=CH | H | 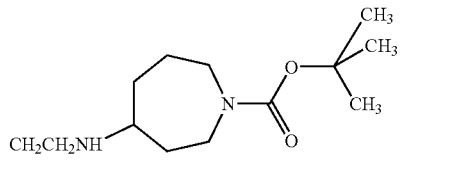 |
| 265 | H | 0 | CH=CH | H | 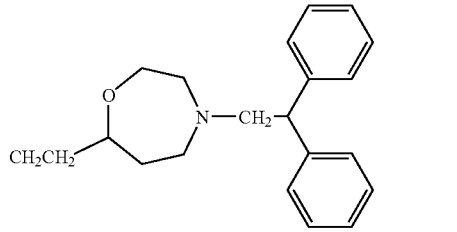 |
| 266 | H | 0 | CH=CH | H | 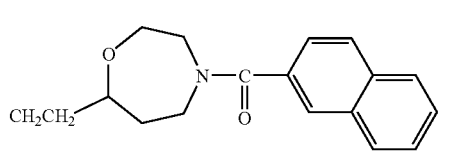 |
| 267 | H | 0 | CH=CH | H | 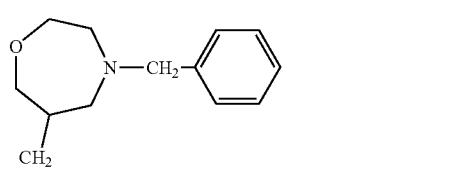 |

TABLE 1-continued

Exemplifying compounds of formula (I) according to the invention

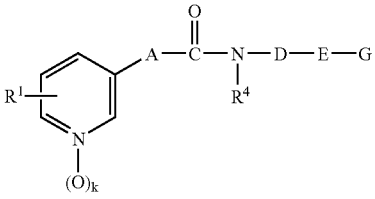

| Nr | R$^1$ | k | A | R$^4$ | D-E-G |
|---|---|---|---|---|---|
| 268 | H | 0 | CH=CH—CH=CH | H | 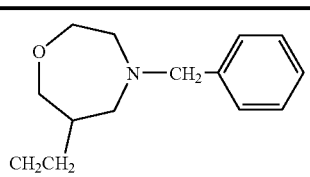 |

SYNTHESIS METHODS

Further subject-matter of the invention are analogous methods for the production of the compounds of formula (I) according to the invention.

Method (A):

Compounds of formula (I) are (a) obtained by reacting carboxylic acids of formula (II)

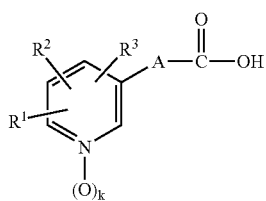

(II)

in which R$^1$, R$^2$, R$^3$, A and k have the meaning described above or their reactive derivatives are reacted with compounds of formula (III)

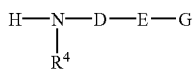

(III)

wherein D, E, G and R$^4$ also have the above described meanings.

Reactive derivatives of compound (II) can be, for example, activated esters, anhydrides, acid halides (especially acid chlorides) or simple low alkyl esters. Suitable activated esters are, for example, p-nitrophenyl ester, 2,4,6-trichlorphenyl ester, pentachlorophenyl ester, cyanomethyl ester, esters of N-hydroxysuccinimide, of N-hydroxyphthalimides, of 1-hydroxybenzotriazol, of N-hydroxypiperidine, of 2-hydroxypyridine or of 2-mercaptopyridine, etc. Anhydrides can be symmetric anhydrides or mixed, as they are obtained, for example, with pivaloyl chloride or with chloroformates. Aromatic (for example chloroformic phenyl ester), aralphatic (for example chloroformic benzyl ester) or aliphatic chloroformates (for example chloroformic methyl ester, ethyl ester or -isobutyl ester) can be used for this.

Reaction of compounds (II) with compounds (III) can also be carried out in the presence of condensation agents such as dicyclohexylcarbodiimide, 1-ethyl-3-(3-dimethylaminopropyl)carbodiimide hydrochloride, N,N'-carbonyldiimidazol, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazol, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrobromides or sulfates.

Reaction of compounds (11) or their reactive derivatives with compounds (III) are normally carried out in a suitable, preferably inert solvent. As examples, aromatic hydrocarbons such as benzene, toluene, xylene, halogenated hydrocarbons (for example dichloromethane, chloroform, 1,2-dichloroethane, trichloroethylene), ether (for example diethyl ether, tetrahydrofuran, dioxane, glycol dimethyl ether), ethyl acetate, acetonitrile or polar aprotic solvents such as, for example, dimethylsulfoxide, dimethylformamide or N-methylpyrrolidone are to be named. Pure solvents, as well as mixtures of two or more, can be used.

The reaction is optionally carried out in the presence of an auxiliary base. Suitable examples for this are alkali metal carbonates (sodium carbonate, potassium carbonate), alkali metal hydrogen carbonates (sodium hydrogen carbonate, potassium hydrogen carbonate), or organic bases such as, for example, triethylamine, ethyl diisopropylamine, tributylamine, N-methylmorpholine or pyridine. A suitable excess of compound (III) can also be used as a base. If compounds (III) are used in form of their acid addition salts, then it is appropriate to consider the amount of auxiliary base used as equivalent.

The reaction temperatures can—depending on reactivity of the educts—vary in a wide range. Generally, the reaction is carried out at temperatures between −40° C. and 180° C., preferably between −10° C. and 130° C., especially at the boiling point of the solvent used.

The starting compounds (II) and (III) are known and/or can be produced according to known methods in an analogous manner. Moreover, the production of representative examples is further described below.

Compounds of formula (I) can be (b) produced by reaction of compounds of formula (I), wherein G is hydrogen, and which themselves also have the activities found according to the invention, with a compound of formula (IV), $$L\text{—}G \quad (IV)$$

in which G has the meaning given above, with the exception of hydrogen, and L represents a suitable nucleofuge or reactive group. The type of nucleofuge or reactive group L and the conditions of the reaction are dependent of the nature of group G.

Compounds of formula (I), in which G, with the exception of hydrogen, has the meaning of (G1) according to the above definition can, aside from method (a), also be (c) produced by reacting compounds of formula (I), in which G is hydrogen, with a suitable alkylation agent and/or arylation agent of formula (IV), wherein G is an alkyl-, alkenyl-, alkinyl-, cycloalkyl-, aryl-, aralkyl-, heteroaryl- or heteroaralkyl residue and the leaving group L can represent a reactive derivative of an alcohol for example, a halogen atom such as chlorine, bromine or iodine or a sulfonic acid ester, i.e. for example a methanesulfonyloxy-, trifluoromethanesulfonyloxy-, ethanesulfonyloxy-, benzenesulfonyloxy-, p-toluenesulfonyloxy-, p-bromobenzenesulfonyloxy- or m-nitro-benzenesulfonyloxy residue, etc. or a reactive group L can also be an epoxide group, wherein the reaction occurs under addition.

The reaction of compounds (I), in which G is a hydrogen, and (IV) is usually conducted in a suitably inert solvent. As solvents of this type, aromatic hydrocarbons (benzene, toluene, xylene), ethers (for example tetrahydrofuran, dioxane, glycol dimethyl ether), ethyl acetate, acetonitrile, ketones (acetone, ethyl methyl ketone), polar protic solvents such as alcohols (ethanol, isopropanol, butanol, glycol monomethyl ether) or polar aprotic solvents such as, for example, dimethylsulfoxide, dimethylformamide or N-methylpyrrolidone can be considered. Pure solvents as well as mixtures of two or more can also be used. Preferably, the reactions are carried out in the presence of bases, whereby said bases can be used as in method (a) above. If chlorides or bromides are used as compound (IV), the reaction can be accelerated by the addition of alkali metal iodides (sodium iodide, potassium iodide). The reaction temperatures can vary between 0° C. and 180° C. depending on the reactivity of the educts, but preferably lie between 20° C. and 130° C.

Compounds of formula (I), in which G represents an acyl residue, a carbamoyl residue, a sulfonyl residue or a phosphinoyl residue according to the above definition, can also be produced, aside from the above method (a), (d) by reacting compounds of formula (I), wherein G is hydrogen, with a carboxylic acid, carbamic acid, sulfonic acid and/or phosphinic acid of formula (V), $$HO\text{—}G \quad (V)$$

wherein G is an acyl residue, carbamoyl residue, sulfonyl residue or phosphinoyl residue according to definition, or their derivatives capable of reaction. Preferred derivatives of carboxylic acids and/or sulfonic acids (V) which are capable of reaction are symmetric or unsymmetric carboxylic acid anhydrides and/or sulfonic acid anhydrides or acyl- and/or sulfonyl halides, especially acyl- and/or sulfonyl chlorides.

Preferably, derivatives of carbamates and/or phosphinic acids which are capable of reaction are the carbamoyl halides and/or phosphinyl halides, especially carbamyl-and/or phosphinyl chlorides. The reaction of the acids (V) and/or their reactive derivatives with compounds (I), in which G is hydrogen, preferably occurs in the presence of auxiliary bases in solvents and under conditions as they are described in method (a).

Compounds of formula (I), wherein G represents a carbamoyl residue according to the definition (G2b) with the proviso that r=0, the grouping is $$\text{—}\underset{\underset{O}{\|}}{C}\text{—}NR^{12}R^{14}$$

can also be produced, aside from the methods (a) and (d)

(e) by reacting compounds of formula (I), in which G is hydrogen with a carbonyl group transmitter to an intermediate product and subsequently reacting this directly with a primary or secondary amine with the formula (VI)

$$H\text{—}NR^{12}R^{14} \quad (VI)$$

wherein $R^{12}$ and $R^{14}$ and/or the grouping $\text{—}N^{12}R^{14}$ have the meanings according to the above definitions without having to purify or isolate the intermediate product.

Bis-trichloromethyl carbonate (triphosgene) and carbonyldiimidazol have been proven as particularly reactive carbonyl group transmitters. The reaction of compounds of formula (I), wherein G is hydrogen, with triphosgene and/or carbonyldiimidazol are typically conducted in an absolute, inert solvent in the presence of a tertiary organic amine as an auxiliary base in such a manner that the solution of compounds (I) and the auxiliary base are slowly poured into a solution of an equivalent amount of carbonyl group transmitter. Thereby, the reaction requires molar ratios of 1:1 for the reaction of compound (I) and carbonyldiimidazol, and, in contrast, a ratio of 1:0.35 for the use of triphosgene. After complete reaction of the components to the intermediate product, compound (VI) is added in stoichiometric amounts or in excess as a solution or a solid and the reaction is typically completed at elevated temperature. Suitable inert solvents are, for example hydrocarbons such as hexane, heptane, benzene, toluene, xylene, chlorinated hydrocarbons (for example dichloromethane, chloroform, 1,2-dichloroethane, trichloroethylene), ethers (for example diethyl ether, tetrahydrofuran, dioxane), esters such as ethyl acetate, butyl acetate, acetonitrile or polar aprodic solvents such as formamide or dimethylformamide. Pure solvents as well as mixtures can be used diversely. Sometimes it is of advantage to carry out the first partial reaction at low temperature in a low-viscosity, highly-volatile solvent and to remove the solvent after formation of the intermediate and replace it by a higher boiling solvent.

Amines such as for example triethylamine, ethyl diisopropylamine, tributylamine, N-methylmorpholine or pyridine are suitable as auxiliary bases. If compounds (I) or (VI) are used as salts, the amount of the auxiliary base is increased accordingly. The reaction temperatures can lie in between −40° C. and 50° C. for the first partial reaction, preferably at 0° C. to 30° C., and between 0° C. and 150° C. for the second partial reaction, preferably at 20° C. to 120° C.

Compounds of formula (I), wherein G represents a carbamoyl residue according to the definition (G2b) with the proviso that r=0 and $R^{14}$=hydrogen, the grouping is

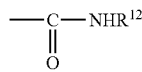

can also be produced, aside from methods (a), (d) and (e)

(f) by reacting the compounds of formula (I) in which G is hydrogen, with an isocyanate of formula (VII) in which $R^{12}$ has the meaning according to the above definition $$O=C=N-R^{12} \qquad (VII).$$

Reaction of the compounds of formula (I), in which G is hydrogen, with the isocyanates of formula (VII) are conducted thereby in an absolute, inert solvent which can be a hydrocarbon such as pentane, hexane, heptane, benzene, toluene, or xylene, chlorinated hydrocarbons (such as dichloromethane, chloroform, 1,2-dichloroethane, trichloroethylene), ethers (for example, diethyl ether, tetrahydrofuran, dioxane), esters such as ethyl acetate, butyl acetate, or polar aprotic solvents such as formamide or dimethylformamide mixtures of various solvents can also be used. Thereby, the reaction temperatures can vary in the region from −20° C. to 150° C., but preferably lie at 20° C. to 100° C.

As already mentioned, the compounds of formula (I), wherein G is hydrogen, are themselves compounds with tumor growth inhibiting activity and/or cytostatic and immunosuppressive effectiveness. However, independent of their therapeutic applicability, they also represent useful intermediate compounds for the production of a multitude of other compounds according to the invention corresponding to (c) to (f).

They themselves can, in principle, be produced according to method A by reacting a carboxylic acid of formula (II) with amines of formula (III) in which G is hydrogen as described above. However, since the compounds of formula (III) with hydrogen as G represent α,ω-diamines, the formation of product mixtures is always to be expected in their reaction with carboxylic acids (II) or their reactive derivatives making a subsequent separation necessary.

In contrast, compounds of formula (I), in which G is hydrogen, are essentially more advantageously produced from other compounds of formula (I), in which G is a selectively cleavable group under mild conditions, i.e. corresponds to a nitrogen protective group.

Among the compounds according to formula (I) with tumor growth inhibiting and/or cytostatic or immunomodulatory and/or immunosuppressive properties, are compounds in which G represents a 4-methoxybenzyl group, a triphenylmethyl group, a methoxy- and/or ethoxycarbonyl group, a tert-butoxycarbonyl group, an allyloxycarbonyl group or a trifluoroacetyl group. Thus, compounds of formula (I) with a 4-methoxybenzyl group as G are transformed into compounds of formula (I) with hydrogen as 0 by selective oxidation with ammonium-cer(IV)-nitrate for example. The cleavage of simple alkoxycarbonyl groups such as the methoxy- or ethoxycarbonyl group as well as the trifluoroacetyl group as G in compounds of formula (I) succeed by alkali hydrolysis under mild conditions without cleaving the A and D linked amide function. This is suitably valid for the cleavage of the triphenylmethyl group and the tert-butoxycarbonyl group as G in compounds of formula (I), which occurs in acidic medium under mild conditions. Finally, compounds of formula (I) with an allyloxycarbonyl group as G can be converted into such with hydrogen as G in neutral medium with palladium catalyst. All these methods are fully familiar to the person skilled in the art, and are furthermore also documented in monographs (see for example Greene, Wuts, Protective Groups in Organic Synthesis, New York, 1991).

Compounds of formula (I), wherein $R^4$ is an alkyl, alkenyl, alkinyl or cycloalkyl residue according to the above definition can also be produced, aside from the methods (a) and (b), (g) by reacting compounds of formula (I), wherein $R^4$ is hydrogen, with a suitable alkylation agent of formula (VIII)

$$L-R^4 \qquad (VIII)$$

wherein $R^4$ is an alkyl, alkenyl, alkinyl or cycloalkyl residue according to the above definition and L is a suitable nucleofuge, i.e. for example a halogen atom such as chlorine, bromine or iodine or a sulfonic acid ester of an alcohol. Preferred sulfonic acid esters (VIII) contain a methylsulfonyloxy residue, trifluoromethanesulfonyloxy-, p-toluenesulfonyloxy-, p-bromobenzenesulfonyloxy- or m-nitrobenzenesulfonyloxy residue as L.

As an amide alkylation in the presence of tertiary amino groups, this reaction requires the use of strong auxiliary bases such as potassium-tert-butylate, sodium hydride, potassium hydride or butyl lithium in aprotic, inert solvents. Such solvents can be for example aliphatic or aromatic hydrocarbons (pentane, hexane, heptane, benzene, toluene), ethers (for example, tetrahydrofuran, dioxane) or polar solvents such as dimethylsulfoxide, dimethylformamide or N-methylpyrrolidone. Depending on the reactivity of the educts, the reaction temperatures can lie between −40° C. and 140° C. preferably between −20° C. and 80° C.

The compounds of formula (I) produced according to the methods (a) to (g) can be isolated and purified in a known manner, for example by subjecting the residue after distillation of the solvent to partition, extraction, re-precipitation or recrystallization or another purification method. For this, column chromatography on a suitable support or preparative, middle or high pressure liquid chromatography are preferred for this.

The compounds (I) are first normally obtained in form of their free bases or their hydrates or solvates, depending on the type of isolation and purification. Their addition salts with pharmaceutically suitable acids are obtained in a typical manner by converting the base with the desired acid in a suitable solvent. Depending on the number of basic centers of compound (I), one or more equivalent acids per mole of base can be bound.

Suitable solvents are, for example, chlorinated hydrocarbons such as dichloromethane or chloroform; ethers such as diethyl ether, dioxane or tetrahydrofuran; acetonitrile; ketones such as acetone or ethyl methyl ketone; esters such as methyl acetate or ethyl acetate or low molecular alcohols such as methanol, ethanol or isopropanol; and water. Pure solvents as well as mixtures of two or three solvents can also be used. The salts can be isolated by crystallization, precipitation or the evaporation of the solvent. Thereby, they optionally accumulate as hydrates or solvates.

The bases can be recovered from the salts by alkalization, for example with aqueous ammonia solution, alkali carbonate or diluted sodium hydroxide solution.

The following listed compounds and/or their pharmaceutically acceptable salts, if not already concretely labelled as such, are particularly preferred.

N-[4-(1-methylsulfonylpiperidin-4-yl)-butyl]-3 (pyridin-3-yl)acrylamide,
N-{4-[1-(2-naphthylsulfonyl)-piperidin-4-yl]-butyl}-3-(pyridin-3-yl)-acrylamide,
N-{4-[1-(2-naphthylsulfonyl)-piperidin-4-yl]-butyl}-5-(pyridin-3-yl)-2,4-pentadienoic acid amide,
N-{4-[1-(1-naphthylaminocarbonyl)-piperidin-4-yl]-butyl}-3-(pyridin-3-yl)-acrylamide,
N-[4-(1-diphenylaminocarbonyl-piperidin-4-yl)-butyl]-3-(pyridin-3-yl)-acrylamide,
N-[4-(1-diphenylaminocarbonyl-piperidin-4-yl)-butyl]-5-(pyridin-3-yl)-2,4-pentadienoic acid amide,
N-{4-[1-(10,11-dihydrodibenzo[b,f]azepin-5-yl-carbonyl)-piperidin-4-yl]-butyl}-3-(pyridin-3-yl)-acrylamide,
N-[4-(1-diphenylphosphinoyl-piperidin-4-yl)-butyl]-3-(pyridin-3-yl)-acrylamide,
N-[4-(1-acetylpiperidin-4-yl)-butyl]-3-(pyridin-3-yl)-acrylamide,
N-[4-(1-diphenylacetyl-piperidin-4-yl)-butyl]-3-pyridin-3-yl)-acrylamide,
N-{4-[1-(3,3-diphenylpropionyl)-piperidin-4-yl]-butyl}-3-(pyridin-3-yl)-acrylamide,
N-[4-(1-benzoylpiperidin-4-yl)-butyl]-3-(pyridin-3-yl)-acrylamide,
N-[4-(1-benzoylpiperidin-4-yl)-butyl]-5-(pyridin-3-yl)-2,4-pentadienoic acid amide,
N-{4-[1-(9-oxo-9H-fluoro-4-yl-carbonyl)-piperidin-4-yl]-butyl}-3-(pyridin-3-yl)-acrylamide,
N-{4-[1-(phenylpyridin-3-yl-methyl)-piperidin-4-yl]-butyl}-3-(pyridin-3-yl)-acrylamide,
N-{4-[1 (phenylpyridin-4-yl-methyl)-piperidin-4-yl]-butyl}-3-(pyridin-3-yl)-acrylamide,
N-{4-[1-(6,11-dihydrodibenzo[b,e]oxepin-11-yl)-piperidin-4-yl]-butyl}-3-(pyridin-3-yl)-acrylamide,
N-{4-[1-(6,11-dihydrodibenzo[b,e]thiepin-11-yl)-piperidin-4-yl]-butyl}-3-(pyridin-3-yl)-acrylamide,
N-[7-(1-diphenylmethylpiperidin-4-yl)-heptyl]-3-(pyridin-3-yl)-acrylamide,
N-[8-(1-diphenylmethylpiperidin-4-yl)-octyl]-3-(pyridin-3-yl)-acrylamide,
N-[3-(1-diphenylmethylpiperidin-4-yloxy)-propyl]-3-(pyridin-3-yl)-acrylamide,
N-[3-(1-benzylpiperidin-4-yloxy)-propyl]-3-pyridin-3-yl)-acrylamide,
N-[2-(1-diphenylmethylpiperidin-4-yl)-ethyl]-5-(pyridin-3-yl)-2,4-pentadienoic acid amide,
N-[4-(1-diphenylmethylpiperidin-4-yl)-butyl]-5-(pyridin-3-yl-2,4-pentadienoic acid amide,
N-[5-(1-diphenylmethylpiperidin-4-yl)-pentyl]-5-(pyridin-3-yl)-2,4-pentadienoic acid amide or
N-[6-(1-diphenylmethylpiperidin-4-yl)-hexyl]-5-(pyridin-3-yl)-2,4-pentadienoic acid amide.

SYNTHETIC EXAMPLES

For the End Products of the Invention According to Formula (I)

In the following production examples for the end products, the abbreviations stand for the following terms:

MP=melting point,

RT=room temperature,

THF=tetrahydrofuan,

DMF=dimethylformamide,

CDI=carbonyldiimidazol, abs.=absolute,

EDC=N-(3-dimethylaminopropyl)-N'-ethyl-carbodiimide hydrochloride,

HOBT=1-hydroxybenzotriazol,

TEA=triethylamine.

$^1$H-NMR-Spectrum proton resonance spectrum, taken at 100 MHz. The chemical shifts are given in ppm against TMS as a standard ($\delta$=0.0), whereby

| | |
|---|---|
| s = | singlet, |
| d = | doublet, |
| t = | triplet, |
| dt = | doublet-triplet, |
| m = | multiplet, |
| ar = | aromatic, |
| py = | pyridine. |

Example 1

N-{4-[1-(diphenylaminocarbonyl)-piperidin-4-yl]-butyl}-3-(pyridin-3-yl)-acrylamide (substance 199)

6.5 g (18.0 mmol) N-[4-(piperidin-4-yl)-butyl]-3-(pyridin-3-yl)-acrylamide dihydrochloride (K22.142) and 5.77 ml (41.4 mmol) TEA are placed in 70 ml abs. dichlormethane and cooled to ca. 0° C. under moisture exclusion. 4.58 g (19.8 mmol) N,N-diphenylcarbamic acid chloride are dissolved in 20 ml abs. dichlormethane and added dropwise. The mixture is stirred at RT overnight without further cooling. 4 ml (28.7 mmol) TEA are added and the red colored suspension is stirred a further 2 hours at RT. Subsequently, the batch is washed with 80 ml water. The organic phase is dried over sodium sulfate and the solvent is removed under vacuum. The residue is chromatographically purified over silica gel with $CHCl_3/CH_3OH$ (98/2) and crystallized twice, each from 60 ml acetic acid ethyl ester, after drawing off the solvent. Beige colored crystals with a MP of 132–134° C.; yield: 5.3 g (60%).

| $C_{30}H_{34}N_4O_2$ (482.6) | |
|---|---|
| IR-spectrum (KBr): | $\nu$(NH) 3300 cm$^{-1}$ |
| | $\nu$(C=O) 1660 cm$^{-1}$ |
| $^1$H-NMR-spectrum (CDCl$_3$): | 0.60–1.75(11H, m, piperidine, piperidine-(CH$_2$)$_3$) |
| | 2.40–2.85(2 H, m, piperidine) |
| | 3.33(2 H, dt, CONHC$\underline{H}_2$. J=6.5 Hz. J=12.7 Hz) |
| | 3.85–4.20(2 H, m, piperidine) |
| | 5.95–6.20(1H, m, NH) |
| | 6.42(1H, d, CH=C$\underline{H}$CO, J=15.7 Hz) |
| | 6.90–7.45(11H, m, ar, py) |
| | 7.59(1H, d, C$\underline{H}$=CHCO, J=15.7 Hz) |
| | 7.65–7.90(1H, m, py) |
| | 8.45–8.60(1H, m, py) |
| | 8.65–8.85(1H, m, py) |

Example 2

N-[4-(1-diphenylacetyl-piperidin-4-yl)-butyl]-3-(pyridin-3-yl)-acrylamide (substance 150)

Production occurs analogously to example 1. However, no TEA is subsequently added.

Batch size: 5.0 g (13.9 mmol) N-[4-(piperidin-4-yl)-butyl]-3-(pyridin-3-yl)-acrylamide dihydrochloride (substance 14 as a dihydrochloride), 5.8 ml (41.6 mmol) TEA and 3.9 g (15.2 mmol) diphenylacetic acid chloride, In the purification, this is washed twice, each with 50 ml water. The chromatographic purification is carried out with $CHCl_3/CH_3OH$ (97/3 to 95/5). The residue is first crystallized twice, each from 15 ml acetic acid ethyl ester and then from 18 ml ethanol/diethyl ether (5/1). Colorless crystals remain with a MP of 161° C.; yield: 3.6 g (53%).

| $C_{31}H_{35}N_3O_2$ (481.6) | |
|---|---|
| IR-spectrum (KBr): | ν(NH) 3280 $cm^{-1}$ |
| | ν(C=O) 1665, 1530 $cm^{-1}$ |
| | ν(C=C) 1615 $cm^{-1}$ |
| $^1$H-NMR-spectrum (CDCl$_3$): | 0.50–1.85(11H, m, piperidine, piperidine-(CH$_2$)$_3$) |
| | 2.40–3.10(2 H, m, piperidine) |
| | 3.32(2 H, dt, CONHC$\underline{H}_2$. J=6.5 Hz. J=12.6 Hz) |
| | 3.80–4.05(1H, m, piperidine) |
| | 4.55–4.80(1H, m, piperidine) |
| | 5.23(1H, Ar$_2$CH) |
| | 6.10–6.35(1H, m, NH) |
| | 6.44(1H, d, CH=C$\underline{H}$CO, J=15.7 Hz) |
| | 7.10–7.45(11H, m, ar, py) |
| | 7.59(1H, d, C$\underline{H}$=CHCO, J=15.7 Hz) |
| | 7.60–7.85(1H, m, py) |
| | 8.50–8.65(1H, m, py) |
| | 8.65–8.80(1H, m, py) |

Example 3

N-{4-[1-(2-naphthyl-sulfonyl)-piperidin-4-yl]-butyl}-3-(pyridin-3-yl)-acrylamide (substance 219)

Production occurs analogously to example 2.

Batch size: 6.0 g (16.6 mmol) N-[4-piperidin-4-yl]-butyl]-3-pyridin-3-yl)-acrylamide dihydrochloride (substance 14 as dihydrochloride), 5.6 ml (40.0 mmol) TEA and 2.5 g (11.0 mmol) naphthalin-2-sulfonic acid chloride in 70 ml abs. dichlormethane.

In the work up, this is washed twice, each with 70 ml water. The chromatographic purification is carried out with $CHCl_3CH_3OH$ (95/5 to 94/6). The residue is crystallized from 30 ml acetic acid ethyl ester. Repeated chromatographic purification with $CHCl_3/CH_3OH$ (95/5). Yield: 2.7 g (57%); amorphous solid with a MP of 85–87° C.

| $C_{27}H_{31}N_3O_3S$ (477.5) | |
|---|---|
| IR-spectrum (KBr): | ν(NH) 3320 $cm^{-1}$ |
| | ν(C=O) 1690, 1560 $cm^{-1}$ |
| | ν(C=C) 1640 $cm^{-1}$ |
| $^1$H-NMR-spectrum (CDCl$_3$): | 0.90–1.95(11H, m, piperidine, piperidine-(CH$_2$)$_3$) |
| | 2.10–2.50(2 H, m, piperidine) |
| | 3.34(2 H, dt, CONHC$\underline{H}_2$. J=6.5 Hz, J=12.5 Hz) |
| | 3.65–4.00(2 H, m, piperidine) |
| | 5.85–6.15(1H, m, NH) |
| | 6.46(1H, d, CH=C$\underline{H}$CO, J=15.7 Hz) |
| | 7.15–8.10(9 H, m, ar, py. C$\underline{H}$=CHCO) |
| | 8.33(1H, s, Ar) |
| | 8.50–8.65(1H, m, py) |
| | 8.65–8.80(1H, m, py) |

Example 4

N-{4-[1-(1-naphthylaminocarbonyl)-piperidin-4-yl]-butyl}-3-(pyridin-3-yl)-acrylamide (substance 195)

2.35 g (13.9 mmol) 1-naphthyl isocyanate are dissolved in 10 ml abs. THF and a solution of 4.0 g (13.9 mmol) N-[4-(piperidin-4-yl)-butyl]-3-(pyridin-3-yl)-acrylamide (substance 14) in 30 ml abs. THF is added dropwise at RT under moisture exclusion. After ca one hour, a white precipitate forms and the suspension is stirred at RT overnight. The solid is drawn off, chromatographically purified over silica gel with $CHCl_3/CH_3OH$ (95/5 to 93/7) and crystallized from isopropanol after removal of the solvent. Colorless crystals remain with a MP of 198–200° C.; yield: 2.2 g (34%).

| $C_{28}H_{32}N_4O_2$ (456.6) | |
|---|---|
| IR-spectrum (KBr): | ν(NH) 3240 $cm^{-1}$ |
| | ν(C=O) 1660, 1560 $cm^{-1}$ |
| | ν(C=C) 1615 $cm^{-1}$ |
| $^1$H-NMR-spectrum (CDCl$_3$): | 1.00–1.95(11H, m, piperidine, piperidine-(CH$_2$)$_3$) |
| | 2.75–3.15(2 H, m, piperidine) |
| | 3.37(2 H, dt, CONHC$\underline{H}_2$. J=6.5 Hz. J=12.7 Hz) |
| | 3.95–4.25(2 H, m, piperidine) |
| | 5.75–6.05(1H, m, NH) |
| | 6.42(1H, d, CH=C$\underline{H}$CO, J=15.6 Hz) |
| | 6.70(1H, s, NH) |
| | 7.20–8.00(10 H, m, ar, py. C$\underline{H}$=CHCO) |
| | 8.50–8.65(1H, m, py) |
| | 8.65–8.80(1H, m, py) |

Example 5

N-{4-[1-(6,11-dihydro-dibenzo [b,e]thiepin-11-yl)-piperidin-4-yl]-butyl}-3-(pyridin-3-yl)-acrylamide (substance 136)

7.02 g (21.5 mmol) N-[4-(piperidin-4-yl)-butyl]-3-(pyridin-3-yl)-acrylamide dihydrochloride (substance 14 as a dihydrochloride) are suspended in 100 ml abs. dichlormethane and added to 7.08 g (70.0 mmol) TEA. The mixture is cooled to ca 0° C. under moisture exclusion and a solution of 5.30 g (21.5 mmol) 11-chlor-6,11-dihydro-dibenzo[b,e]thiepine in 10 ml abs. dichlormethane is added dropwise. The mixture is stirred for 24 hours at RT without further cooling. Subsequently, the batch is washed with 50 ml 10% sodium hydroxide solution and 30 ml water. The organic phase is dried over sodium sulfate and the solvent is removed under vacuum. The red brown residue is chromatographically purified three times over silica gel with $CHCl_3/CH_3OH$ (100/0, 97/3 and 96/4 to 94/6). Subsequently, a further purification occurs by means of MPLC with CHCl₃CH₃OH (98/2). Yield: 0.5 g (5%) of a brittle, vitreous solid with a MP of 89–91° C.

| $C_{31}H_{35}N_3OS$ (497.7) | |
|---|---|
| IR-spectrum (KBr): | ν(NH) 3280 cm⁻¹ |
| | ν(C=O) 1660, 1550 cm⁻¹ |
| | ν(C=C) 1620 cm⁻¹ |
| ¹H-NMR-spectrum (CDCl₃): | 0.90–2.00(13 H, m, piperidine, piperidine-(CH₂)₃) |
| | 2.55–2.95(2 H, m, piperidine) |
| | 3.20–3.60(3 H, m, CONHC$\underline{H}$₂, SCH₂) |
| | 4.03(1H, Ar₂CH) |
| | 6.10–6.35(1H, m, NH) |
| | 5.95–6.30(1H, m, SCH₂) |
| | 6.44(1H, d, CH=C$\underline{H}$CO, J=15.7 Hz) |
| | 6.85–7.40(9 H, m, ar, py) |
| | 7.61(1H, d, C$\underline{H}$=CHCO, J=15.7 Hz) |
| | 7.65–7.85(1H, m, py) |
| | 8.50–8.65(1H, m, py) |
| | 8.65–8.80(1H, m, py) |

Example 6

N-[4-(1-diphenylmethyl-piperidin-4-yl)-butyl]-5-(pyridin-3-yl)-2,4-pentadienoic acid amide (substance 70)

3.85 g (22.0 mmol) 5-(3-pyridyl)-2,4-pentadienoic acid are suspended in 90 ml abs. dichlormethane and after addition of three drops of pyridine, cooled to ca. 0° C. in an ice bath under moisture exclusion. 3.8 g (30.0 mmol) oxalyl chloride are added dropwise and the mixture is stirred at RT overnight. Subsequently, the solvent and excess oxalyl chloride is distilled off on a rotary evaporator. In order to completely remove the oxalyl chloride, the residue is dried for two hours under high-vacuum. The acid chloride obtained in this manner is suspended in 50 ml abs. dichloromethane and cooled to ca. 0° C. in an ice bath under moisture exclusion. 6.44 g (20.0 mmol) 4-(1-diphenylmethyl-piperidin-4-yl)-butylamine are dissolved in 40 ml abs. dichlormethane and added dropwise to this suspension. After complete addition, the ice bath is removed and the reaction is stirred for an additional two hours at RT. The mixture is subsequently washed with 10% sodium hydroxide solution. The organic phase is washed twice, each with 40 ml water, dried over sodium sulfate and the solvent is removed under vacuum. The residue is chromatographically purified over silica gel with CHCl₃/CH₃OH (98/2 to 95/5) and crystallized twice from 250 ml and 200 ml acetonitrile after drawing off the solvent. Beige colored crystals with a MP of 164–166° C.; yield: 4.7 g (49%).

| $C_{32}H_{37}N_3O$ (479.6) | |
|---|---|
| IR-spectrum (KBr): | ν(NH) 3280 cm⁻¹ |
| | ν(C=O) 1650, 1550 cm⁻¹ |
| | ν(C=C) 1600 cm⁻¹ |
| ¹H-NMR-spectrum (CDCl₃): | 1.00–2.00(13 H, m, piperidine, piperidine-(CH₂)₃) |
| | 2.70–3.00(2 H, m, piperidine) |
| | 3.34(2 H, dt, CONHC$\underline{H}$₂, J=6.6 Hz. J=12.8 Hz) |
| | 4.21(1H, s, Ar₂CH) |
| | 5.50–5.75(1H, m, NH) |
| | 6.44(1H, d, CH=CH, J=14.7 Hz) |

| $C_{32}H_{37}N_3O$ (479.6) | |
|---|---|
| | 6.75–6.95(2 H, m, CH=CH) |
| | 7.05–7.50(12 H, m, ar, py. CH=CH) |
| | 7.65–7.85(1H, m, py) |
| | 8.45–8.55(1H, m, py) |
| | 8.60–8.75(1H, m, py) |

Example 7

N-[4-(1-benzoylpiperidin-4-yl)-butyl]-3-(pyridin-3-yl)-acrylamide (substance 159)

5.1 g (36.2 mMol) benzoyl chloride are dissolved in 150 ml abs. dichlormethane and cooled to ca 0° C. under moisture exclusion. 10.4 g (36.2 mmol) N-[4-(piperidin-4-yl)-butyl]-3-(pyridin-3-yl)-acrylamide (substance 14) are dissolved in 50 ml abs. dichlormethane and added dropwise under ice cooling. The mixture is stirred overnight at RT without further cooling. Subsequently, the suspension is added to 60 ml 2 M sodium hydroxide and extracted twice, each with 80 ml dichlormethane. The combined organic phases are washed twice, each with 60 ml water, dried over sodium sulfate and the solvent is removed under vacuum. The residue is chromatographically purified over silica gel with CHCl₃/CH₃OH (97/3 to 95/5) and recrystalized from 75 ml acetonitrile. Colorless crystals with a MP of 100–102° C. are recovered; yield: 9.8 g (69%).

| $C_{24}H_{29}N_3O_2$ (391.5) | | |
|---|---|---|
| IR-spectrum (KBr): | ν(NH) | 3280 cm⁻¹ |
| | ν(C=O) | 1670, 1545 cm⁻¹ |
| | ν(C=C) | 1630 cm⁻¹ |
| ¹H-NMR-spectrum (CDCl₃): | 0.80–2.00(11H, m, piperidine, piperidine-(CH₂)₃) | |
| | 2.55–4.00(5H, m, piperidine, CONHC$\underline{H}$₂) | |
| | 4.40–4.90(1H, piperidine) | |
| | 6.00–6.25(1H, m, NH) | |
| | 6.48(1H, d, CH=C$\underline{H}$CO, J=15.7Hz) | |
| | 7.15–7.95(8H, m, ar, py. C$\underline{H}$=CHCO) | |
| | 8.50–8.65(1H, m, py) | |
| | 8.65–8.80(1H, m, py) | |

Example 8

N-(1-diphenylmethyl-azetin-3-ylmethyl)-3-(pyridin-3-yl)-acrylamide (substance 1)

Production occurs analogously to example 6.
Batch size: 4.3 g (28.7 mmol) 3-(3-pyridyl)-acrylic acid, 6.7 ml (78.4 mmol) oxalyl chloride and 6.6 g (26.1 mmol) (1-diphenylmethyl-azetidin-3-ylmethyl)-anine.

In the work up, the reaction mixture is washed with 10% sodium hydroxide solution. The aqueous phase is extracted twice, each with 50 ml dichlormethane. The combined organic phases are dried over sodium sulfate and the solvent is removed under vacuum. The residue is chromatographically pre-purified over silica gel with CHCl₃/CH₃OH (98/2 to 95/5) and subsequently purified by two-fold flash-chromatography with CHCl₃/CH₃OH (9911 to 95/5). After drawing off the solvent, an amorphous solid remains with a MP of 72–74° C.; yield: 0.75 g (7%).

| C$_{25}$H$_{25}$N$_3$O (383.5) | | |
|---|---|---|
| IR-spectrum (KBr): | ν(NH) | 3320 cm$^{-1}$ |
| | ν(C=O) | 1680, 1570 cm$^{-1}$ |
| | ν(C=C) | 1640 cm$^{-1}$ |
| $^1$H-NMR-spectrum (CDCl$_3$): | 2.40–2.80(1H, m, azetidine) | |
| | 2.80–3.10(2H, m, azetidine) | |
| | 3.10–3.40(2H, m, azetidine) | |
| | 3.60(2H, dd, CONHC<u>H</u>$_2$, J=5.7Hz) | |
| | 4.36(1H, Ar$_2$CH) | |
| | 6.45–6.75(1H, m, NH) | |
| | 6.50(1H, d, CH=C<u>H</u>CO, J=15.7Hz) | |
| | 7.00–7.50(11H, m, ar, py) | |
| | 7.62(1H, d, C<u>H</u>=CHCO, J=15.7Hz) | |
| | 7.65–7.90(1H, m, py) | |
| | 8.50–8.70(1H, m, py) | |
| | 8.70–8.85(1H, m, py) | |

Example 9

N-(4-diphenylmethyl-morpholin-2-ylmethyl)-3-(pyridin-3-yl)-acrylamide (substance 250)

Production occurs analogously to example 6.

Batch size: 2.3 g (15.6 mmol) 3-(3-pyridyl)-acrylic acid, 5.4 g (42.5 mmol) oxalyl chloride and 3.6 g (14.7 mmol) 2-aminomethyl-4-diphenylmethylmorpholine.

In the work up, 40 ml 10% sodium hydroxide solution are added to the reaction solution. The aqueous phase is extracted with 15 ml dichlormethane. The combined organic phases are washed twice, each with 15 ml water, dried over sodium sulfate and the solvent is removed under vacuum. The residue is chromatographically purified three times over silica gel with CHCl$_3$/CH$_3$OH (95/5, 90/10 and 90/10). After drawing off the solvent, an amorphous solid remains with a MP of 71–74° C.; yield: 0.8 g (13%).

| C$_{26}$H$_{27}$N$_3$O$_2$ (413.5) | | |
|---|---|---|
| IR-spectrum (KBr): | ν(NH) | 3270 cm$^{-1}$ |
| | ν(C=O) | 1655, 1540 cm$^{-1}$ |
| | ν(C=C) | 1620 cm$^{-1}$ |
| $^1$H-NMR-spectrum (CDCl$_3$): | 1.70–2.30(2H, m, morpholine) | |
| | 2.55–2.90(2H, m, morpholine) | |
| | 3.00–3.35(1H, m, morpholine) | |
| | 3.50–4.00(4H, m, CONHC<u>H</u>$_2$, morpholine) | |
| | 4.20(1H, Ar$_2$CH) | |
| | 6.00–6.25(1H, m, NH) | |
| | 6.47(1H, d, CH=C<u>H</u>CO, J=15.7Hz) | |
| | 7.00–7.55(11H, m, ar, py) | |
| | 7.60(1H, d, C<u>H</u>=CHCO, J=15.7Hz) | |
| | 7.65–7.90(1H, m, py) | |
| | 8.50–8.70(1H, m, py) | |
| | 8.70–8.80(1H, m, py) | |

Example 10

N-{4-[1-(9-oxo-9H-fluoren-4-yl-carbonyl)-piperidin-4-yl]-butyl}-3-(pyridin-3-yl)-acrylamide (substance 178)

5.0 g (20.0 mmol) 95% 9-fluorenon-carboxylic acid chloride are dissolved in 70 ml abs. dichlormethane and 6.5 g (18.2 mmol) N-[4-(piperidin-4-yl)-butyl]-3-(pyridin-3-yl)-acrylamide dihydrochloride (substance 14 as a dihydrochloride) are added. The mixture is cooled to ca. 0° C. under moisture exclusion and 4.0 g (40.0 mmol) TEA dissolved in 10 ml abs. dichlormethane are added dropwise. The batch is stirred at RT overnight without further cooling. In the work up, 150 ml 10% sodium hydroxide solution are added to the reaction solution and this is extracted by shaking. The organic phase is washed with 100 ml water, dried over sodium sulfate and the solvent is removed under vacuum. The residue is pre-purified over silica gel with CHCl$_3$/CH$_3$OH (96/4 to 95/5) and subsequently purified by flash-Chromatography with CHCl$_3$/CH$_3$OH (95/5). After drawing off the solvent, the product remains as a yellow vitreous solid with a MP of 80–82° C.; yield: 2.3 g (25%).

| C$_{31}$H$_{31}$N$_3$O$_3$ (493.6) | | |
|---|---|---|
| IR-spectrum (KBr): | ν(NH) | 3320 cm$^{-1}$ |
| | ν(C=O) | 1730, 1640 cm$^{-1}$ |
| | ν(C=C) | 1620 cm$^{-1}$ |
| $^1$H-NMR-spectrum (CDCl$_3$): | 0.70–2.05(11H, m, piperidine, piperidine-(CH$_2$)$_3$) | |
| | 2.60–3.80(5H, m, piperidine, CONHC<u>H</u>$_2$) | |
| | 4.70–5.05(1H, piperidine) | |
| | 5.85–6.20(1H, m, NH) | |
| | 6.47(1H, d, CH=C<u>H</u>CO, J=15.7Hz) | |
| | 7.15–7.90(10H, m, ar, py. C<u>H</u>=CHCO) | |
| | 8.50–8.65(1H, m, py) | |
| | 8.65–8.85(1H, m, py) | |

Example 11

N-[3-(1-benzyl-piperidin-4-yloxy)-propyl]-3-(pyridin-3-yl)-acrylamide (substance 39)

2.4 g (16.2 mmol) 3-(3-pyridyl)-acrylic acid and 2.3 ml (16.2 mmol) TEA are suspended in 50 ml abs. toluene and a solution of 1.5 ml (15.5 mmol) chloroformic acid ethyl ester in 20 ml abs. toluene are added dropwise under moisture exclusion and light cooling. This yellow suspension is stirred at RT for two hours and then a solution of 3.5 g (14.1 mmol) 3-(1-benzylpiperidin-4-yloxy)-propylamine in 20 ml abs. toluene is added dropwise. The mixture is stirred for two hours at RT and extracted by shaking three times in the heat, each with 10 ml water, 2 M sodium hydroxide and water again. The organic phase is concentrated under vacuum and the orange colored oily residue is chromatographically purified twice over silica gel with CHCl$_3$/CH$_3$OH/NH$_4$OH (90/9/1 and 95/5/0 to 90/10/0) and crystallized from 10 ml acetic acid ethyl ester. Colorless crystals remain with a MP of 100–102° C.; yield: 1.9 g (35%).

| C$_{23}$H$_{29}$N$_3$O$_2$ (379.5) | | |
|---|---|---|
| IR-spectrum (KBr): | ν(NH) | 3290 cm$^{-1}$ |
| | ν(C=O) | 1650, 1530 cm$^{-1}$ |
| | ν(C=C) | 1610 cm$^{-1}$ |
| $^1$H-NMR-spectrum (CDCl$_3$): | 1.50–2.45(8H, m, piperidine, C—CH$_2$—C) | |
| | 2.70–3.00(2H, m, piperidine) | |
| | 3.25–3.80(7H, m, piperidine, CONHC<u>H</u>$_2$. Ar—CH$_2$. O—CH$_2$) | |
| | 6.54(1H, d, CH=C<u>H</u>CO, J=15.7Hz) | |
| | 6.70–6.95(1H, m, NH) | |

| $C_{23}H_{29}N_3O_2$ (379.5) | | |
|---|---|---|
| | 7.25–7.50(6H, m, ar, py) | |
| | 7.69(1H, d, C$\underline{H}$=CHCO, J=15.7Hz) | |
| | 7.80–8.00(1H, m, py) | |
| | 8.60–8.75(1H, m, py) | |
| | 8.75–8.90(1H, m, py) | |

Example 12

N-[6-(1-diphenylmethyl-piperidin-3-yl-carbonyl-amineo)-hexyl]-3-(pyridin-3-yl)-acrylamide (substance 103)

1.79 g (12.0 mmol) 3-(3-pyridyl)-acrylic acid and 4.0 g (39.5 mmol) TEA are suspended in 80 ml abs. dichloromethane and cooled to ca. 0° C. under moisture exclusion. 2.2 g (14.3 mmol) 88% HOBT and 2.76 g (14.4 mmol) EDC are added and the mixture is stirred 30 min under ice cooling. 5.6 g (12.0 mmol) 1-diphenylmethyl-piperidin-3-carboxylic acid-(6-amino-hexyl)-amide dihydrochloride are added and the mixture is stirred overnight at RT without cooling. Subsequently, the batch is washed twice with sodium hydroxide with 50 ml 2M sodium hydroxide solution and 70 ml water. The organic phase is dried over sodium sulfate and the solvent is removed under vacuum. The residue is chromatographically purified over silica gel with CHCl$_3$CH$_3$OH (96/4 to 95/5) and crystallized from 70 ml acetonitrile. Colorless crystals remain with a MP of 129–131° C.; yield: 3.9 g (62%).

| $C_{33}H_{40}N_4O_2$ (524.7) | | |
|---|---|---|
| IR-spectrum (KBr): | ν(NH) | 3300 cm$^{-1}$ |
| | ν(C=O) | 1640, 1540 cm$^{-1}$ |
| | ν(C=C) | 1620 cm$^{-1}$ |
| $^1$H-NMR-spectrum (CDCl$_3$): | 1.20–2.95(17H, m, piperidine, C—(CH$_2$)$_4$—C) | |
| | 3.15–3.55(4H, m, CONHC$\underline{H}_2$) | |
| | 4.24(1H, Ar$_2$CH) | |
| | 6.30–6.55(1H, m, NH) | |
| | 6.57(1H, d, CH=C$\underline{H}$CO, J=15.7Hz) | |
| | 7.05–7.45(11H, m, ar, py) | |
| | 7.62(1H, d, C$\underline{H}$=CHCO, J=15.7Hz) | |
| | 7.65–8.00(2H, m, py. NH) | |
| | 8.50–8.60(1H, m, py) | |
| | 8.65–8.80(1H, m, py) | |

Example 13

N-[4-(1-diphenylphosphinyl-piperidin-4-yl)-butyl]-3-(pyridin-3-yl)-acrylamide (substance 232)

1.06 ml (5.55 mmol) diphenylphosphinic acid chloride are dissolved in 20 ml abs. THF and cooled to ca. 0° C. under moisture exclusion. 2.0 g (5.55 mmol) N-[4-(piperidin-4-yl)-butyl]-3-(pyridin-3-yl)-acrylamide dihydrochloride (substance 14 as a dihydrochloride) and 2.3 ml (16.6 mmol) TEA are suspended in 90 ml abs. THF and added dropwise under ice cooling. The mixture is stirred for four days at RT without further cooling. Subsequently, the solvent is removed under vacuum and the residue is taken up in 70 ml 10% sodium hydroxide solution and extracted twice, each with 100 ml CHCl$_3$. The combined organic phases are washed with saturated NaCl solution, dried over sodium sulfate and the solvent is removed under vacuum. The residue is pre-purified over silica gel with CHCl$_3$/CH$_3$OH (90/10), subsequently further purified by flash-chromatography with CHCl$_3$/CH$_3$OH (90/10) and crystallized from 30 ml acetic acid ethyl ester. Colorless crystals remain with a MP of 154–155° C.; yield: 1.04 g (30%).

| $C_{29}H_{34}N_3O_2P$ (487.6) | | |
|---|---|---|
| IR-spectrum (KBr): | ν(NH) | 3260 cm$^{-1}$ |
| | ν(C=O) | 1650, 1550 cm$^{-1}$ |
| | ν(C=C) | 1610 cm$^{-1}$ |
| $^1$H-NMR-spectrum (CDCl$_3$): | 0.90–1.80(11H, m, piperidine, piperidine-(CH$_2$)$_3$) | |
| | 2.55–2.95(2H, m, piperidine) | |
| | 3.10–3.55(4H, m, piperidine, CONHC$\underline{H}_2$) | |
| | 6.59(1H, d, CH=C$\underline{H}$CO, J=15.7Hz) | |
| | 6.55–6.80(1H, m, NH) | |
| | 7.15–8.00(13H, m, ar, py. C$\underline{H}$=CHCO) | |
| | 8.50–8.60(1H, m, py) | |
| | 8.60–8.80(1H, m, py) | |

Example 14

N-[4-(1-benzyl-piperidin-3-yl)-butyl]-3-(pyridin-3-yl)-acrylamide (substance 40)

Production occurs analogously to example 6.

Batch size: 2.6 g (17.4 mmol) 3-(3-pyridyl)-acrylic acid, 1.6 ml (19.0 mmol) oxalyl chloride and 3.9 g (15.8 mmol) 4-(1-benzyl-piperidin-3-yl)-butylamine in 100 ml abs. dichlormethane.

The reaction time is prolonged to 6 hours at RT. In the work up, the batch is washed with 50 ml 1 M sodium hydroxide solution and the aqueous phase is extracted with 50 ml dichlormethane. The combined organic phases are concentrated under vacuum and the residue is chromatographically pre-purified twice over silica gel with CHCl$_3$/CH$_3$OH (93/7 and 95/5), subsequently purified further by flash-chromatography with CHCl$_3$/CH$_3$OH (95/5 and 97/3) and crystallized from 5 ml acetic acid ethyl ester. Colorless crystals remain with a MP of 80–82° C.; yield: 0.9 g (15%).

| $C_{24}H_{31}N_3O$ (377.5) | | |
|---|---|---|
| IR-spectrum (KBr): | ν(NH) | 3300 cm$^{-1}$ |
| | ν(C=O) | 1650, 1530 cm$^{-1}$ |
| | ν(C=C) | 1610 cm$^{-1}$ |
| $^1$H-NMR-spectrum (CDCl$_3$): | 1.00–2.10(13H, m, piperidine, piperidine-(CH$_2$)$_3$) | |
| | 2.65–2.95(2H, m, piperidine) | |
| | 3.37(2H, dt, CONHC$\underline{H}_2$, J=6.5Hz. J=12.7Hz) | |
| | 3.50(2H, s, Ar—CH$_2$) | |
| | 5.65–5.95(1H, m, NH) | |
| | 6.46(1H, d, CH=C$\underline{H}$CO, J=15.6Hz) | |
| | 7.10–7.40(6H, m, ar, py) | |
| | 7.62(1H, d, C$\underline{H}$=CHCO, J=15.6Hz) | |
| | 7.65–7.90(1H, m, py) | |
| | 8.50–8.65(1H, m, py) | |
| | 8.70–8.80(1H, m, py) | |

Example 15

N-[4-(1-tert-Butoxycarbonylpiperidin-4-yl)-butyl]-3-(pyridin-3-yl)-acrylamide (substance 242)

Production occurs analogously to example 6. TEA is also added dropwise with the addition of the amine.

Batch size: 16.4 g (110 mmol) 3-(3-pyridyl)acrylic acid, 18.9 g (150 mmol) oxalyl chloride, 25.6 g (100 mmol) 4-(1-tert-butoxycarbonyl-piperidin-4-yl)-butylamine and 10.1 g (100 mmol) TEA in 300 ml abs. dichlormethane.

In the work up, 100 ml 10% sodium hydroxide solution are added to the reaction solution. The aqueous phase is extracted with 30 ml dichlormethane. The combined organic phases are washed twice, each with 25 ml water, and the solvent is removed under vacuum. The residue is dissolved in $CHCl_3/CH_3OH$ (90/10) and filtered through a thin silica gel layer. After drawing off the solvent, the crude product remains as a red oil (44.0 g). For purification, this is chromatographed with $CHCl_3/CH_3OH$ (95/5) on silica gel. Yield: 26.5 g (68%) as a yellow viscous oil.

| $C_{22}H_{33}N_3O_3$ (387.50) | | |
|---|---|---|
| IR-spectrum (KBr): | ν(NH) | 3250 cm$^{-1}$ |
| | ν(C=O) | 1670, 1540 cm$^{-1}$ |
| | ν(C=C) | 1600 cm$^{-1}$ |
| $^1$H-NMR-spectrum (CDCl$_3$): | 0.80–1.90(20H, m, piperidine, piperidine-(CH$_2$)$_3$, tert, butyl) | |
| | 2.30–2.90(2H, m, piperidine) | |
| | 3.10–3.60(2H, m, piperidine) | |
| | 3.80–4.30(2H, m, CONHC$\underline{H}_2$) | |
| | 6.15–6.55(1H, m, NH) | |
| | 6.43(1H, d, CH=C$\underline{H}$CO, J=15.6Hz) | |
| | 7.05–7.85(2H, m, py) | |
| | 7.51(1H, d, C$\underline{H}$=CHCO, J=15.6Hz) | |
| | 8.35–8.55(1H, m, py) | |
| | 8.55–8.70(1H, m, py) | |

Example 16

N-[4-(piperidin-4-yl)-butyl]-3-pyridin-3-yl)-acrylamide dihydrochloride (substance 14 as a dihydrochloride)

44.0 g (<113.5 mmol) crude N-{4-[N-(tert-butoxycarbonyl)-piperidin-4-yl]-butyl}-3-(pyridin-3-yl)-acrylamide (substance 242) are dissolved in 400 ml ethanol and added to 26.0 ml conc. hydrochloric acid. The mixture is heated to boiling for three hours and, after cooling, the solvent is removed under vacuum. The yellow residue is crystallized from 500 ml isopropanol. Beige colored crystals remain with a MP of 178–188° C.; yield: 32.6 g (90%).

| $C_{17}H_{25}N_3O$·2 HCl (360.3) | | |
|---|---|---|
| IR-spectrum (KBr): | ν(NH) | 3260 cm$^{-1}$ |
| | ν(C=O) | 1670, 1545 cm$^{-1}$ |
| | ν(C=C) | 1630 cm$^{-1}$ |
| $^1$H-NMR-spectrum (D$_2$O): | 0.95–1.95(11H, m, piperidine, piperidine-(CH$_2$)$_3$) | |
| | 2.60–3.00(2H, m, piperidine) | |
| | 3.00–3.40(4H, m, piperidine, CONHC$\underline{H}_2$) | |
| | 6.73(1H, d, CH=C$\underline{H}$CO, J=15.9Hz) | |
| | 7.41(1H, d, C$\underline{H}$=CHCO, J=15.9Hz) | |
| | 7.80–8.00(1H, m, py) | |
| | 8.50–8.65(2H, m, py) | |
| | 8.65–8.90(1H, m, py) | |

The invention is more closely illustrated by means of the further synthesis examples listed in the following Table 2, without restricting the invention.

TABLE 2

Prepared compounds of formula (I)

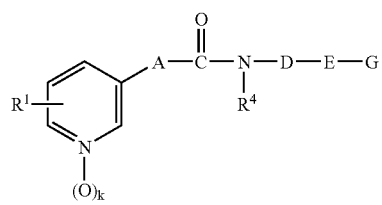

| Nr | R$^1$ | A | D—E—G | MP [° C.] (solvent)$^1$ |
|---|---|---|---|---|
| 1 | H | CH=CH | 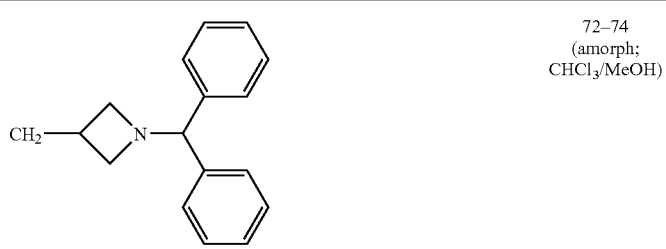 | 72–74 (amorph; CHCl$_3$/MeOH) |

TABLE 2-continued

Prepared compounds of formula (I)

| Nr | R[1] | A | D—E—G | MP [° C.] (solvent)[1] |
|----|------|---|-------|------------------------|
| 4 | H | CH=CH | CH₂CH₂NH—C(=O)—O—[azetidine]—N—CH(C₆H₅)(C₆H₅) (diphenylmethyl azetidinyl) | 164–165 (EE) |
| 14 | H | CH=CH | CH₂CH₂CH₂CH₂—[piperidine]—NH | 140–142 (amorph; CH₂Cl₂) |
| 14 | H | CH=CH | CH₂CH₂CH₂CH₂—[piperidine]—NH | 178–188[2] (iPrOH) |
| 15 | H | CH=CH—CH=CH | CH₂CH₂CH₂CH₂—[piperidine]—NH | 197–202[2] (iPrOH) |
| 39 | H | CH=CH | CH₂CH₂CH₂O—[piperidine]—N—CH₂—C₆H₅ | 100–102 (EE) |
| 40 | H | CH=CH | [piperidine with N—CH₂—C₆H₅ and 3-CH₂CH₂CH₂CH₂—] | 80–82 (EE) |
| 54 | H | CH=CH | CH₂—[piperidine]—N—CH(C₆H₅)₂ | 135–136 (EE) |
| 59 | H | CH=CH | NH—C(=O)—[piperidine]—N—CH(C₆H₅)₂ | 221–223 (MeOH) |
| 62 | H | CH=CH | CH₂CH₂NH—[piperidine]—N—CH(C₆H₅)₂ | 139–140 (EE) |
| 63 | | | pyridine N-oxide—CH=CH—C(=O)—NH—CH₂CH₂CH₂CH₂—[piperidine]—N—CH(C₆H₅)₂ | ca. 205 (Zers.) (CHCl₃) |

TABLE 2-continued

Prepared compounds of formula (I)

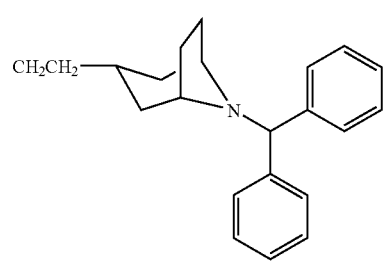

| Nr | R¹ | A | D—E—G | MP [° C.] (solvent)[1] |
|---|---|---|---|---|
| 65 | H | CH=C(CN) | CH₂CH₂CH₂CH₂—[piperidine-N—CH(C₆H₅)₂] | 142–144 (MeCN) |
| 70 | H | CH=CH—CH=CH | CH₂CH₂CH₂CH₂—[piperidine-N—CH(C₆H₅)₂] | 164–166 (MeCN) |
| 97 | H | CH=CH | CH₂CH₂NH—C(=O)—O—[piperidine-N—CH(C₆H₅)₂] | 178–180 (EE) |
| 103 | H | CH=CH | [piperidine-N—CH(C₆H₅)₂ with (CH₂)₆NH—C(=O)— substituent] | 129–131 (MeCN) |
| 107 | H | CH=CH | CH₂CH₂—[azabicyclic-N—CH(C₆H₅)₂] | 190–192 (MeCN) |
| 134 | H | CH=CH | CH₂CH₂CH₂CH₂—[piperidine-N—(dibenzoxepine)] | 139–141 (EE) |
| 136 | H | CH=CH | CH₂CH₂CH₂CH₂—[piperidine-N—(dibenzothiepine)] | 89–91 (amorph; CHCl₃/MeOH) |

TABLE 2-continued

Prepared compounds of formula (I)

| Nr | R[1] | A | D—E—G | MP [° C.] (solvent)[1] |
|---|---|---|---|---|
| 140 | H | CH=CH | CH₂CH₂CH₂CH₂-piperidine-N-C(=O)-CH₃ | Harz[3] |
| 150 | H | CH=CH | CH₂CH₂CH₂CH₂-piperidine-N-C(=O)-CH(phenyl)₂ | 161 (EtOH/Et₂O) |
| 151 | H | CH=CH—CH=CH | CH₂CH₂CH₂CH₂-piperidine-N-C(=O)-CH(phenyl)₂ | 77–79 (EE/BuCl) |
| 153 | H | CH=CH | CH₂CH₂CH₂CH₂-piperidine-N-C(=O)-CH₂-CH(phenyl)₂ | 105–106 (MeCN/MTBE) |
| 159 | H | CH=CH | CH₂CH₂CH₂CH₂-piperidine-N-C(=O)-phenyl | 100–102 (MeCN) |
| 162 | H | CH=CH—CH=CH | CH₂CH₂CH₂CH₂-piperidine-N-C(=O)-phenyl | 133–135 (EE/BuCl) |

TABLE 2-continued

Prepared compounds of formula (I)

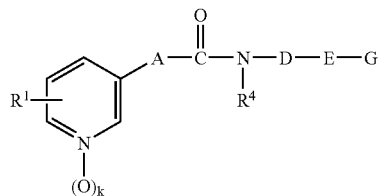

| Nr | R¹ | A | D—E—G | MP [° C.] (solvent)[1] |
|---|---|---|---|---|
| 178 | H | CH=CH | CH₂CH₂CH₂CH₂-[piperidine]-N-C(O)-[fluorenone] | 80–82 (amorph; CHCl₃/MeOH) |
| 195 | H | CH=CH | CH₂CH₂CH₂CH₂-[piperidine]-N-C(O)-NH-[naphthyl] | 198–200 (iPrOH) |
| 199 | H | CH=CH | CH₂CH₂CH₂CH₂-[piperidine]-N-C(O)-N(phenyl)₂ | 132–134 (EE) |
| 200 | H | CH=CH—CH=CH | CH₂CH₂CH₂CH₂-[piperidine]-N-C(O)-N(phenyl)₂ | 146–148 (iPrOH) |
| 219 | H | CH=CH | CH₂CH₂CH₂CH₂-[piperidine]-N-SO₂-[naphthyl] | 85–87 (amorph; CHCl₃/MeOH) |
| 232 | H | CH=CH | CH₂CH₂CH₂CH₂-[piperidine]-N-P(O)(phenyl)₂ | 154–155 (EE) |
| 242 | H | CH=CH | CH₂CH₂CH₂CH₂-[piperidine]-N-C(O)-O-C(CH₃)₃ | Ol[3] |

TABLE 2-continued

Prepared compounds of formula (I)

| Nr | R¹ | A | D—E—G | MP [° C.] (solvent)[1] |
|---|---|---|---|---|
| 243 | H | CH=CH—CH=CH | CH₂CH₂CH₂CH₂—piperidine-N-C(=O)-O-C(CH₃)₃ | 135–136 (EE) |
| 250 | H | CH=CH | 2-(CH₂)-morpholine-N-CH(phenyl)₂ | 71–74 (amorph; CHCl₃/MeOH) |

Table annotation
[1]MeOH = methanol
EE = ethyl acetate
iPrOH = isopropanol
MeCN = acetonitrile
EtOH = ethanol
Et₂O = diethyl ether
BuCl = 1-chlorobutane
MTBE = methyl tert-butyl ether
[2]as a dihydrochloride
[3]purified by column chromatography Several examples for the production of the starting compounds are described in the following for the better illustration of the production of the end products.

Synthesis of the Starting Compounds

Example 1A 4-(1-tert-butoxycarbonyl-piperidin-4-yl)-butan-1-ol 100 g (458 mmol) 4-piperidin-4-yl-butan-1-ol hydrochloride are dissolved in 120 ml water, added to 216 ml (1550 mmol) TEA and cooled to ca 5–10° C. 122 g (559 mmol) di-tert-butyl dicarbonate are dissolved in 400 ml THF and added dropwise within four hours under further cooling. The mixture is left to stand without further cooling at RT overnight. Subsequently, the THF is removed under vacuum to a large extent and the residue is extracted twice, each with 300 ml and 200 ml CHCl₃ respectively, and the combined organic phases are washed twice, each with 20 ml water. The solvent is removed under vacuum. The residue is dried under high-vacuum and processed further without additional purification. Yield: 136 g (102%).

Example 2A

2-[4-(1-tert-butoxycarbonylpiperidin-4-yl)-butyl]-isoindol-1,3-dione 136 g (<528 mmol) 4-[1-tert-butoxycarbonylpiperidin-4-yl)-butan-1-ol (crude product), 135.3 g (516 mmol) Triphenylphosphine and 75.9 g (516 mmol) phthalimide are suspended in 1800 ml THF and 89.9 g (516 mmol) azodicarboxylic acid diethyl ester are added dropwise within three hours under protective atmosphere and light cooling (to ca. 15° C.). The mixture is left to stand at RT overnight without further cooling. Subsequently, the solvent is removed under vacuum and the oily residue is dissolved in 500 ml acetic acid ethyl ester and held at 0° C. overnight. The sedimented precipitate is filtered and discarded. The solution is concentrated under vacuum and the oily residue is chromatographically purified over silica gel with CHCl₃ and crystallized from 200 ml isopropanol after drawing off the solvent. Colorless crystals remain with a MP of 100–102° C.; yield: 108.5 g (57%).

Example 3A 4-(1-tert-butoxycarbonylpiperidin-4-yl)butylamine 113.0 g (292 mmol) 2-[4-(1-tert-butoxycarbonylpiperidin-4-yl)-butyl]-isoindol-1,3-dione are dissolved in 600 ml ethanol, added to 29.3 g (585 mmol) hydrazine hydrate and heated to boiling for three hours. After cooling the solution, the mixture is filtered and the filtrate is concentrated under vacuum. The residue is dispersed in the heat (ca. 50° C.) between 500 ml toluene and 500 ml 10% sodium hydroxide solution. The organic phase is washed once with 50 ml 10% sodium hydroxide solution and twice, each with 50 ml water. The solvent is removed under vacuum and the residue is dried at 70° C. under high-vacuum and processed further without additional purification. Yield of colorless oil: 64.0 g (85%).

Example 4A (1-diphenylmethyl-azetidin-3-ylmethyl)-amine

A solution of 10.0 g (40 mmol) 1-diphenylmethyl-azetidin-3-carbonitrile in 20 ml abs. THF is added dropwise to a suspension of 3.1 g (80 mmol) lithium aluminium hydride in 80 ml abs. THF at RT and stirred overnight. The batch is carefully added to 2 ml ethanol and filtered. The filtrate is concentrated under vacuum and dispersed between $CHCl_3$ and water. The aqueous phase is extracted twice, each with 50 ml $CHCl_3$, and the combined organic phases are dried over sodium sulfate and the solvent is removed under vacuum. The residue is chromatographically purified over silica gel with $CHCl_3CH_3OH/NH_4OH$ (90/10/0 to 90/10/1). Yield: 5.6 g (55%) of slowly hardening resin.

Example 5A 3-(1-benzylpiperidin-4-yloxy)-propylamine 10.0 g (40.9 mmol) 3-(1-benzylpiperidin-4-yloxy)-propionitrile are dissolved in 100 ml ethanol and added to a spatula tip of Raney-Nickel. The mixture is stirred at RT under hydrogen atmosphere until the uptake of the theoretical amount of hydrogen (ca. two days). The mixture is filtered from the catalyst and the solvent is removed under vacuum. The residue is distilled in a bulb tube apparatus. Yield of colorless oil: 7.5 g (73%).

Example 6A 1-diphenylmethyl-piperidin-3-carboxylic acid hydrochloride 15.7 g (100 mmol) piperidin-3-carboxylic acid ethyl ester and 30.4 g (220 mmol) potassium carbonate are placed in 100 ml DMF and 24.1 g diphenyl methyl bromide are added dropwise. The mixture is stirred overnight at RT and subsequently filtered. The filtrate is concentrated under vacuum and the residue is taken up with 150 ml acetic acid ethyl ester and extracted twice, each with 50 ml 10% hydrochloric acid. The organic phase is discarded and the combined aqueous phases are made basic with 10%/o sodium hydroxide solution and extracted twice, each with 50 ml acetic acid ethyl ester. The combined organic phases are cooled to ca. 0° C. and the precipitated solid is drawn off and dried. Yield: 20.5 g (63%) of the compound 1-diphenylmethyl-piperidin-3-carboxylic acid ethyl ester with a MP of 166–168° C. This compound is heated to boiling for 8 hours together with 24 ml 20% hydrochloric acid in 100 ml water. After cooling, the precipitate is filtered and crystallized from 70 ml methanol. Yield: 15.6 g (74%).

Example 7A 1-diphenylmethylpiperidin-3-carboxylic acid-(6-amineohexyl)-amide 10.0 g (33.8 mmol) 1-diphenylmethylpiperidin-3-carboxylic acid hydrochloride are reacted analogously to example 6 with 8.6 g (68 mmol) oxalyl chloride to the acid chloride. This is suspended in abs. dichlormethane and added to 6.64 g (30.7 mmol) N-(tert-butoxycarbonyl)-hexanediamine and 3.1 g (30.7 mmol) TEA and stirred at RT overnight. The mixture is subsequently concentrated, taken up in $CHCl_3$ and washed once with 50 ml 10% sodium hydroxide solution and twice with 30 ml water each. The organic phase is dried over sodium sulfate and the solvent is removed under vacuum. The residue is chromatographically purified over silica gel with $CHCl_3/CH_3OH$ (100/0 to 98/2) and dissolved in 80 ml ethanol. After addition of 6 ml conc. hydrochloric acid, the mixture is heated to boiling for 5 hours. After cooling, the solvent is removed under vacuum and the residue is azeotropically dehydrated twice, each with 30 ml toluene, and subsequently dried under high-vacuum. The resin is further processed without additional purification. Yield: 6.8 g (71%).

Example 8A 4-(1-benzylpiperidin-3-yliden)-butyronitrile 77.3 g (188.3 mmol) 3-cyanopropyl-triphenylphosphonium bromide are suspended in 300 ml toluene and added to 22.0 g (191.9 mmol) potassium tert-butylate. The mixture is cooled to ca 0° C. under moisture exclusion and a solution of 34.6 g (182.8 mmol) 1-benzyl-3-piperidone in 50 ml toluene is added dropwise under cooling. The batch is left to stand overnight at ca. 0° C. and subsequently diluted with 200 ml toluene and washed twice, each with 100 ml water. The organic phase is extracted with 150 ml half concentrated hydrochloric acid. Subsequently, the aqueous phase is made basic with 200 ml 10% sodium hydroxide solution and extracted twice, each with 250 ml toluene.

The solvent is removed under vacuum and the residue is chromatographically purified over silica gel with $CHCl_3/CH_3OH$ (97/3). After drawing off the solvent, a light brown oil remains which is processed further without additional purification. Yield: 47.4 g (90%).

Example 9A 4-(1-benzylpiperidin-3-yl)-butylamine 8.0 g (33.3 mmol) 4-(1-benzylpiperidin-3-yliden)-butyronitrile are dissolved in 80 ml ethanol and added to a spatula tip of Raney-Nickel. The mixture is stirred at ca. 50° C. under hydrogen atmosphere until consumption of the theoretischen amount of hydrogen to be taken up (ca. 5 days). The mixture is filtrated from the catalyst and the solvent is removed under vacuum. The residue is chromatographically purified twice over silica gel with $CHCl_3/CH_3OH/NH_4OH$ (90/10/1). After drawing off the solvent, a colorless oil remains which is further processed without additional purification. Yield: 3.9 g (47%).

The active ingredients according to the invention can be processed to the desired medicaments in the form of their acid addition salts, hydrates or solvates individually or in combination with each other, optionally under addition of other active ingredients, for the indications tumor treatment or immunosuppression. In the case of the combination of active ingredients according to the invention with other medicinal forms, these can also optionally be separately present next to each other in the medicine packaging, for example as tablets next to viles, depending on the requirements.

Therefore, further subject-matter of the invention is a method for the treatment of the human or animal body in which a compound or compound mixture according to formula (I), wherein the substituents have the above described meaning, is administered for treatment of tumors and/or as a cytostatic agent, cancerostatic agent, immunosuppressing agent, optionally in combination with further cytostatic or immunosuppressive active ingredients or other active ingredients suitable in the named indications.

Furthermore, the invention relates to a compound or compound mixture according to formula (I) for use in a therapeutic method in which the therapeutic use is carried out in connection with one or more medical indications with tumors or for immunosuppression, optimally in combination with further pharmaceuticals suitable in the named indications.

The use of one or more compounds according to formula (I), including (E)-3-(3-pyridyl)-N-[2-(1-benzylpiperidin-4-yl)ethyl]-2-propenamide hydrochloride, for the production of medicaments for the treatment of the human or animal body, especially in connection with one or more medical indications in the treatment of tumors or for immunosuppression, optimally in combination with further pharmaceuticals suitable in these indications or the use of compounds according to formula (I) in a corresponding diagnosis method represent an embodiment according to the invention.

The respective suitable tumor indications are illustrated in the last section of the description in the discussion of the pharmacological test results.

A method for the production of medicaments with an amount of one or more compounds according to formula (I) which are suitable for the processing of these active ingredients together with respective suitable pharmaceutically acceptable carriers and adjuvants for finished medicinal forms equally belongs to the scope of protection according to the invention.

Depending on the medical indication being considered, the respective suitable medical form is selected for the suitable therapeutic application.

The invention also relates to the use of the compounds according to formula (I), including (E)-3-(3-pyridyl)-N-[2-(1-benzylpiperidin-4-yl)ethyl]-2-propenamide hydrochloride, for treatment in the above indications.

The production of the respective suitable medicaments as well as a series of examples of medicinal forms are described in the following for better understanding of the invention.

Therapeutic Administration Forms

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvants and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micells, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as substances for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxyethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvants such as for example gelatin, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzyl alcohol, anti-oxidants, such as for example sodium sulfite and stabilizers, such as for example EDTA, are suitable as adjuvants and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvants, dispersion agents are also suitable. For production of lyophilisates, builders are also used, such as for example mannite, dextran, saccharose, human albumin, lactose, PVP or gelatin varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatin capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatin capsules.

Anti-stick and lubricant and separating agents, dispersion agents such as flame dispersed silicone dioxide, disintegrants, such as various starch types, PVC, cellulose esters as granulating or retarding agents, such as for example wax-like and/or polymeric compounds on the basis of Eudragit®, cellulose or Cremophor® are used as a further adjuvants for the production of compressives, such as for example tablets or hard and soft gelatin capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminum stearate, calcium stearate, talc, siliconized talc, stearic acid, acetyl alcohol and hydrated fats are used.

In this connection, oral therapeutic systems constructed especially on osmotic principles, such as for example GIT (gastrointestinal therapeutic system) or OROS (oral osmotic system), are also to be mentioned.

Effervescent tablets or tabs. both of which represent immediately drinkable instant medicinal forms which are quickly dissolved or suspended in water are among the perorally administratable compressives. Among the perorally administratable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspisated juices which are formulated with water before ingestion. Ion exchange resins in combination with one or more active ingredients are also to be mentioned for the production of liquid ingestible forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatin or other carriers.

Hardened fat, such as for example Witepsol®, Massa Estarinum®, Novata®, coconut fat, glycerol-gelatin masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvants and carriers. Aside from suitable adjuvants and carriers such as solvents and polymeric components, for example based on Eudragit®, membrane infiltration increasing substances and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration installation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the administration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or cellulose derivatives, such as for example guar or xanthene gum, inorganic gel builders, such as for example aluminum hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvants and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and vaseline.

Anionic, cationic or neutral tensides can be employed as emulsifiers, for example alkalized soaps, methyl soaps, amine soaps, sulfanated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, Tris-buffer or triethanol amine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administeration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and/or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvants, such as for example isopropyl myristate, polyoxyethylene sorbitan fatty acid ester, sorbitan trioleate, lecithins or soya lecithin.

For regional application in situ, solutions for installation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments:

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984), 5th edition;

P. H. List, Arzneimformenlehre, Wissenschaftliche Verlagsgesellschaft mbH, Stuttgart, (1985), 4th edition;

H. Sucker, P. Fuchs, P. Speiser, Pharmazeutische Technologie, Georg Thieme Verlag, Stuttgart-New York, (1991), 2nd edition;

A. T. Florence, D. Attwood, Physicochemical Principles of Pharmacy, The Maximillan Press Ltd., Hong Kong, (1981);

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York-Basel, (1987);

K. E. Avis, L. Lachmann, H. A. Liebermann, Pharmaceutical Dosage Forms: Parenteral Medications, volume 2, Marcel Dekker Inc., New York-Basel, (1986);

B. W. Müller, Controlled Drug Delivery, Paperback APV, volume 17, Wissenschaftliche Verlagsgesellschaft mbH, Stuttgart, (1987);

H. Asch, D. Essig, P. C. Schmidt, Technologie von Salben, Suspensionen und Emulsionen, Wissenschaftliche Verlagsgesellschaft mbK, Stuttgart, (1984);

H. A. Liebermann, L. Lachman, J. B. Schwartz, Pharmaceutical Desage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam-London-New York-Tokyo, (1994);

J. T. Carstensen, Pharmaceutical Principles of Solid Dosage Forms, Technomic Publishing Co., Inc., Lancaster-Basel, (1993).

PRODUCTION EXAMPLES

1. Injection Therapeutics a) Parenteral Solution

| | |
|---|---|
| active ingredient used according to the invention | 5.000 g |
| acid sodium phosphate | 5.000 g |
| sodium tartrate | 12.000 g |
| benzyl alcohol | 7.500 g |
| water for injection purposes | to 1000.000 ml |

The solution is produced according to the customary method, sterilized and filled into 10 ml vials. One vial contains 50 mg of the compound according to the invention.

b) Penteral Solution

| | |
|---|---|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring; the medicinal form is adjusted to a suitable pH value by acid addition and subsequently filled into 100 ml vials and sterilized. A vial contains 100 mg of the compound according to the invention.

c) Parenteral Dispersion

| | |
|---|---|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

d) Biodegradable Parenteral Depot Medicinal Form

| | |
|---|---|
| active ingredient used according to the invention | 10.000 |
| polylactic acid /polygylcolic acid polymer | 70.000 |
| polyvinylpyrrolidone | 0.200 |
| gelatin | 2.000 |
| soya lecithin | 2.000 |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvant solution, which is also produced in a sterile manner, is filled. The biodegradable microparticles are mixed with the dispersion agent shortly before application and dispersed. A ready-made syringe contains 200 mg of the active compound according to the invention.

e) Parenteral Dispersion for Subcutaneous Installation

| | |
|---|---|
| active ingredient used according to the invention | 25,000 g |
| soya lecithin | 25,000 g |
| arachis oil | 400,000 g |
| benzyl alcohol | 50,000 g |
| Miglyole ® | to 1000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so called perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvants, possibly in combination with further medicinal agents suitable for the mentioned indications.

2. Solid, Peroral Administration Medicaments a) Tablets

| | |
|---|---|
| active ingredient used according to the invention | 10,000 g |
| lactose | 5,200 g |
| starch, soluble | 1,800 g |
| hydroxypropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

b) Coated Tablet Core

| | |
|---|---|
| active ingredient used according to the invention | 10,000 g |
| flame dispersed silicon dioxide | 500 g |
| corn starch | 2,250 g |
| stearic acid | 350 g |
| ethanol | 3.0 l |
| gelatin | 900 g |
| purified water | 10.0 l |
| talcum | 300 g |
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

c) Drink Suspension in Vials

| | |
|---|---|
| active ingredient used according to the invention | 0.050 g |
| glycerin | 0.500 g |
| sorbite, 70% solution | 0.500 g |
| sodium saccharinate | 0.010 g |
| methyl-p-hydroxybenzoate | 0.040 g |
| aromatic agent | q.s. |
| sterile wasser | q.s. to 5 ml |

The above-mentioned components are mixed in a customary manner to a suspension and filled in a suitable drink vial having 5 ml content.

d) Poorly Soluble Sublingual Tablets

| | |
|---|---|
| active ingredient used according to the invention | 0.030 g |
| lactose | 0.100 g |
| stearic acid | 0.004 g |
| talcum purum | 0.015 g |
| sweetener | q.s. |
| aromatic agent | q.s. |
| rice starch | q.s. to 0.500 g |

The active ingredient is compacted together with the adjuvants under high pressure to sublingual tablets, favorably in oblong form.

e) Soft Gel Capsule

| | |
|---|---|
| active ingredient used according to the invention | 0.050 g |
| fatty acid glyceride mixture (Miglyole ®) | q.s. to 0.500 g |

The active ingredient is impasted together with the fluid carrier mixture and mixed together with further adjuvants suitable for the incapsulation and filled into elastic soft gelatin capsules which are sealed.

f) Hard Gelatin Capsules

| | |
|---|---|
| active ingredient used according to the invention | 0.150 g |
| microcrystalline cellulose | 0.100 g |
| hydroxypropylmethylcellulose | 0.030 g |
| mannite | 0.100 g |
| ethylcellulose | 0.050 g |
| triethyl citrate | 0.010 g |

The active ingredient is mixed together with the adjuvants, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatin capsule contains 150 mg of active ingredient.

3. Topically Administratable Medicinal Forms a) Hydrophilic Ointment

| | |
|---|---|
| active ingredient used according to the invention | 0.500 g |
| Eucerinum ® anhydricum | 60.000 g |
| microcrystalline wax | 15.000 g |
| vaseline oil | q.s. to 100.000 g |

The above-mentioned adjuvants are melted and further processed together with the active ingredient to an ointment in a customary manner.

b) Lipophilic Ointment

| | |
|---|---|
| active ingredient used according to the invention | 10.000 g |
| propylene glycol | 50.000 g |
| paraffin, liquid | 100.000 g |
| paraffin wax | 100.000 g |
| vaseline | to 1000.000 ml |

The active ingredient(s) used according to the invention is dissolved in propylene glycol at ca. 60° C. At the same time, the lipophilic components are melted at 60–70° C. and subsequently combined with the active ingredient solution. The ointment is emulsified at first at 60–70° C. and subsequently cooled to 35–40° C. under constant emulsification and then filled in 10 g tubes A tube contains 100 mg of the compound according to the invention.

4. Inhalation Therapeutic

Further subject-matter is a pharmaceutical formulation which is characterized in that it contains an active ingredient(s) used according to the invention as a base or a physiologically acceptable salt thereof together with carriers and/or diluents customary for this and suitable for administration by means of inhalation.

In connection with the production of the medicaments, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4 chlorobenzoate, p-tosylate, methaneosulfonate, ascorbate, salicylate, acetate, formate, succinate, lactate, glutarate, gluconate or tricarballylate.

The administration of the active ingredient(s) used of the invention by means of inhalation occurs according to the invention in conventional ways customary for administrations of this form, for example in the form of a commercial controlled dosage aerosol or in combination with a spacer. In controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however, non-fluorinated hydrocarbons or other propellants which are gaseous at normal pressure and room temperature, such as propane, butane or dimethyl ether, can be preferred. Thereby, propellant-free manual pump systems or dry powder systems as described below can also be used.

Suitably, the propellant aerosols can also contain surface active adjuvants, such as for example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient-soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredient(s) used according to the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (as controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

|  | Intended dose per stroke | per aerosol % by weight |
|---|---|---|
| a) Controlled Dosage Aerosol | | |
| active ingredient used according to the invention | 0.500 mg | 0.66 |
| stabilizer | 0.075 mg | 0.10 |
| HFC 134a | 75.500 mg | 99.24 |
| b) Controlled Dosage Aerosol | | |
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings. Alternatively, the suspension can also be produced in a suitable cooled stabilizer solution in HFC 134a/227.

The examples c) to d) describe the composition and production of dosage dry powder formulations.

|  | mg/dose |
|---|---|
| c) Dosage-Dry Powder Formulation | |
| active ingredient used according to the invention | 0.500 mg |
| d) Dosage-Dry Powder Formulation | |
| active ingredient used according to the invention | 0.500 mg |
| lactose Ph.Eur. | to 2.5 mg or to 5.0 mg |
| e) Dosage-Dry Powder Formulation | |
| active ingredient used according to the invention | 0.250 mg |
| lactose Ph.Eur. | to 2.5 mg or to 5.0 mg |

In example c) the active ingredient is formulated after micronization under addition of steam as pellets with an MMAD between 0,1 and 0,3 mm diameter and brought to use in a multi-dose powder applicator.

In the examples d) and e) the active ingredient is micronized, thereafter, bulk material is mixed with the lactose in the given amounts, and subsequently, filled in a multi-dose powder inhilator.

In all of the examples set forth above, the active ingredient or the medicinal agent in the form of the respective suitable pharmaceutical acceptable salt and/or acid addition salts can be present, insofar as the base is not preferred in each case.

In the following, the pharmaceutical test results obtained in connection with the newly found indications based, in a representative manner, on the specifically structured new compounds are described.

Pharmaceutical Experimental Section 1. Growth Inhibition of Human Tumor Cells The tumor growth inhibiting activity of the substances was determined on human tumor cells in standardized in vitro test systems. In the screening tests, the substances gave $IC_{50}$-values in a concentration range of 0.1 nM to 10 µM.

Example:

HepG2 cells plated at a 20,000 cell/ml in 12-well plastic dishes. Cultivation occured in Richters IMEM-ZO nutrient medium with 5% fetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [µM] |
|---|---|
| 136 | 0.002 |
| 153 | 0.002 |
| 159 | 0.0005 |
| 178 | 0.0007 |
| 199 | 0.001 |

2. Indications

The compounds of formula (I) and their salts permit a therapeutic use in malignant illnesses of humans and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynecological tumors, such as of the uterus or the vagina, ovarian carcinomas, testicle tumors, prostate carcinomas, skin cancer, kidney cancer, bladder tumors, esophagus carcinomas, stomach cancer, rectal carcinomas, pancreas carcinomas, thyroid cancer, adrenal tumors, leukemia and lymphomas, Hodgkin's disease, tumor illnesses of the CNS, soft-tissue sarcomas, bone sarcomas, benign and malignant mesotheliomas, but especially intestine cancer, liver cancer, breast cancer, bronchial and lung carcinomas, melanomas, acute and chronic leukemias. Benign papillomatosis tumors are also considered for therapy with the named substances.

The novel structural class of compounds possesses an independent activity profile in the effectiveness against the various tumor types. Thus, tumors which are resistant to customary cytostatic agents, for example, can respond entirely to these substances. In addition, based on the independent characteristics, combinations of the new compounds with known chemo-therapeutically used pharmaceuticals or other methods of treatment are considered as long as their properties are complimented in a suitable manner. The integration of the presently used compounds with their specific structures in a therapy scheme is successful with one or more substances from the following classes for example: anti-metabolites (for example cytarabine, 5-fluorouracil, 6-mercaptopurine, methotrexate), alkylating agents (for example busulfan, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecan, irinotecan), spindle poisons (for example vincristine, navelbin, taxol, taxoter), hormonally active agents (for example tamoxifen, flutamide, formestan, goserelin) or other cytostatic agents with complex modes of action (for example L-asparaginase, bleomycin, hydroxyurea). Resistant tumor cells can be made sensitive again by interaction of the new compounds with a mechanism of resistance for common cytostatic agents (for example P-glycoprotein, MRP, glutathione-S-transferase, metallothionein). A combination is also applicable with radiation therapy, hyperthermia or immunotherapy, for example.

3. Immuno Suppressing Activity

Many anti-tumor agents have not only a cytotoxic effect on tumor cells, but also on the blood cell system. This leads to a weakening of the immune defense, which can, in turn, be specifically employed to suppress the rejection reaction after an organ transplantation for example. Therefore, a use of the main compounds, optionally in combination with other compounds effective for these indications is suitable in diseases such as psoriasis or autoimmune diseases. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell suspension over a ficoll gradient and taken up in IMEM-ZO culture medium with 0,1% dextran 70,000 and 2% fetal calf serum. The cells were plated at a density of ca. 500,000 cells/well/ml in a 12-well plate, 1 ml doubly concentrated test substance solution was pipetted per well and this was subsequently incubated in a tissue culture incubator at 37° C. and 5% $CO_2$. After 2 days, a 1 ml-aliquot with 5 µl of the fluorescent dye solutions propidium iodide (8 mg/ml) and 3,3'-dihexyloxacarbocyanin iodide (40 µg/ml) each was added per well, and incubated for 3 minutes at room temperature. Subsequently, 10,000 cells per each sample were measured on a flow-through cytometer and the percentage amount of vital cells in the population was determined. By means of the dose-response curves, $IC_{50}$-values were calculated which were also employed in the following Tables for the characterization of the individual substances:

| Test Substance No. | $IC_{50}$ [µM] |
|---|---|
| 150 | 0.0002 |
| 153 | 0.00008 |
| 159 | 0.003 |
| 195 | 0.002 |
| 199 | 0.00004 |

The independent class of the compounds used according to the invention also permits an efficient combination with known immunosuppressive agents such as for example cyclosporin A, tacrolimus, rapamycin, azathioprin and glucocorticoids.

The invention is in no way limited to the present respective concretely named active ingredient concentrations, dosages, combinations with one or more other cytostatic agents, tumor inhibitors, cancerostatic agents, immunosuppressive agents or further medicinal agents suitable for the respective specific indications or the type of tumor to treated or immunological illness, etc.

The invention claimed is:

1. A compound selected from the group consisting of N-[4-(1-methylsulfonylpiperidin-4-yl)-butyl]-3-(pyridin-3-yl)-acrylamide, N-{4-[1-(2-naphthylsulfonyl)-piperidin-4-yl]-butyl}-3-(pyridin-3-yl)-acrylamide, N-{4-[1-(2-naphthylsulfonyl)-piperidin-4-yl]-butyl}-5-(pyridin-3-yl)-2,4-pentadienoic acid amide, N-{4-[1-(1-naphthylaminocarbonyl)-piperidin-4-yl]-butyl}-3-(pyridin-3-yl)-acrylamide, N-[4-(1-diphenylaminocarbonyl-piperidin-4-yl)-butyl]-3-(pyridin-3-yl)-acrylamide, N-[4-(1-diphenylaminocarbonyl-piperidin-4-yl)-butyl]-5-(pyridin-3-yl)-2,4-pentadienoic acid amide, N-{4-[1-(10,11-dihydrodibenzo[b,f]azepin-5-yl-carbonyl)-piperidin-4-yl]-butyl}-3-(pyridin-3-yl)-acrylamide, and N-[4-(1-diphenylphosphinoyl-piperidin-4-yl)-butyl]-3-(pyridin-3-yl)-acrylamide, and a pharmaceutically acceptable acid addition salt thereof.

2. A compound selected from the group consisting of N-[4-(1-acetylpiperidin-4-yl)-butyl]-3-(pyridin-3-yl)-acrylamide, N-[4-(1-diphenylacetyl-piperidin-4-yl)-butyl]-3-(pyridin-3-yl)-acrylamide, N-{4-[1-(3,3-diphenylpropionyl)-piperidin-4-yl]-butyl}-3-(pyridin-3-yl)-acrylamide, N-[4-(1-benzoylpiperidin-4-yl)-butyl]-3-(pyridin-3-yl)-acrylamide, N-[4-(1-benzoylpiperidin-4-yl)-butyl]-5-(pyridin-3-yl)-2,4-pentadienoic acid amide, and N-{4-[1-(9-oxo-9H-fluoren-4-yl-carbonyl)-piperidin-4-yl]-butyl}-3-(pyridin-3-yl)-acrylamide, and a pharmaceutically acceptable acid addition salt thereof.

3. A compound selected from the group consisting of N-{4-[1-(phenylpyridin-3-yl-methyl)-piperidin-4-yl]-butyl}-3-(pyridin-3-yl)-acrylamide, N-{4-[1-(phenylpyridin-4-yl-methyl)-piperidin-4-yl]-butyl}-3-(pyridin-3-yl)-acrylamide, N-{4-[1-(6,11-dihydrodibenzo[b,e]oxepin-11-yl)-piperidin-4-yl]-butyl}-3-(pyridin-3-yl)-acrylamide and N-{4-[1-(6,11-dihydrodibenzo[b,e]thiepin-11-yl)-piperidin-4-yl]-butyl}-3-(pyridin-3-yl)-acrylamide, and a pharmaceutically acceptable acid addition salt thereof.

4. A compound selected from the group consisting of N-[7-(1-diphenylmethylpiperidin-4-yl)-heptyl]-3-(pyridin-3-yl)-acrylamide, N-[8-(1-diphenylmethylpiperidin-4-yl)-octyl]-3-(pyridin-3-yl)-acrylamide, N-[3-(1-diphenylmethylpiperidin-4-yloxy)-propyl]-3-(pyridin-3-yl)-acrylamide, and N-[3-(1-benzylpiperidin-4-yloxy)-propyl]-3-(pyridin-3-yl)-acrylamide and a pharmaceutically acceptable acid addition salt thereof.

5. A compound selected from the group consisting of N-[2-(1-diphenylmethylpiperidin-4-yl)-ethyl]-5-(pyridin-3-yl)-2,4-pentadienoic acid amide, N-[4-(1-diphenylmethylpiperidin-4-yl)-butyl]-5-(pyridin-3-yl)-2,4-pentadienoic acid amide, N-[5-(1-diphenylmethylpiperidin-4-yl)-pentyl]-5-(pyridin-3-yl)-2,4-pentadienoic acid amide and N-[6-(1-diphenylmethylpiperidin-4-yl)-hexyl]-5-(pyridin-3-yl)-2,4-pentadienoic acid amide and a pharmaceutically acceptable acid addition salt thereof.

6. A compound of formula (I) or a pharmaceutically acceptable acid addition salt of formula (I)

$$R^1 \text{-pyridine-} A\text{-}\underset{\|}{C}(=O)\text{-}N(R^4)\text{-}D\text{-}E\text{-}G \quad (I)$$
(with pyridine N-oxide $(O)_k$)

the compound of formula (I) being selected from the group consisting of $R^1 = H$, $k = 0$, $A = CH=CH$, $R^4 = H$, and
$DEG = CH_2CH_2$—piperidine—NH, $R^1 = H$, $k = 0$, $A = CH=CH$, $R^4 = H$, and
$DEG = CH_2CH_2CH_2CH_2$—piperidine—NH, $R^1 = H$, $k = 0$, $A = CH=CH-CH=CH$, $R^4 = H$, and
$DEG = CH_2CH_2CH_2CH_2$—piperidine—NH, $R^1 = H$, $k = 0$, $A = CH=CH$, $R^4 = H$, and
$DEG = CH_2CH_2CH_2O$—piperidine—N—H, $R^1 = H$, $k = 0$, $A = CH=CH$, $R^4 = H$, and
$DEG = CH_2CH_2CH_2CH_2CH_2CH_2$—piperidine—NH, $R^1 = H$, $k = 0$, $A = CH=CH-CH=CH$, $R^4 = H$, and
$DEG = -CH_2CH_2$—piperidine—$N$—$CH_3$, $R^1 = H$, $k = 0$, $A = CH=CH-CH=CH$, $R^4 = H$, and
$DEG = CH_2CH_2CH_2CH_2$—piperidine—$N$—CH($CH_3$)$_2$, $R^1 = H$, $k = 0$, $A = CH=CH(CH_2)_2$, $R^4 = H$, and
$DEG = CH_2CH_2CH_2CH_2$—piperidine—$N$—cyclopropyl, $R^1 = H$, $k = 0$, $A = CH=CH$, $R^4 = H$, and
$DEG = CH_2CH_2NH\text{-}\underset{\|}{C}(=O)\text{-}O$—piperidine—$N$—cyclohexyl, $R^1 = H$, $k = 0$, $A = CH=C-CN$, $R^4 = H$, and
$DEG = CH_2CH_2$—piperidine—$N$—CH$_2$-cyclopropyl, -continued R¹ = H, k = 0, A = CH=CH, R⁴ = H, and

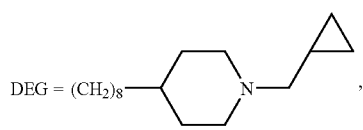

R¹ = H, k = 0, A = CH=CH, R⁴ = H, and

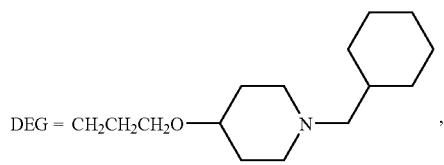

R¹ = H, k = 0, A = CH=CH, R⁴ = H, and

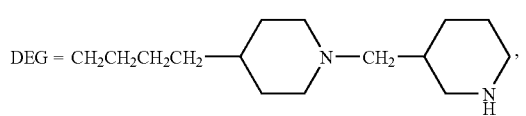

R¹ = H, k = 0, A = CH=CH, R⁴ = H, and

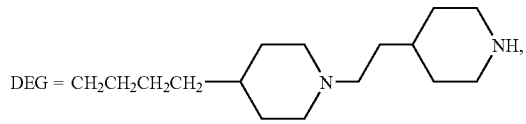

R¹ = H, k = 0, A = CH=CH, R⁴ = H, and

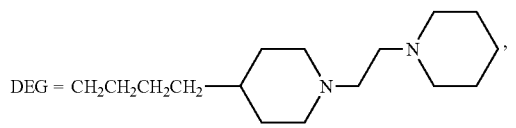

R¹ = H, k = 0, A = CH=CH, R⁴ = H, and

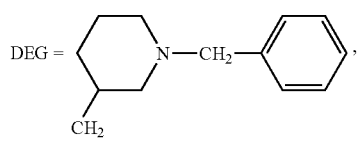

R¹ = H, k = 0, A = CH=CH, R⁴ = H, and

R¹ = H, k = 0, A = CH=CH—CH=CH, R⁴ = H, and

R¹ = H, k = 1, A = CH=CH, R⁴ = H, and

DEG = CH₂CH₂CH₂CH₂—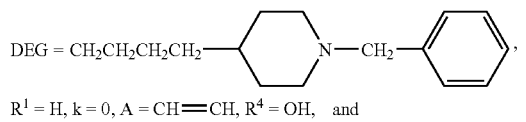,

R¹ = H, k = 0, A = CH=CH, R⁴ = OH, and

DEG = CH₂CH₂CH₂CH₂—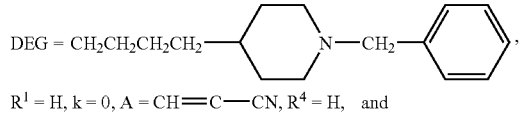,

R¹ = H, k = 0, A = CH=C—CN, R⁴ = H, and

DEG = CH₂CH₂CH₂CH₂—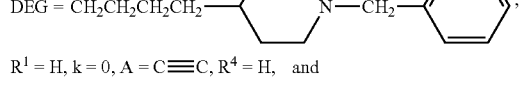,

R¹ = H, k = 0, A = C≡C, R⁴ = H, and

-continued

DEG = CH₂CH₂CH₂CH₂—[piperidine]—CH₂—[phenyl],

R¹ = H, k = 0, A = CH=CH(CH₂)₂, R⁴ = H, and

DEG = CH₂CH₂CH₂CH₂—[piperidine]—CH₂—[phenyl],

R¹ = H, k = 0, A = CH=CH—CH=CH, R⁴ = H, and

DEG = CH₂CH₂CH₂CH₂—[piperidine]—CH₂—[phenyl],

R¹ = 2-F, k = 0, A = CH=CH—CH=CH, R⁴ = H, and

DEG = CH₂CH₂CH₂CH₂—[piperidine]—CH₂—[phenyl],

R¹ = H, k = 0, A = (CH=CH)₃, R⁴ = H, and

DEG = CH₂CH₂CH₂CH₂—[piperidine]—CH₂—[phenyl],

R¹ = H, k = 0, A = CH=CH, R⁴ = H, and

DEG = CH₂CH₂CH₂O—[piperidine]—CH₂—[phenyl],

R¹ = H, k = 0, A = CH=CH, R⁴ = H, and

DEG = CH₂CH₂CH₂CH₂—[3-piperidine]—CH₂—[phenyl],

R¹ = H, k = 0, A = CH=CH, R⁴ = H, and

DEG = CH₂CH₂CH₂CH₂—[tetrahydropyridine]—CH₂—[phenyl],

R¹ = H, k = 0, A = CH=CH, R⁴ = H, and

DEG = CH₂CH₂CH₂CH₂—[4-CH₃-piperidine]—CH₂—[phenyl],

R¹ = H, k = 0, A = CH=CH, R⁴ = H, and

DEG = CH₂CH₂CH₂CH₂—[4-OH-piperidine]—CH₂—[phenyl],

R¹ = H, k = 0, A = CH=CH, R⁴ = H, and

DEG = CH₂CH₂CH₂CH₂—[2-oxo-piperidine]—CH₂—[phenyl],

R¹ = H, k = 0, A = CH=CH—CH=CH, R⁴ = H, and

DEG = CH₂CH₂CH₂CH₂—[piperidine]—CH₂—[phenyl]—OH,

R¹ = H, k = 0, A = CH=CH—CH=CH, R⁴ = H, and

DEG = CH₂CH₂CH₂CH₂—[piperidine]—CH₂—[phenyl]—OCH₃,

R¹ = H, k = 0, A = CH=CH—CH=CH, R⁴ = H, and

-continued

DEG = CH₂CH₂CH₂CH₂—[piperidine]—N—CH₂—[biphenyl], $R^1 = H$, $k = 0$, $A = CH=CH-CH=CH$, $R^4 = H$, and DEG = CH₂CH₂—[piperidine]—N—CH₂—[anthracenyl], $R^1 = H$, $k = 0$, $A = C\equiv C$, $R^4 = H$, and DEG = CH₂CH₂CH₂CH₂—[piperidine]—N—CH(phenyl)(cyclohexyl), $R^1 = H$, $k = 0$, $A = CH=CH$, $R^4 = H$, and DEG = [3-(CH₂CH₂)-piperidine]—N—CH₂—[4-pyridyl], $R^1 = H$, $k = 0$, $A = CH=CH-CH=CH$, $R^4 = H$, and DEG = CH₂CH₂CH₂CH₂—[piperidine]—N—CH₂—[3-pyridyl], $R^1 = H$, $k = 0$, $A = CH=CH$, $R^4 = H$, and DEG = CH₂CH₂CH₂CH₂—[piperidine]—N—CH₂—[benzofurazanyl], $R^1 = H$, $k = 0$, $A = CH=CH$, $R^4 = H$, and DEG = CH₂—[piperidine]—N—CH(C₆H₅)₂, $R^1 = H$, $k = 0$, $A = CH=CH-CH=CH$, $R^4 = H$, and DEG = CH₂—[piperidine]—N—CH(C₆H₅)₂, $R^1 = H$, $k = 1$, $A = CH=CH$, $R^4 = H$, and DEG = CH₂CH₂—[piperidine]—N—CH(C₆H₅)₂, $R^1 = H$, $k = 0$, $A = CH=CH(CH₂)_2$, $R^4 = H$, and DEG = CH₂CH₂—[piperidine]—N—CH(C₆H₅)₂, $R^1 = H$, $k = 0$, $A = CH=CHCH_2CHF$, $R^4 = H$, and DEG = CH₂CH₂—[piperidine]—N—CH(C₆H₅)₂, $R^1 = H$, $k = 0$, $A = CH=CH$, $R^4 = H$, and DEG = NH—C(=O)—[piperidine]—N—CH(C₆H₅)₂, $R^1 = H$, $k = 0$, $A = CH=CH$, $R^4 = H$, and DEG = [3-(CH₂CH₂)-piperidine]—N—CH(C₆H₅)₂, $R^1 = H$, $k = 0$, $A = CH=CH-CH=CH$, $R^4 = H$, and DEG = CH₂CH₂CH₂—[piperidine]—N—CH(C₆H₅)₂, $R^1 = H$, $k = 0$, $A = CH=CH$, $R^4 = H$, and DEG = CH₂CH₂NH—[piperidine]—N—CH(C₆H₅)₂, $R^1 = H$, $k = 1$, $A = CH=CH$, $R^4 = H$, and DEG = CH₂CH₂CH₂CH₂—[piperidine]—N—CH(C₆H₅)₂, $R^1 = H$, $k = 0$, $A = CH=CH$, $R^4 = OH$, and DEG = CH₂CH₂CH₂CH₂—[piperidine]—N—CH(C₆H₅)₂, $R^1 = H$, $k = 0$, $A = CH=C-CN$, $R^4 = H$, and DEG = CH₂CH₂CH₂CH₂—[piperidine]—N—CH(C₆H₅)₂, $R^1 = H$, $k = 0$, $A = C\equiv C$, $R^4 = H$, and DEG = CH₂CH₂CH₂CH₂—[piperidine]—N—CH(C₆H₅)₂, $R^1 = H$, $k = 0$, $A = CH=CH(CH_2)_2$, $R^4 = H$, and DEG = CH₂CH₂CH₂CH₂—[piperidine]—N—CH(C₆H₅)₂, $R^1 = H$, $k = 0$, $A = CH=CHCHCF_2$ (OH), $R^4 = H$, and DEG = CH₂CH₂CH₂CH₂—[piperidine]—N—CH(C₆H₅)₂, $R^1 = H$, $k = 0$, $A = (CH_2)_2CH=CH$, $R^4 = H$, and DEG = CH₂CH₂CH₂CH₂—[piperidine]—N—CH(C₆H₅)₂, $R^1 = H$, $k = 0$, $A = CH=CH-CH=CH$, $R^4 = H$, and -continued DEG = CH₂CH₂CH₂CH₂—[piperidine]—CH(C₆H₅)₂,
R¹ = H, k = 0, A = CH=CH—CH=CH, R⁴ = CH₃, and DEG = CH₂CH₂CH₂CH₂—[piperidine]—CH(C₆H₅)₂,
R¹ = 2-F, k = 0, A = CH=CH—CH=CH, R⁴ = H, and DEG = CH₂CH₂CH₂CH₂—[piperidine]—CH(C₆H₅)₂,
R¹ = 2-F, k = 0, A = CH=CH—CH=CH, R⁴ = OH, and DEG = CH₂CH₂CH₂CH₂—[piperidine]—CH(C₆H₅)₂,
R¹ = 4-F, k = 0, A = CH=CH—CH=CH, R⁴ = H, and DEG = CH₂CH₂CH₂CH₂—[piperidine]—CH(C₆H₅)₂,
R¹ = 5-F, k = 0, A = CH=CH—CH=CH, R⁴ = H, and DEG = CH₂CH₂CH₂CH₂—[piperidine]—CH(C₆H₅)₂,
R¹ = 6-F, k = 0, A = CH=CH—CH=CH, R⁴ = H, and DEG = CH₂CH₂CH₂CH₂—[piperidine]—CH(C₆H₅)₂,
R¹ = 2-Cl, k = 0, A = CH=CH—CH=CH, R⁴ = H, and DEG = CH₂CH₂CH₂CH₂—[piperidine]—CH(C₆H₅)₂,
R¹ = 6-CH₃, k = 0, A = CH=CH—CH=CH, R⁴ = H, and DEG = CH₂CH₂CH₂CH₂—[piperidine]—CH(C₆H₅)₂,
R¹ = 2-OH, k = 0, A = CH=CH—CH=CH, R⁴ = H, and DEG = CH₂CH₂CH₂CH₂—[piperidine]—CH(C₆H₅)₂,
R¹ = H, k = 0, A = (CH=CH)₃, R⁴ = H, and DEG = CH₂CH₂CH₂CH₂—[piperidine]—CH(C₆H₅)₂,
R¹ = H, k = 0, A = CH=CH, R⁴ = H, and DEG = [3-substituted piperidine]—CH(C₆H₅)₂, with CH₂CH₂CH₂ at 3-position
R¹ = 2-F, k = 0, A = CH=CH, R⁴ = H, and DEG = [3-substituted piperidine]—CH(C₆H₅)₂, with CH₂CH₂CH₂CH₂ at 3-position
R¹ = 5-F, k = 0, A = CH=CH, R⁴ = H, and DEG = [3-substituted piperidine]—CH(C₆H₅)₂, with CH₂CH₂CH₂CH₂ at 3-position
R¹ = 6-CH₃O, k = 0, A = CH=CH, R⁴ = H, and DEG = [3-substituted piperidine]—CH(C₆H₅)₂, with CH₂CH₂CH₂CH₂ at 3-position
R¹ = H, k = 0, A = CH=CH—CH=CH, R⁴ = H, and DEG = [3-substituted piperidine]—CH(C₆H₅)₂, with CH₂CH₂CH₂CH₂ at 3-position
R¹ = H, k = 0, A = CH=CH, R⁴ = H, and DEG = CH₂CH₂CH₂O—[piperidine]—CH(C₆H₅)₂,
R¹ = H, k = 0, A = CH=CH—CH=CH, R⁴ = H, and DEG = CH₂CH₂CH₂O—[piperidine]—CH(C₆H₅)₂,
R¹ = H, k = 0, A = CH=CH, R⁴ = H, and DEG = CH₂CH₂NH—C(=O)—[piperidine]—CH(C₆H₅)₂,
R¹ = H, k = 0, A = CH=CH, R⁴ = H, and DEG = CH₂CH₂CH₂CH=[piperidine]—CH(C₆H₅)₂,
R¹ = H, k = 0, A = CH=CH, R⁴ = H, and DEG = CH₂CH=CHCH₂—[piperidine]—CH(C₆H₅)₂,
R¹ = H, k = 0, A = CH=CH, R⁴ = H, and DEG = CH₂C≡CCH₂—[piperidine]—CH(C₆H₅)₂,
R¹ = H, k = 0, A = CH=CH, R⁴ = H, and DEG = CH₂CH₂CH₂CH₂—[tetrahydropyridine]—CH(C₆H₅)₂,
R¹ = H, k = 0, A = CH=CH—CH=CH, R⁴ = H, and DEG = CH₂CH₂CH₂CH₂CH₂—[piperidine]—CH(C₆H₅)₂,
R¹ = H, k = 0, A = CH=CH, R⁴ = H, and DEG = CH₂CH₂CH₂OCH₂—[piperidine]—CH(C₆H₅)₂,
R¹ = H, k = 0, A = CH=CH—CH=CH, R⁴ = H, and DEG = CH₂CH₂CH₂OCH₂—[piperidine]—N—CH(C₆H₅)₂, R¹ = H, k = 0, A = CH=CH, R⁴ = H, and DEG = OCH₂CH₂CH₂—[piperidine]—N—CH(C₆H₅)₂, R¹ = H, k = 0, A = CH=CH, R⁴ = H, and DEG = CH₂CH₂NH—C(=O)—O—[piperidine]—N—CH(C₆H₅)₂, R¹ = H, k = 0, A = CH=CH—CH=CH, R⁴ = H, and DEG = CH₂CH₂CH₂CH₂CH₂CH₂—[piperidine]—N—CH(C₆H₅)₂, R¹ = H, k = 0, A = CH=CH, R⁴ = H, and DEG = CH₂CH₂CH₂OCH₂CH₂—[piperidine]—N—CH(C₆H₅)₂, R¹ = H, k = 0, A = CH=CH, R⁴ = H, and DEG = CH₂CH₂CH₂CH₂NH—C(=O)—[piperidine]—N—CH(C₆H₅)₂, R¹ = H, k = 0, A = CH=CH, R⁴ = H, and DEG = (CH₂)₇—[piperidine]—N—CH(C₆H₅)₂, R¹ = H, k = 0, A = CH=CH, R⁴ = H, and DEG = (CH₂)₈—[piperidine]—N—CH(C₆H₅)₂, R¹ = H, k = 0, A = CH=CH, R⁴ = H, and DEG = (CH₂)₆NH—C(=O)—[piperidine]—N—CH(C₆H₅)₂, R¹ = H, k = 0, A = CH=CH, R⁴ = H, and DEG = CH₂CH₂CH₂CH₂—[3-methylpiperidine]—N—CH(C₆H₅)₂, R¹ = H, k = 0, A = CH=CH, R⁴ = H, and DEG = CH₂CH₂CH₂CH₂—[4-hydroxypiperidine]—N—CH(C₆H₅)₂, R¹ = H, k = 0, A = CH=CH, R⁴ = H, and DEG = CH₂CH₂CH₂CH₂—[2-oxopiperidine]—N—CH(C₆H₅)₂, R¹ = H, k = 0, A = CH=CH—CH=CH, R⁴ = H, and DEG = CH₂CH₂CH₂CH₂—[piperidine]—N—CH(4-F-C₆H₄)(4-F-C₆H₄), R¹ = H, k = 0, A = C≡C, R⁴ = H, and DEG = CH₂CH₂CH₂CH₂—[piperidine]—N—CH(4-Cl-C₆H₄)(4-Cl-C₆H₄), R¹ = H, k = 0, A = CH=CH—CH=CH, R⁴ = H, and DEG = CH₂CH₂CH₂CH₂—[piperidine]—N—CH(4-Cl-C₆H₄)(4-Cl-C₆H₄), R¹ = H, k = 0, A = C≡C, R⁴ = H, and DEG = CH₂CH₂CH₂CH₂—[piperidine]—N—CH(2-Cl-C₆H₄)(2-Cl-C₆H₄), R¹ = H, k = 0, A = (CH₂)₂CH=CH, R⁴ = H, and DEG = CH₂CH₂CH₂CH₂—[piperidine]—N—CH(2-Cl-C₆H₄)(2-Cl-C₆H₄), R¹ = H, k = 0, A = CH=CH—CH=CH, R⁴ = H, and -continued

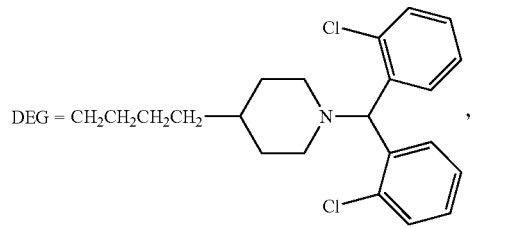

$R^1 = H, k = 0, A = CH=CH—CH=CH, R^4 = H,$ and

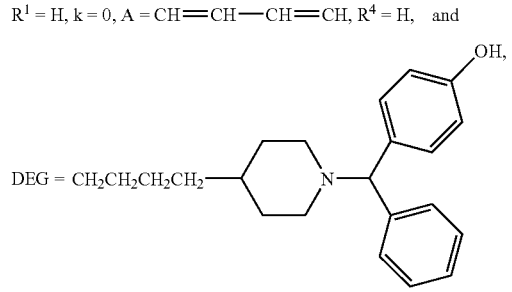

$R^1 = H, k = 0, A = CH=CH—CH=CH, R^4 = H,$ and

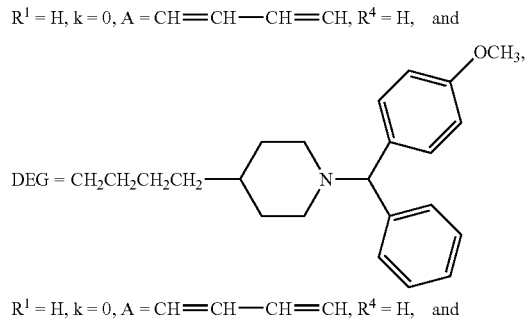

$R^1 = H, k = 0, A = CH=CH—CH=CH, R^4 = H,$ and

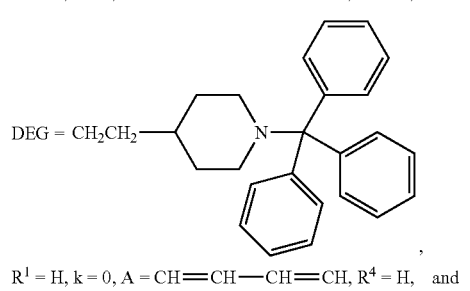

$R^1 = H, k = 0, A = CH=CH—CH=CH, R^4 = H,$ and

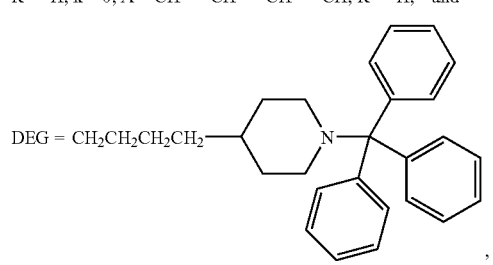

$R^1 = H, k = 0, A = CH=CH, R^4 = H,$ and

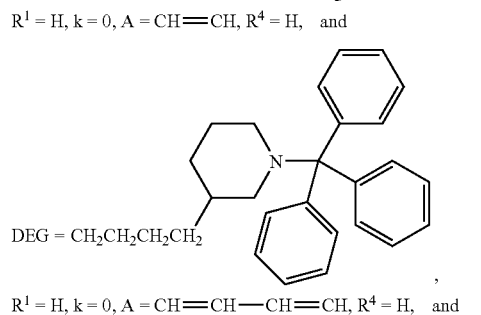

$R^1 = H, k = 0, A = CH=CH—CH=CH, R^4 = H,$ and

-continued

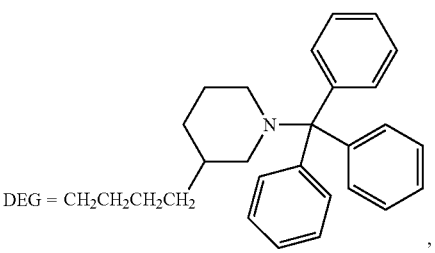

$R^1 = H, k = 0, A = CH=CH, R^4 = H,$ and

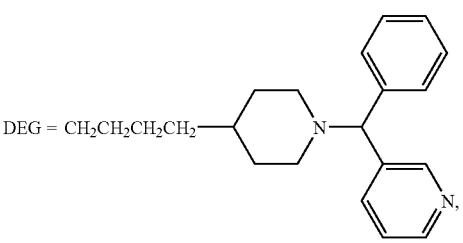

$R^1 = H, k = 0, A = CH=CH—CH=CH, R^4 = H,$ and

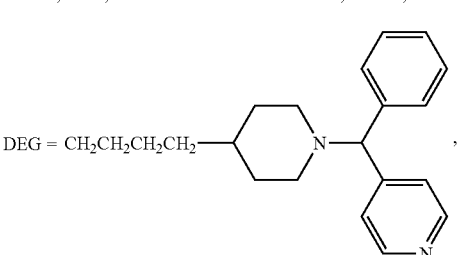

$R^1 = H, k = 0, A = CH=CH, R^4 = H,$ and

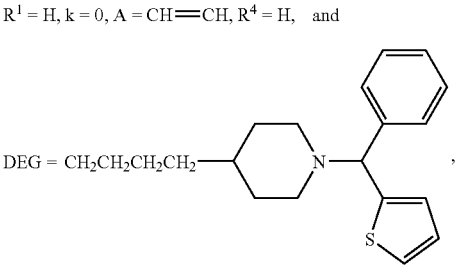

$R^1 = H, k = 0, A = CH=CH—CH=CH, R^4 = H,$ and

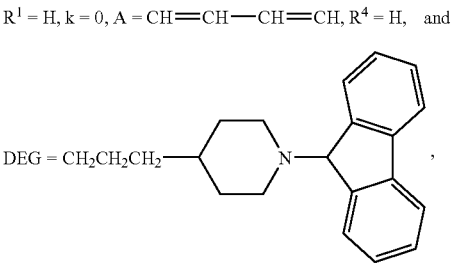

$R^1 = H, k = 0, A = CH=CH—CN, R^4 = H,$ and

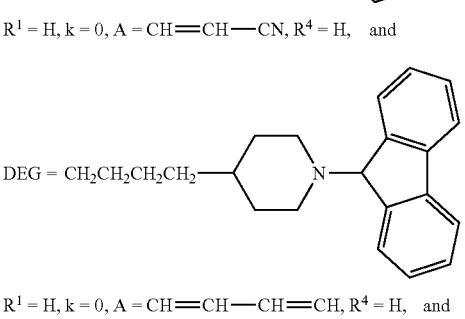

$R^1 = H, k = 0, A = CH=CH—CH=CH, R^4 = H,$ and

-continued
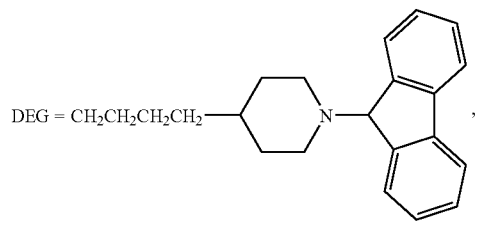
R¹ = H, k = 0, A = CH=CHCH₂CHF, R⁴ = H, and
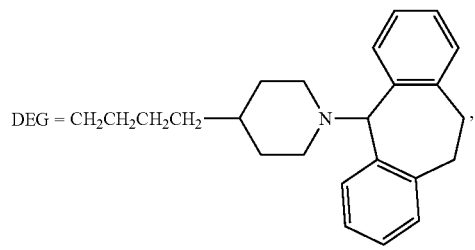
R¹ = H, k = 0, A = CH=CH—CH=CH, R⁴ = H, and
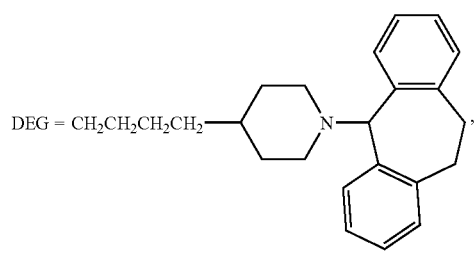
R¹ = H, k = 0, A = C≡C, R⁴ = H, and
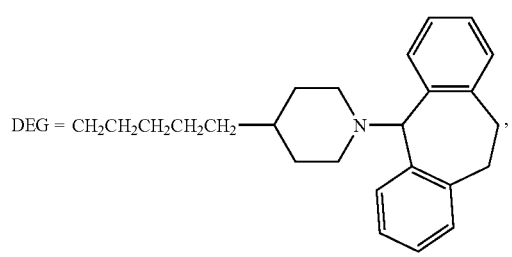
R¹ = H, k = 0, A = CH=CH, R⁴ = H, and
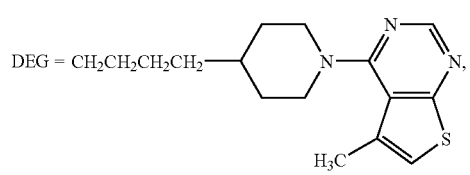
R¹ = H, k = 0, A = CH=CH—CH=CH, R⁴ = H, and
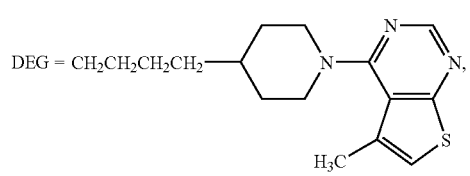
R¹ = H, k = 0, A = CH=CH, R⁴ = H, and
-continued
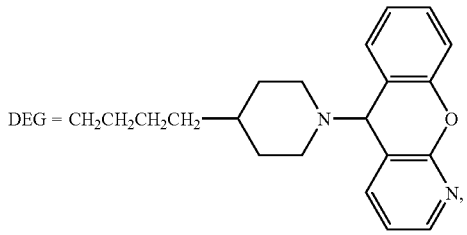
R¹ = H, k = 0, A = CH=CH, R⁴ = H, and
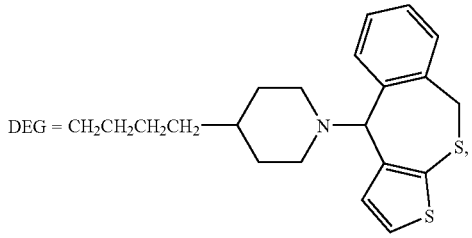
R¹ = H, k = 0, A = CH=CH, R⁴ = H, and
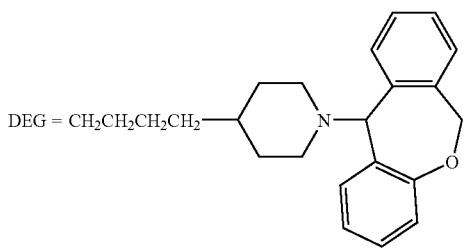
R¹ = H, k = 0, A = CH=CH—CH=CH, R⁴ = H, and
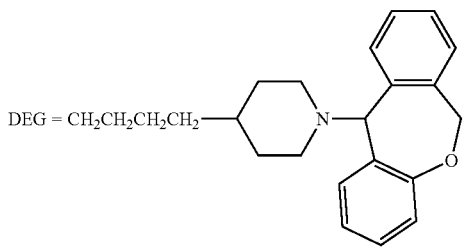
R¹ = H, k = 0, A = CH=CH, R⁴ = H, and
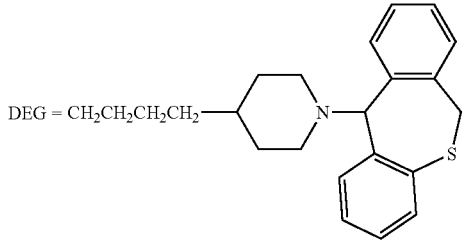
R¹ = H, k = 0, A = CH=CH—CH=CH, R⁴ = H, and
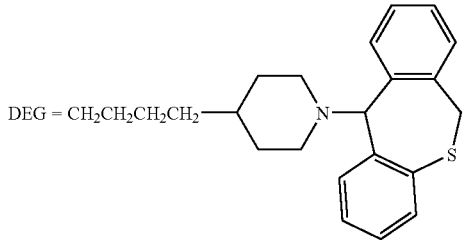
R¹ = H, k = 0, A = CH=CH, R⁴ = H, and -continued DEG = CH₂CH₂-[4-(N-acetyl)piperidine],
R¹ = H, k = 0, A = CH=CH—CH=CH, R⁴ = H, and DEG = CH₂CH₂-[4-(N-acetyl)piperidine],
R¹ = H, k = 0, A = CH=CH, R⁴ = H, and DEG = CH₂CH₂CH₂CH₂-[4-(N-acetyl)piperidine],
R¹ = H, k = 0, A = CH=CH—CH=CH, R⁴ = H, and DEG = CH₂CH₂CH₂CH₂-[4-(N-acetyl)piperidine],
R¹ = H, k = 0, A = CH=CH, R⁴ = H, and DEG = CH₂CH₂CH₂CH₂-[4-(N-acetyl)piperidine],
R¹ = H, k = 0, A = CH=CH, R⁴ = H, and DEG = CH₂CH₂CH₂CH₂-[4-(N-pivaloyl)piperidine],
R¹ = H, k = 0, A = CH=CH, R⁴ = H, and DEG = CH₂CH₂CH₂CH₂-[4-(N-cyclopropanecarbonyl)piperidine],
R¹ = H, k = 0, A = CH=CH—CH=CH, R⁴ = H, and DEG = CH₂CH₂CH₂CH₂-[4-(N-cyclopropanecarbonyl)piperidine],
R¹ = H, k = 0, A = CH=CH, R⁴ = H, and DEG = CH₂CH₂-[4-(N-phenylacetyl)piperidine],
R¹ = H, k = 0, A = CH=CH, R⁴ = H, and DEG = CH₂CH₂CH₂CH₂-[4-(N-phenylacetyl)piperidine],
R¹ = H, k = 0, A = CH=CH—CH=CH, R⁴ = H, and DEG = CH₂CH₂CH₂CH₂-[4-(N-phenylacetyl)piperidine],
R¹ = H, k = 0, A = CH=CH(CH₂)₂, R⁴ = H, and -continued DEG = CH₂-[4-(N-diphenylacetyl)piperidine],
R¹ = H, k = 0, A = CH=CH, R⁴ = H, and DEG = CH₂CH₂CH₂-[4-(N-diphenylacetyl)piperidine],
R¹ = H, k = 0, A = CH=CH—CH=CH, R⁴ = H, and DEG = CH₂CH₂CH₂-[4-(N-diphenylacetyl)piperidine],
R¹ = H, k = 0, A = CH=CH, R⁴ = H, and DEG = CH₂CH₂CH₂-[4-(N-diphenylacetyl)-3-methylpiperidine],
R¹ = H, k = 0, A = CH=CH, R⁴ = H, and DEG = CH₂CH₂CH₂-[4-(N-(3,3-diphenylpropanoyl))piperidine],
R¹ = H, k = 0, A = CH=CH—CH=CH, R⁴ = H, and DEG = CH₂CH₂CH₂-[4-(N-(3,3-diphenylpropanoyl))piperidine],
R¹ = H, k = 0, A = CH=CH, R⁴ = H, and DEG = CH₂CH₂CH₂CH₂-[4-(N-((1-phenyl-1H-pyrrol-3-yl)carbonyl))piperidine],
R¹ = H, k = 0, A = CH=CH, R⁴ = H, and -continued DEG = CH₂CH₂CH₂CH₂—[piperidine]—N-C(=O)-CH₂-N[thiazolo-pyridinone-Cl], R¹ = H, k = 0, A = CH=CH—CH=CH, R⁴ = H, and DEG = CH₂CH₂CH₂CH₂—[piperidine]—N-C(=O)-CH₂-N[benzothiazolone-Cl], R¹ = H, k = 0, A = CH=CH, R⁴ = H, and DEG = CH₂CH₂—[piperidine]—N-C(=O)-phenyl, R¹ = H, k = 0, A = CH=CH, R⁴ = H, and DEG = CH₂CH₂CH₂CH₂—[piperidine]—N-C(=O)-phenyl, R¹ = H, k = 0, A = CH=C—CH₃, R⁴ = H, and DEG = CH₂CH₂CH₂CH₂—[piperidine]—N-C(=O)-phenyl, R¹ = H, k = 0, A = CH=CHCHCHF, R⁴ = H, and
    OH DEG = CH₂CH₂CH₂CH₂—[piperidine]—N-C(=O)-phenyl, R¹ = H, k = 0, A = CH=CH—CH=CH, R⁴ = H, and DEG = CH₂CH₂CH₂CH₂—[piperidine]—N-C(=O)-pyridyl, R¹ = H, k = 0, A = CH=CH, R⁴ = H, and -continued DEG = CH₂CH₂CH=CH—[piperidine]—N-C(=O)-phenyl, R¹ = H, k = 0, A = CH=CH, R⁴ = CH₃, and DEG = CH₂CH₂N(CH₃)-C(=O)-[piperidine]—N-C(=O)-phenyl, R¹ = H, k = 0, A = CH=CH, R⁴ = H, and DEG = CH₂CH₂CH₂CH₂—[piperidine]—N-C(=O)-(2,6-dichlorophenyl), R¹ = H, k = 0, A = CH=CH, R⁴ = H, and DEG = CH₂CH₂CH₂CH₂—[piperidine]—N-C(=O)-(2-carboxyphenyl), R¹ = H, k = 0, A = CH=CH, R⁴ = H, and DEG = CH₂CH₂CH₂CH₂—[piperidine]—N-C(=O)-biphenyl, R¹ = H, k = 0, A = CH=CH—CH=CH, R⁴ = H, and DEG = CH₂CH₂CH₂CH₂—[piperidine]—N-C(=O)-biphenyl, R¹ = H, k = 0, A = CH=CH, R⁴ = H, and DEG = CH₂CH₂CH₂CH₂—[piperidine]—N-C(=O)-(2-phenylphenyl), R¹ = H, k = 0, A = (CH₂)₂CH=CH, R⁴ = H, and DEG = CH₂CH₂CH₂CH₂—[piperidine]—N-C(=O)-(2-phenylphenyl), R¹ = H, k = 0, A = CH=CH, R⁴ = H, and -continued DEG = CH₂CH₂CH₂CH₂-[piperidine]-N-C(=O)-[naphthalene], R¹ = 2-F, k = 0, A = CH=CH, R⁴ = H, and DEG = CH₂CH₂CH₂CH₂-[piperidine]-N-C(=O)-[naphthalene], R¹ = H, k = 0, A = CH=CH—CH=CH, R⁴ = H, and DEG = CH₂CH₂CH₂CH₂-[piperidine]-N-C(=O)-[naphthalene], R¹ = H, k = 0, A = CH=CH, R⁴ = H, and DEG = (CH₂)₈-[piperidine]-N-C(=O)-[naphthalene], R¹ = H, k = 0, A = CH=CH, R⁴ = H, and DEG = CH₂CH₂CH₂CH₂-[piperidine]-N-C(=O)-[naphthalene-2-yl], R¹ = H, k = 0, A = CH=CH—CH=CH, R⁴ = H, and DEG = CH₂CH₂CH₂CH₂-[piperidine]-N-C(=O)-[naphthalene-2-yl], R¹ = H, k = 0, A = CH=CH, R⁴ = H, and DEG = CH₂CH₂CH₂CH₂-[piperidine]-N-C(=O)-[fluorenone], R¹ = H, k = 0, A = CH=CH, R⁴ = H, and DEG = CH₂CH₂CH₂CH₂-[piperidine]-N-C(=O)-[fluorenone], R¹ = H, k = 0, A = CH=CH—CH=CH, R⁴ = H, and -continued DEG = CH₂CH₂CH₂CH₂-[piperidine]-N-C(=O)-[fluorenone], R¹ = H, k = 0, A = CH=CH, R⁴ = H, and DEG = (CH₂)₆-[piperidine]-N-C(=O)-[fluorenone], R¹ = H, k = 0, A = CH=CH, R⁴ = H, and DEG = CH₂CH₂CH₂CH₂-[piperidine]-N-C(=O)-[anthraquinone], R¹ = 4-F, k = 0, A = CH=CH, R⁴ = H, and DEG = CH₂CH₂CH₂CH₂-[piperidine]-N-C(=O)-[anthraquinone], R¹ = H, k = 0, A = CH=CH—CH=CH, R⁴ = H, and DEG = CH₂CH₂CH₂CH₂-[piperidine]-N-C(=O)-[anthraquinone], R¹ = H, k = 0, A = CH=CH, R⁴ = H, and DEG = CH₂CH₂CH₂CH₂-[piperidine]-N-C(=O)-[furan], R¹ = H, k = 0, A = CH=CH, R⁴ = H, and -continued DEG = CH₂CH₂CH₂CH₂—[piperidine]—N—C(=O)—[3-pyridyl], R¹ = H, k = 0, A = (CH=CH)₃, R⁴ = H, and DEG = CH₂CH₂CH₂CH₂—[piperidine]—N—C(=O)—[3-pyridyl], R¹ = H, k = 0, A = CH=CH, R⁴ = H, and DEG = CH₂CH₂CH₂CH₂—[piperidine]—N—C(=O)—[chromone-3-yl], R¹ = H, k = 0, A = CH=CH—CH=CH, R⁴ = H, and DEG = CH₂CH₂CH₂CH₂—[piperidine]—N—C(=O)—[chromone-3-yl], R¹ = H, k = 0, A = CH=CH, R⁴ = H, and DEG = CH₂CH₂CH₂CH₂—[piperidine]—N—C(=O)—[quinoxalin-2-yl], R¹ = H, k = 0, A = C≡C, R⁴ = H, and DEG = CH₂CH₂CH₂CH₂—[piperidine]—N—C(=O)—[quinoxalin-2-yl], R¹ = H, k = 0, A = CH=CH, R⁴ = H, and DEG = CH₂CH₂CH₂CH₂—[piperidine]—N—C(=O)—N(CH₃)₂, R¹ = H, k = 0, A = CH=CH, R⁴ = H, and DEG = CH₂CH₂CH₂CH₂—[piperidine]—N—C(=O)—N(CH(CH₃)₂)₂, R¹ = H, k = 0, A = CH=CH, R⁴ = H, and DEG = CH₂CH₂CH₂CH₂—[piperidine]—N—C(=O)—N(CH₂Ph)₂, R¹ = H, k = 0, A = CH=CH—CH=CH, R⁴ = H, and DEG = CH₂CH₂CHCH₂—[piperidine]—N—C(=O)—NH—CH₂—[2-furyl], R¹ = H, k = 0, A = CH=CH, R⁴ = H, and DEG = CH₂CH₂CH₂CH₂—[piperidine]—N—C(=O)—NH—[1-naphthyl], R¹ = 2-Cl, k = 0, A = CH=CH, R⁴ = H, and DEG = CH₂CH₂CH₂CH₂—[piperidine]—N—C(=O)—NH—[1-naphthyl], R¹ = H, k = 0, A = CH=CH, R⁴ = H, and DEG = CH₂CH₂CH₂OCH₂—[piperidine]—N—C(=O)—NH—[1-naphthyl], R¹ = H, k = 0, A = CH=CH, R⁴ = H, and DEG = CH₂CH₂—[piperidine]—N—C(=O)—N(Ph)₂, R¹ = H, k = 0, A = CH=CH, R⁴ = H, and DEG = CH₂CH₂CH₂CH₂—[piperidine]—N—C(=O)—N(Ph)₂, R¹ = H, k = 0, A = CH=CH—CH=CH, R⁴ = H, and -continued DEG = CH₂CH₂CH₂CH₂-[piperidine]-C(=O)-N(phenyl)₂, R¹ = H, k = 0, A = CH=CH, R⁴ = H, and DEG = CH₂CH₂CH₂CH₂-[piperidine]-C(=O)-[indoline], R¹ = H, k = 0, A = CH=CH—CH=CH, R⁴ = H, and DEG = CH₂CH₂CH₂CH₂-[piperidine]-C(=O)-[indoline], R¹ = H, k = 0, A = CH=CH, R⁴ = H, and DEG = CH₂CH₂CH₂CH₂-[piperidine]-C(=O)-[10,11-dihydrodibenzazepine], R¹ = H, k = 0, A = CH=CH—CH=CH, R⁴ = H, and DEG = CH₂CH₂CH₂CH₂-[piperidine]-C(=O)-[10,11-dihydrodibenzazepine], R¹ = H, k = 0, A = CH=CH, R⁴ = H, and DEG = CH₂CH₂CH₂CH₂-[piperidine]-C(=O)-[dibenzazocine], R¹ = H, k = 0, A = CH=CH—CH=CH, R⁴ = H, and DEG = CH₂CH₂CH₂CH₂-[piperidine]-C(=O)-[dibenzazocine], R¹ = H, k = 0, A = CH=CH, R⁴ = H, and DEG = CH₂CH₂-[piperidine]-N-SO₂-CH₃, R¹ = H, k = 0, A = CH=CH, R⁴ = H, and DEG = CH₂CH₂CH₂CH₂-[piperidine]-N-SO₂-CH₃, R¹ = H, k = 0, A = CH=CH—CH=CH, R⁴ = H, and DEG = CH₂CH₂CH₂CH₂-[piperidine]-N-SO₂-CH₃, R¹ = H, k = 0, A = CH=CH, R⁴ = H, and DEG = (CH₂)₆-[piperidine]-N-SO₂-CH₃, R¹ = H, k = 0, A = CH=CH, R⁴ = H, and DEG = CH₂CH₂CH₂NH-[piperidine]-N-SO₂-CH₃, R¹ = H, k = 0, A = CH=CH, R⁴ = H, and DEG = CH₂-[piperidine]-N-SO₂-C₆H₄-CH₃, R¹ = H, k = 0, A = CH=CH, R⁴ = H, and DEG = CH₂CH₂CH₂CH₂-[piperidine]-N-SO₂-C₆H₄-CH₃, R¹ = H, k = 0, A = CH=CH—CH=CH, R⁴ = H, and DEG = CH₂CH₂CH₂CH₂-[piperidine]-N-SO₂-C₆H₄-CH₃, R¹ = H, k = 0, A = CH=CH, R⁴ = H, and DEG = CH₂CH₂-[piperidine]-N-SO₂-[naphthalen-1-yl], R¹ = H, k = 0, A = CH=CH, R⁴ = H, and DEG = CH₂CH₂CH₂CH₂-[piperidine]-N-SO₂-[naphthalen-1-yl], R¹ = H, k = 0, A = CH=CH, R⁴ = H, and DEG = CH₂CH₂-[piperidine]-N-SO₂-[naphthalen-2-yl], R¹ = H, k = 0, A = CH=CH—CH=CH, R⁴ = H, and DEG = CH₂CH₂-[piperidine]-N-SO₂-[naphthalen-2-yl], R¹ = H, k = 0, A = CH=CH, R⁴ = H, and

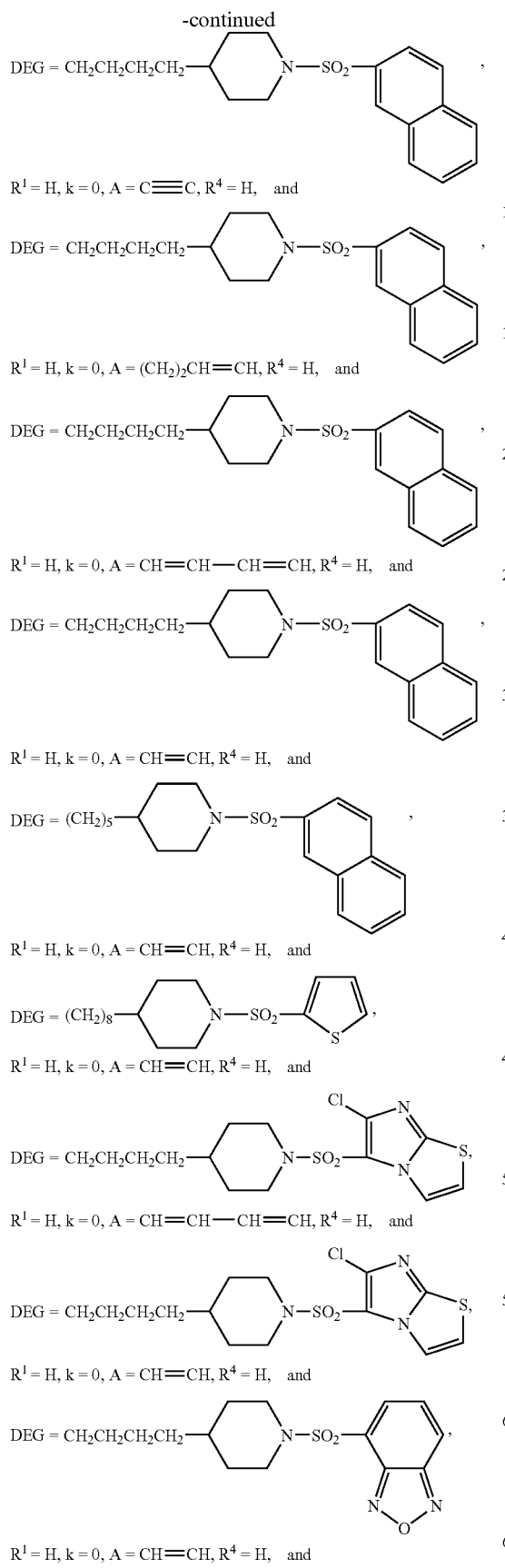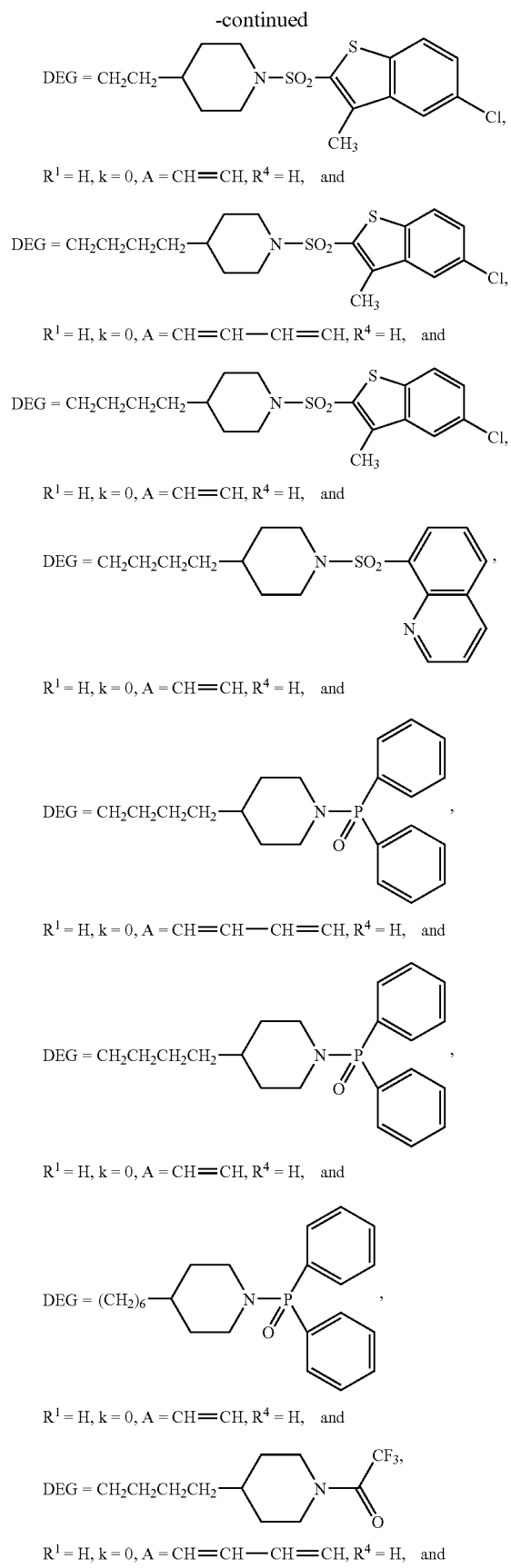

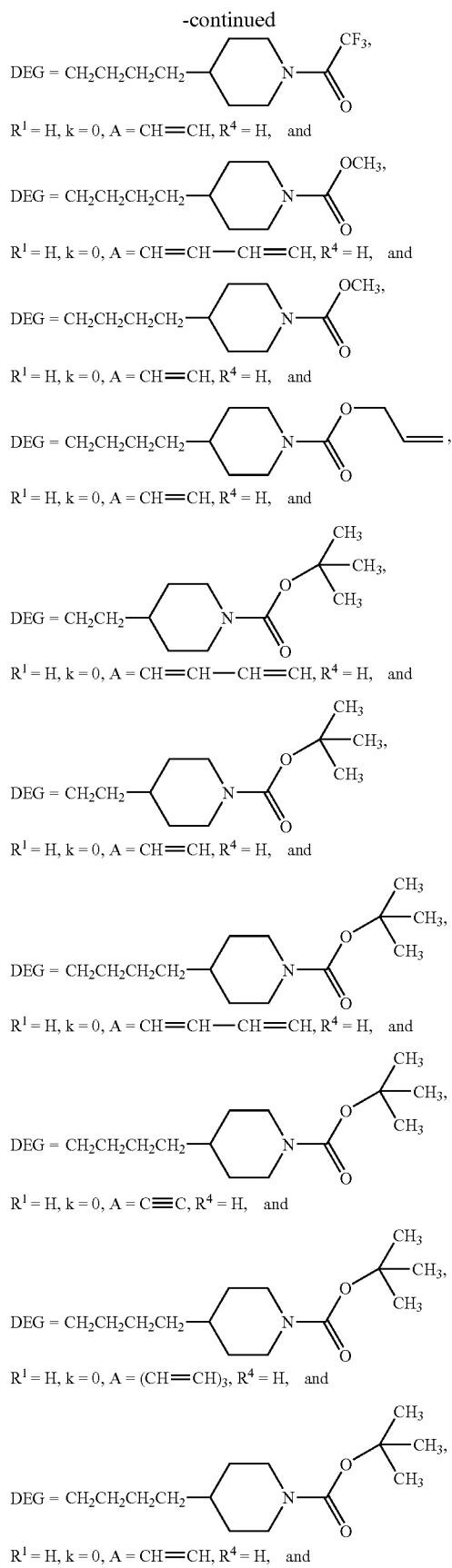
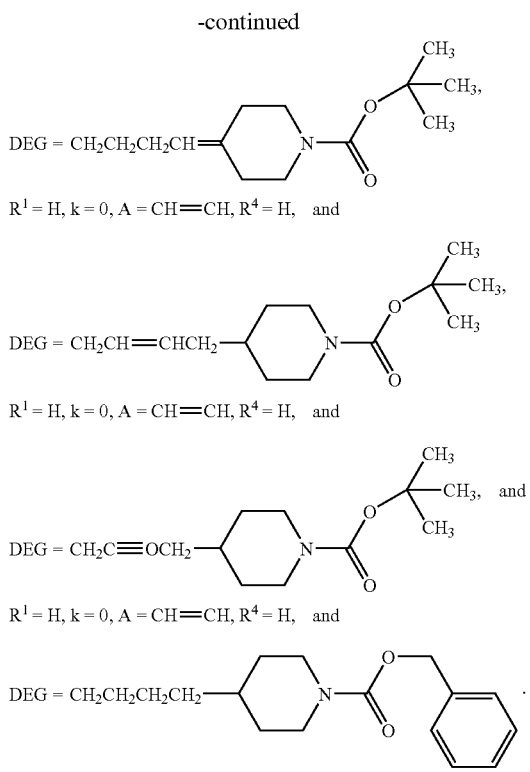
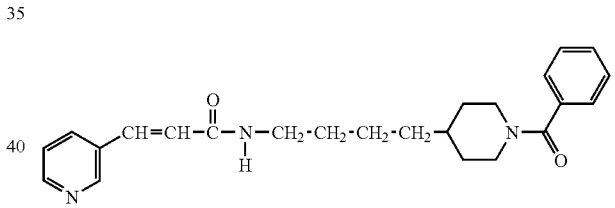
7. The compound of formula (I) according to claim 6, which is
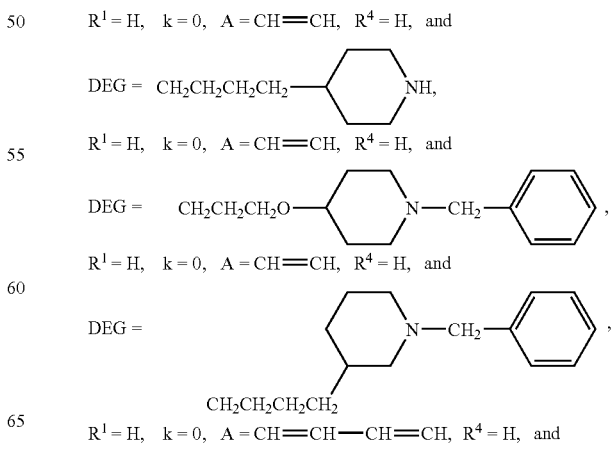
or a pharmaceutically acceptable acid addition salt thereof.
8. The compound of claim 6, the compound of formula (I) being selected from the group consisting of -continued DEG = CH₂CH₂CH₂CH₂—[piperidine]—N—CH₂—[pyridine], R¹ = H, k = 0, A = CH=CH, R⁴ = H, and DEG = CH₂CH₂CH₂CH₂—[piperidine]—N—CH₂—[benzofurazan], R¹ = H, k = 0, A = CH=CH, R⁴ = H, and DEG = CH₂—[piperidine]—N—CH(C₆H₅)₂, R¹ = H, k = 0, A = CH=CH, R⁴ = H, and DEG = NH—C(=O)—[piperidine]—N—CH(C₆H₅)₂, R¹ = H, k = 0, A = CH=CH, R⁴ = H, and DEG = CH₂CH₂NH—[piperidine]—N—CH(C₆H₅)₂, R¹ = H, k = 1, A = CH=CH, R⁴ = H, and DEG = CH₂CH₂CH₂CH₂—[piperidine]—N—CH(C₆H₅)₂, R¹ = H, k = 0, A = C≡C, R⁴ = H, and DEG = CH₂CH₂CH₂CH₂—[piperidine]—N—CH(C₆H₅)₂, R¹ = H, k = 0, A = (CH₂)₂CH=CH, R⁴ = H, and DEG = CH₂CH₂CH₂CH₂—[piperidine]—N—CH(C₆H₅)₂, R¹ = H, k = 0, A = CH=CH—CH=CH, R⁴ = H, and DEG = CH₂CH₂CH₂CH₂—[piperidine]—N—CH(C₆H₅)₂, R¹ = H, k = 0, A = CH=CH—CH=CH, R⁴ = H, and DEG = CH₂CH₂CH₂CH₂—[piperidine]—N—CH(C₆H₅)₂, R¹ = H, k = 0, A = CH=CH, R⁴ = H, and DEG = CH₂CH₂CH₂CH₂—[piperidine]—N—CH(C₆H₅)₂, R¹ = 5-F, k = 0, A = CH=CH, R⁴ = H, and DEG = CH₂CH₂CH₂CH₂—[piperidine]—N—CH(C₆H₅)₂, R¹ = H, k = 0, A = CH=CH, R⁴ = H, and -continued DEG = CH₂CH₂CH₂CH₂O—[piperidine]—N—CH(C₆H₅)₂, R¹ = H, k = 0, A = CH=CH, R⁴ = H, and DEG = CH₂CH₂NH—C(=O)—O—[piperidine]—N—CH(C₆H₅)₂, R¹ = H, k = 0, A = CH=CH—CH=CH, R⁴ = H, and DEG = CH₂CH₂CH₂CH₂CH₂—[piperidine]—N—CH(C₆H₅)₂, R¹ = H, k = 0, A = CH=CH, R⁴ = H, and DEG = (CH₂)₈—[piperidine]—N—CH(C₆H₅)₂, R¹ = H, k = 0, A = CH=CH, R⁴ = H, and DEG = (CH₂)₆NH—C(=O)—[piperidine]—N—CH(C₆H₅)₂, R¹ = H, k = 0, A = CH=CH, R⁴ = H, and DEG = CH₂CH₂CH₂—[piperidine]—N—C(C₆H₅)₃, R¹ = H, k = 0, A = CH=CH—CH=CH, R⁴ = H, and DEG = CH₂CH₂CH₂CH₂—[piperidine]—N—CH(C₆H₅)(4-pyridyl), R¹ = H, k = 0, A = CH=CH—CH=CH, R⁴ = H, and DEG = CH₂CH₂CH₂CH₂—[piperidine]—N—(9-fluorenyl), R¹ = H, k = 0, A = CH=CH, R⁴ = H, and -continued DEG = CH₂CH₂CH₂CH₂— 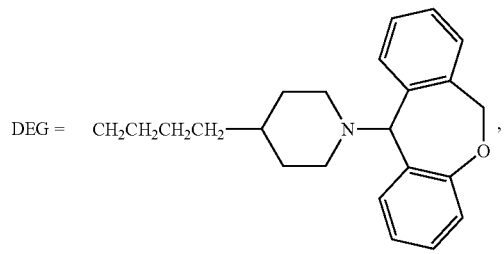

R¹ = H, k = 0, A = CH═CH, R⁴ = H, and

DEG = CH₂CH₂CH₂CH₂— 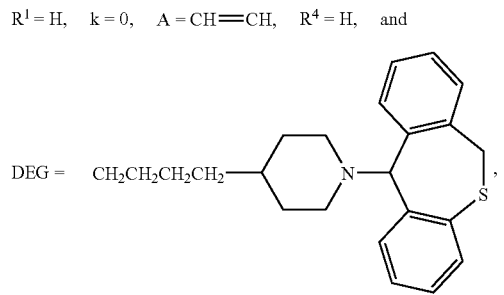

R¹ = H, k = 0, A = CH═CH, R⁴ = H, and

DEG = CH₂CH₂CH₂CH₂— 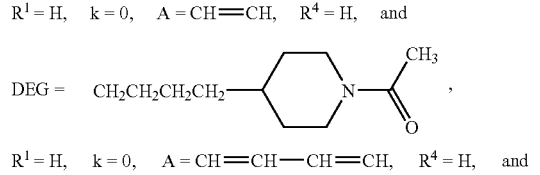

R¹ = H, k = 0, A = CH═CH—CH═CH, R⁴ = H, and

DEG = CH₂CH₂CH₂CH₂— 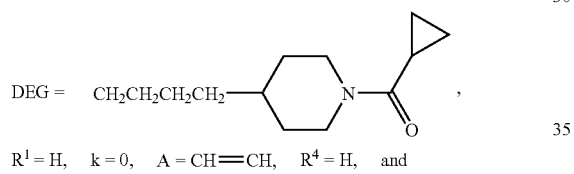

R¹ = H, k = 0, A = CH═CH, R⁴ = H, and

DEG = CH₂CH₂CH₂CH₂— 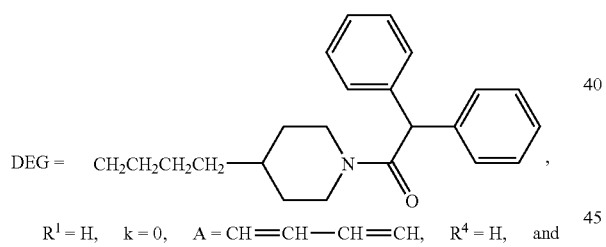

R¹ = H, k = 0, A = CH═CH—CH═CH, R⁴ = H, and

DEG = CH₂CH₂CH₂CH₂— 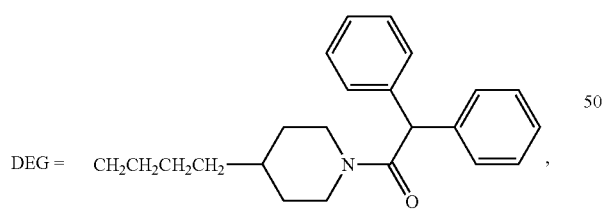

R¹ = H, k = 0, A = CH═CH, R⁴ = H, and

DEG = CH₂CH₂CH₂CH₂— 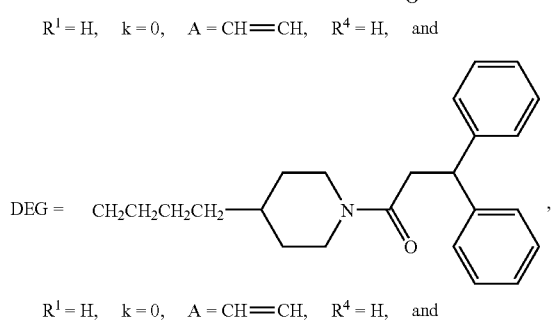

R¹ = H, k = 0, A = CH═CH, R⁴ = H, and

-continued

DEG = CH₂CH₂— 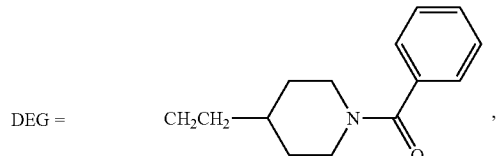

R¹ = H, k = 0, A = CH═CH, R⁴ = H, and

DEG = CH₂CH₂CH₂— 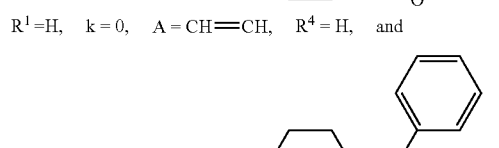

R¹ = H, k = 0, A = CH═C—CH₃, R⁴ = H, and

DEG = CH₂CH₂CH₂— 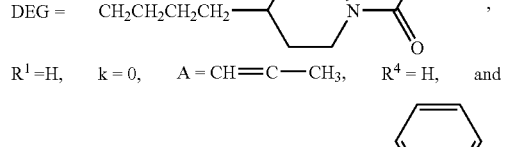

R¹ = H, k = 0, A = CH═CH—CH═CH, R⁴ = H, and

DEG = CH₂CH₂CH₂— 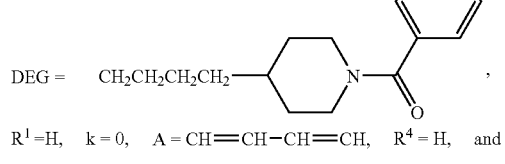

R¹ = H, k = 0, A = (CH₂)₂CH═CH, R⁴ = H, and

DEG = CH₂CH₂CH₂CH₂— 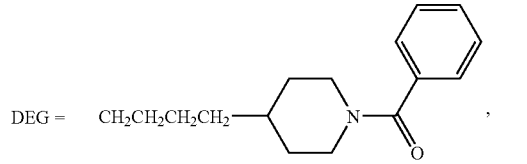

R¹ = H, k = 0, A = CH═CH, R⁴ = H, and

DEG = (CH₂)₈— 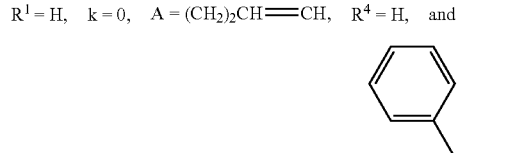

R¹ = H, k = 0, A = CH═CH, R⁴ = H, and

DEG = CH₂CH₂CH₂CH₂— 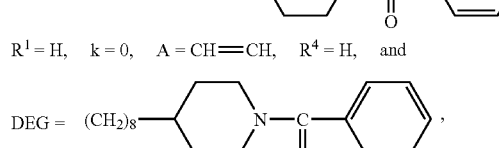

R¹ = H, k = 0, A = CH═CH, R⁴ = H, and

DEG = CH₂CH₂CH₂CH₂—

R¹ = H, k = 0, A = CH═CH, R⁴ = H, and

-continued

DEG = CH₂CH₂CH₂CH₂- 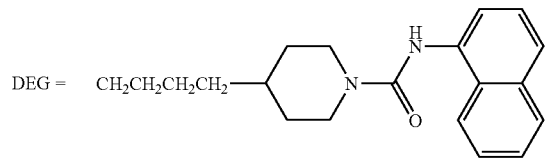

R¹ = H,  k = 0,  A = CH═CH,  R⁴ = H,  and

DEG = CH₂CH₂CH₂CH₂- 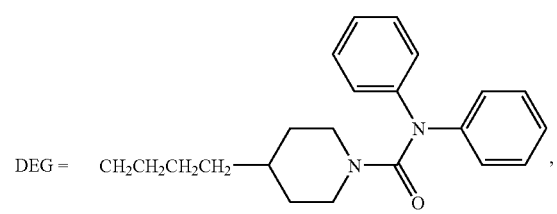

R¹ = H,  k = 0,  A = CH═CH—CH═CH,  R⁴ = H,  and

DEG = CH₂CH₂CH₂CH₂- 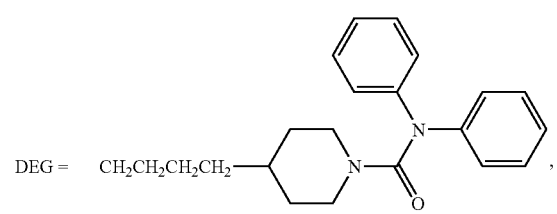

R¹ = H,  k = 0,  A = CH═CH,  R⁴ = H,  and

DEG = CH₂CH₂CH₂CH₂- 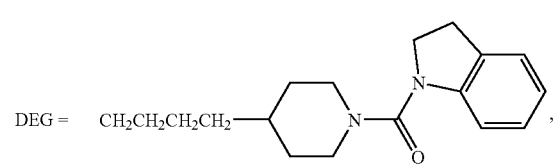

R¹ = H,  k = 0,  A = CH═CH—CH═CH,  R⁴ = H,  and

DEG = CH₂CH₂CH₂CH₂- 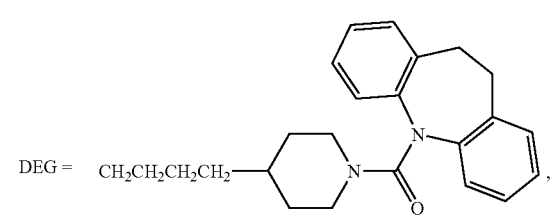

R¹ = H,  k = 0,  A = CH═CH,  R⁴ = H,  and

DEG = CH₂CH₂CH₂CH₂- 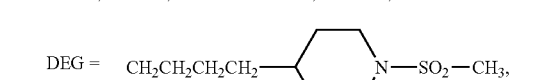,

R¹ = H,  k = 0,  A = CH═CH,  R⁴ = H,  and

DEG = (CH₂)₆- 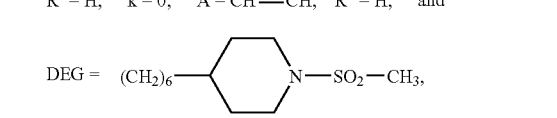,

R¹ = H,  k = 0,  A = CH═CH,  R⁴ = H,  and

DEG = CH₂CH₂- 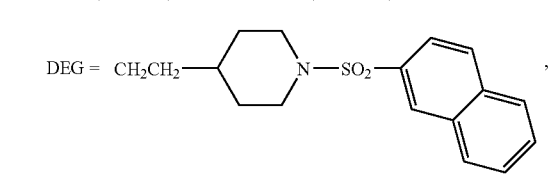,

R¹ = H,  k = 0,  A = CH═CH,  R⁴ = H,  and

-continued

DEG = CH₂CH₂CH₂CH₂- 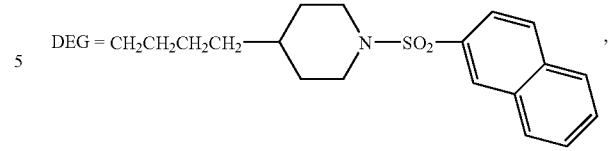,

R¹ = H,  k = 0,  A = CH═CH—CH═CH,  R⁴ = H,  and

DEG = CH₂CH₂CH₂CH₂- 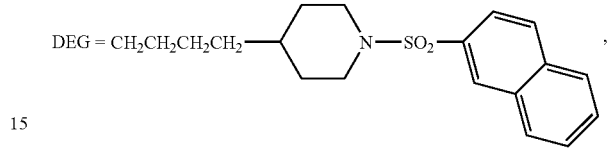,

R¹ = H,  k = 0,  A = CH═CH,  R⁴ = H,  and

DEG = CH₂CH₂CH₂CH₂- 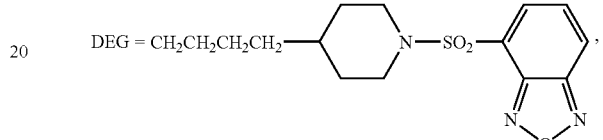,

R¹ = H,  k = 0,  A = CH═CH—CH═CH,  R⁴ = H,  and

DEG = CH₂CH₂CH₂CH₂- 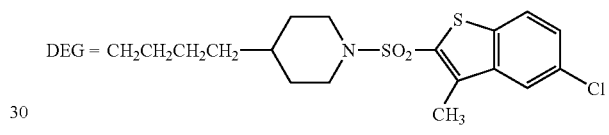,

R¹ = H,  k = 0,  A = CH═CH,  R⁴ = H,  and

DEG = CH₂CH₂CH₂CH₂- 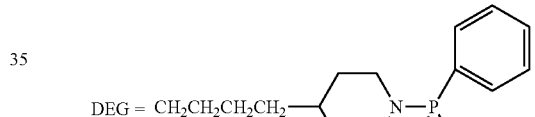,

R¹ = H,  k = 0,  A = CH═CH,  R⁴ = H,  and

DEG = (CH₂)₆- 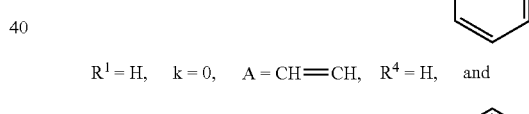,

R¹ = H,  k = 0,  A = CH═CH,  R⁴ = H,  and

DEG = CH₂CH₂CH₂CH₂- 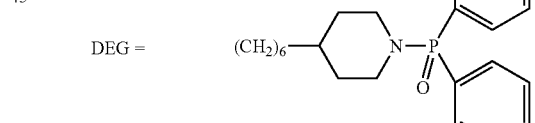,

R¹ = H,  k = 0,  A = CH═CH—CH═CH,  R⁴ = H,  and

DEG = CH₂CH₂CH₂CH₂- 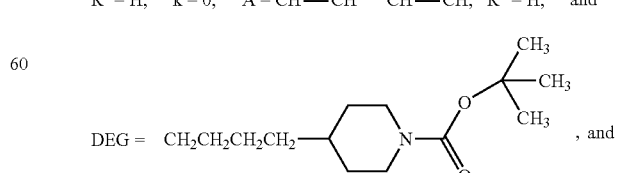, and

R¹ = H,  k = 0,  A = C≡C,  R⁴ = H,  and

-continued
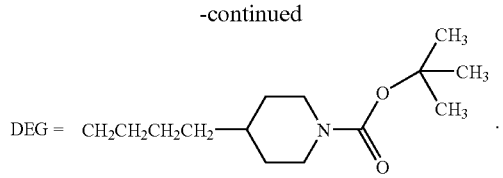
9. The compound of claim 6, claim 7, or claim 8 in a pharmaceutical composition in the form selected from the group consisting of tablets, hard gelatin capsules, soft gelatin capsules, soft gelatin capsules, coated tablets powders, pellets, microcapsules, oblong compressives, granules, chewable tablets, lozenges, gums, and sachets.
* * * * *